US012351829B2

(12) United States Patent
Boccellato et al.

(10) Patent No.: US 12,351,829 B2
(45) Date of Patent: Jul. 8, 2025

(54) GENERATION, PROLIFERATION AND EXPANSION OF EPITHELIAL CELLS FROM PRIMARY TISSUE INTO MUCOSOID CULTURES

(71) Applicant: Max-Planck-Gesellschaft zur Förderung der Wissenschaften e.V., Munich (DE)

(72) Inventors: Francesco Boccellato, Berlin (DE); Thomas F. Meyer, Falkensee (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 713 days.

(21) Appl. No.: 16/962,672

(22) PCT Filed: Jan. 18, 2019

(86) PCT No.: PCT/EP2019/051287
§ 371 (c)(1),
(2) Date: Jul. 16, 2020

(87) PCT Pub. No.: WO2019/141824
PCT Pub. Date: Jul. 25, 2019

(65) Prior Publication Data
US 2020/0362312 A1    Nov. 19, 2020

(30) Foreign Application Priority Data

Jan. 18, 2018  (EP) ..................... 18152395
Feb. 16, 2018  (EP) ..................... 18157173

(51) Int. Cl.
*C12N 5/071* (2010.01)
(52) U.S. Cl.
CPC ......... *C12N 5/0679* (2013.01); *C12N 5/0682* (2013.01); *C12N 2502/11* (2013.01); *C12N 2539/00* (2013.01)
(58) Field of Classification Search
None
See application file for complete search history.

(56) References Cited

U.S. PATENT DOCUMENTS

| 2010/0047853 | A1* | 2/2010 | Kuo ..................... | C12N 5/0012 |
|---|---|---|---|---|
| | | | | 435/325 |
| 2014/0302491 | A1 | 10/2014 | Nadauld et al. | |
| 2016/0060594 | A1* | 3/2016 | Xian ..................... | A61K 35/39 |
| | | | | 435/405 |
| 2018/0002672 | A1* | 1/2018 | Allbritton ............ | C12N 5/0679 |

FOREIGN PATENT DOCUMENTS

WO    2016123474 A1    8/2016

OTHER PUBLICATIONS

Navabi, N., McGuckin, M. A., & Lindén, S. K. (2013). Gastrointestinal cell lines form polarized epithelia with an adherent mucus layer when cultured in semi-wet interfaces with mechanical stimulation. PloS one, 8(7), e68761. (Year: 2013).*
Kauffman, A. L., Gyurdieva, A. V., Mabus, J. R., Ferguson, C., Yan, Z., & Hornby, P. J. (2013). Alternative functional in vitro models of human intestinal epithelia. Frontiers in Pharmacology, 4, 79. (Year: 2013).*
Roignot J, Peng X, Mostov K. Polarity in mammalian epithelial morphogenesis. Cold Spring Harb Perspect Biol. Feb. 1, 2013;5(2): a013789. doi: 10.1101/cshperspect.a013789. PMID: 23378592; PMCID: PMC3552506. (Year: 2013).*
Corning Incorporated Life Sciences. Costar® Transwell-COL® Product Description. Dec. 31, 2013; https://certs-ecatalog.corning.com/life-sciences/product-descriptions/3495.pdf. (Year: 2013).*
Birchenough, G., Johansson, M., Gustafsson, J et al. New developments in goblet cell mucus secretion and function. Mucosal Immunol. Jul. 2015; 8: 712-719. https://doi.org/10.1038/mi.2015.32. (Year: 2015).*
Lock JY, Carlson TL, Carrier RL. Mucus models to evaluate the diffusion of drugs and particles. Adv Drug Deliv Rev. Jan. 15, 2018; 124:34-49. doi: 10.1016/j.addr.2017.11.001. Epub Nov. 5, 2017. PMID: 29117512; PMCID: PMC6463479. (Year: 2017).*
Nossol C, et al. Air-liquid interface cultures enhance the oxygen supply and trigger the structural and functional differentiation of intestinal porcine epithelial cells (IPEC). Histochem Cell Biol. Jul. 2011;136(1):103-15. doi: 10.1007/s00418-011-0826-y. Epub Jun. 17, 2011. (Year: 2011).*
Boccellato et al, "Polarised epithelial monolayers of the gastric mucosa reveal insights into mucosal homeostasis and defence against infection", Get, 2018. 0: pp. 1-14.
Kessler et al, "The Notch and Wnt pathways regulate stemness and differentiation in human fallopian tube organoids", Nature communications, 2015, 6: pp. 8989-8989.
Tyanova et al, "The MaxQuant computational platform for mass spectrometry-based shotgun proteomics", Nat Protoc, 2016, 11(12): pp. 2301-2319.
Nossol et al, "Air-liquid interface cultures enhance the oxygen supply and trigger the structural and functional differentiation of intestinal porcine epithelial cells (IPEC)", Histochem Cell Biol, 2011, 136(1): pp. 103-115.
Yokoyama et al, "Differentiation of gastric surface mucous cells (GSM06) induced by air-liquid interface is regulated partly through mitogen-activated protein kinase pathway", J Gastroenterol Hepatol, 2007, 22(12): pp. 2310-2315.
Ootani et al, "Foveolar differentiation of mouse gastric mucosa in vitro", Am J Pathol, 2003, 162(6): pp. 1905-1912.
Butor and Davoust, "Apical to basolateral surface area ratio and polarity of MDCK cells grown on different supports", Exp Cell Res, 1992, 203(1): pp. 115-127.
Schlaermann et al, "A novel human gastric primary cell culture system for modelling Helicobacter pylori infection in vitro", Gut Published Online First: Dec. 24, 2014. doi: 10.1136/gutjnl-2014-307949; also published in Gut 2016;65:202-213.

(Continued)

*Primary Examiner* — Allison M Fox
*Assistant Examiner* — Alyssa G Weston
(74) *Attorney, Agent, or Firm* — Rothwell, Figg, Ernst & Manbeck, P.C.

(57) ABSTRACT

The invention relates to a method of culturing an epithelial cell on a solid surface.

16 Claims, 21 Drawing Sheets

Figure 1:
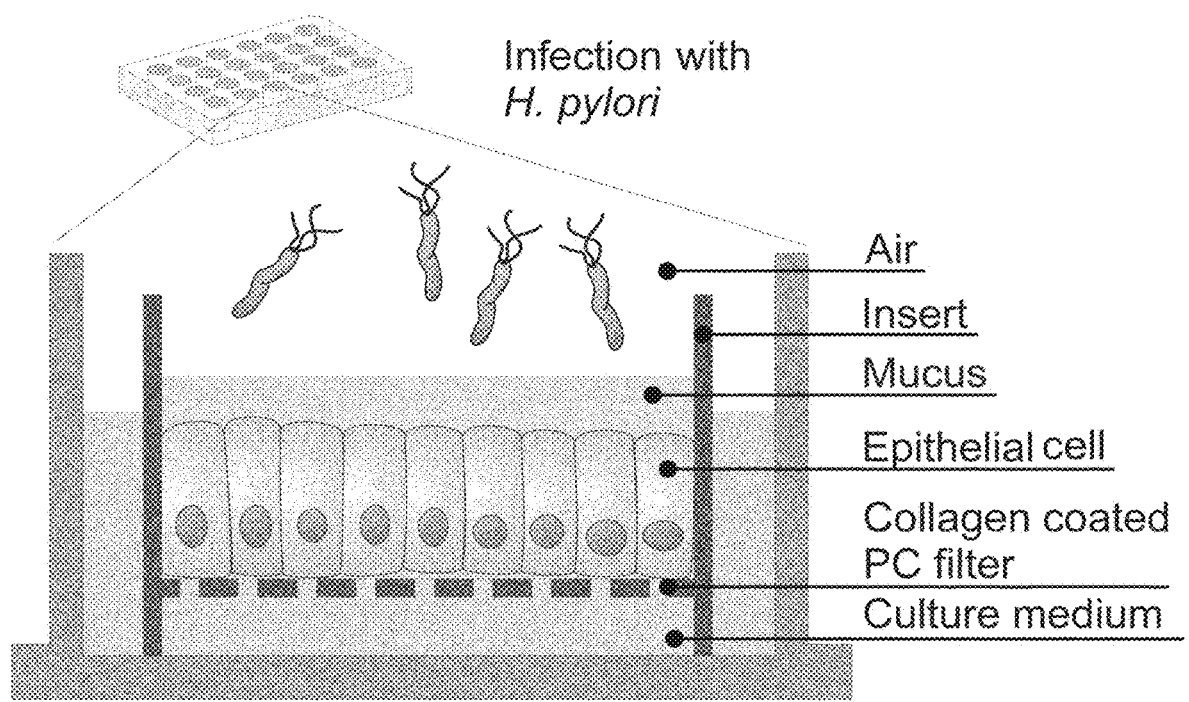

Specification includes a Sequence Listing.

(56) References Cited

OTHER PUBLICATIONS

Bartfeld et al, "In vitro expansion of human gastric epithelial stem cells and their responses to bacterial infection", Gastroenterology, 2015, 148(1): pp. 126-136.e6.

Khurana et al, "The hyaluronic acid receptor CD44 coordinates normal and metaplastic gastric epithelial progenitor cell proliferation", J Biol Chem, 2013, 288(22): pp. 16085-16097.

Gudipaty and Rosenblatt, "Epithelial cell extrusion: Pathways and pathologies", Semin Cell Dev Biol, 2017, 67: pp. 132-140.

Madara, "Maintenance of the macromolecular barrier at cell extrusion sites in intestinal epithelium: physiological rearrangement of tight junctions", J Membr Biol, 1990, 116(2): pp. 177-184.

Barker et al, "Lgr5(+ve) stem cells drive self-renewal in the stomach and build long-lived gastric units in vitro", Cell Stem Cell, 2010, 6(1): pp. 25-36.

Srinivasan et al, "TEER measurement techniques for in vitro barrier model systems", J Lab Autom, 2015, 20(2): pp. 107-126.

Choi et al, "Cell lineage distribution atlas of the human stomach reveals heterogeneous gland populations in the gastric antrum", Gut, 2014, 63(11): pp. 1711-1720.

Nordman et al, "Gastric MUC5AC and MUC6 are large oligomeric mucins that differ in size, glycosylation and tissue distribution", Biochem J, 2002, 364(Pt 1): pp. 191-200.

Babu et al, "Expression profile of mucins (MUC2, MUC5AC and MUC6) in Helicobacter pylori infected pre-neoplastic and neoplastic human gastric epithelium", Mol Cancer, 2006, 5: p. 10.

McCracken et al., "Wnt/beta-catenin promotes gastric fundus specification in mice and humans", Nature, 2017, 541 (7636): pp. 182-187.

Bauer et al., "The Helicobacter pylori virulence effector CagA abrogates human beta-defensin 3 expression via nactivation of EGFR signaling", Cell Host Microbe, 2012, 11(6): pp. 576-586.

Wisniewski et al, "Universal sample preparation method for proteome analysis", Nat Methods, 2009, 6(5): pp. 359-362.

Rodriguez-Pineiro et al, "Studies of mucus in mouse stomach, small intestine, and colon. II. Gastrointestinal mucus proteome reveals Muc2 and Muc5ac accompanied by a set of core proteins", Am J Physiol Gastrointest Liver Physiol, 2013, 305(5): pp. G348-G356.

Cox and Mann, "MaxQuant enables high peptide identification rates, individualized p.p.b.-range mass accuracies and proteome-wide protein quantification", Nat Biotechnol, 2008, 26(12): pp. 1367-1372.

Nazanin Navabi et al: "Gastrointestinal Cell Lines Form Polarized Epithelia with an Adherent Mucus Layer when Cultured in Semi-Wet Interfaces with Mechanical Stimulation", PLOS ONE, vol. 8, No. 7, Jul. 15, 2013, 15 pages.

Michaela Aufderheide et al., "CULTEX—an alternative technique for cultivation and exposure of cells of the respiratory tract to airborne pollutants at the air/liquid interface", Experimental and Toxicologic Pathology, Jan. 1, 2000 (Jan. 1, 2000), pp. 265-270.

Martin Rosdy et al., "Terminal Epidermal Differentiation of Human Keratinocytes Grown in Chemically Defined Medium on Inert Filter Substrates at the Air-Liquid Interface", Journal of Investigative Dermatology, vol. 95, No. 4, Oct. 1, 1990, pp. 409-414.

International Search Report cited in PCT/EP2019/051287 dated Mar. 8, 2019, 2 pages.

Yang et al., "Meeting future challenges in topical ocular drug delivery: Development of an air-interfaced primary culture of rabbit conjunctival epithelial cells on a permeable support for drug transport studies", Journal of Controlled Release 65 (2000) pp. 1-11.

Communication pursuant to Article 94(3) EPC issued in EP 19 700 937.6-1118 dated Apr. 3, 2023, 6 pgs.

* cited by examiner

A

B The mucus is a physical barrier agains infection

C Mucus bactericidal activity

+W +R

-W -R

SEQUENCE LISTING

<160> NUMBER OF SEQ ID NOS: 76

<210> SEQ ID NO 1
<211> LENGTH: 20
<212> TYPE: DNA
<213> ORGANISM: Artificial Sequence
<220> FEATURE:
<223> OTHER INFORMATION: CXCL1-3 Forward Primer

<400> SEQUENCE: 1
cgcccaaacc gaagtcatag					20

<210> SEQ ID NO 2
<211> LENGTH: 23
<212> TYPE: DNA
<213> ORGANISM: Artificial Sequence
<220> FEATURE:
<223> OTHER INFORMATION: CXCL1-3 Reverse Primer

<400> SEQUENCE: 2
gctccccttg ttcagtatct ttt				23

<210> SEQ ID NO 3
<211> LENGTH: 21
<212> TYPE: DNA
<213> ORGANISM: Artificial Sequence
<220> FEATURE:
<223> OTHER INFORMATION: CCL20 Forward Primer

<400> SEQUENCE: 3
tgctgtacca agagtttgct c					21

<210> SEQ ID NO 4
<211> LENGTH: 23
<212> TYPE: DNA
<213> ORGANISM: Artificial Sequence
<220> FEATURE:
<223> OTHER INFORMATION: CCL20 Reverse Primer

<400> SEQUENCE: 4
cgcacacaga caactttttc ttt				23

<210> SEQ ID NO 5
<211> LENGTH: 20
<212> TYPE: DNA
<213> ORGANISM: Artificial Sequence
<220> FEATURE:
<223> OTHER INFORMATION: LTB Forward Primer

<400> SEQUENCE: 5
gtacgggcct ctctggtaca					20

<210> SEQ ID NO 6
<211> LENGTH: 20
<212> TYPE: DNA
<213> ORGANISM: Artificial Sequence
<220> FEATURE:
<223> OTHER INFORMATION: LTB Reverse Primer

<400> SEQUENCE: 6
gtccaccata tcggggtgac					20

<210> SEQ ID NO 7
<211> LENGTH: 21
<212> TYPE: DNA
<213> ORGANISM: Artificial Sequence

```
<220> FEATURE:
<223> OTHER INFORMATION: IL23A Forward Primer

<400> SEQUENCE: 7
ctcagggaca acagtcagtt c                                      21

<210> SEQ ID NO 8
<211> LENGTH: 19
<212> TYPE: DNA
<213> ORGANISM: Artificial Sequence
<220> FEATURE:
<223> OTHER INFORMATION: IL23A Reverse Primer

<400> SEQUENCE: 8
acagggctat cagggagca                                         19

<210> SEQ ID NO 9
<211> LENGTH: 21
<212> TYPE: DNA
<213> ORGANISM: Artificial Sequence
<220> FEATURE:
<223> OTHER INFORMATION: KRT19 Forward Primer

<400> SEQUENCE: 9
gtcacagctg agcatgaaag c                                      21

<210> SEQ ID NO 10
<211> LENGTH: 19
<212> TYPE: DNA
<213> ORGANISM: Artificial Sequence
<220> FEATURE:
<223> OTHER INFORMATION: KRT19 Reverse Primer

<400> SEQUENCE: 10
agctgggctt caataccgc                                         19

<210> SEQ ID NO 11
<211> LENGTH: 21
<212> TYPE: DNA
<213> ORGANISM: Artificial Sequence
<220> FEATURE:
<223> OTHER INFORMATION: KRT18 Forward Primer

<400> SEQUENCE: 11
ttctgggggc atgagcttca c                                      21

<210> SEQ ID NO 12
<211> LENGTH: 18
<212> TYPE: DNA
<213> ORGANISM: Artificial Sequence
<220> FEATURE:
<223> OTHER INFORMATION: KRT18 Reverse Primer

<400> SEQUENCE: 12
gcgcctgcat agacgctg                                          18

<210> SEQ ID NO 13
<211> LENGTH: 20
<212> TYPE: DNA
<213> ORGANISM: Artificial Sequence
<220> FEATURE:
<223> OTHER INFORMATION: KRT8 Forward Primer

<400> SEQUENCE: 13
gctggccgta aactgctttg                                        20
```

```
<210> SEQ ID NO 14
<211> LENGTH: 20
<212> TYPE: DNA
<213> ORGANISM: Artificial Sequence
<220> FEATURE:
<223> OTHER INFORMATION: KRT8 Reverse Primer

<400> SEQUENCE: 14
acatttggca gccagctttg                                               20

<210> SEQ ID NO 15
<211> LENGTH: 20
<212> TYPE: DNA
<213> ORGANISM: Artificial Sequence
<220> FEATURE:
<223> OTHER INFORMATION: EPCAM Forward Primer

<400> SEQUENCE: 15
gctggccgta aactgctttg                                               20

<210> SEQ ID NO 16
<211> LENGTH: 20
<212> TYPE: DNA
<213> ORGANISM: Artificial Sequence
<220> FEATURE:
<223> OTHER INFORMATION: EPCAM Reverse Primer

<400> SEQUENCE: 16
acatttggca gccagctttg                                               20

<210> SEQ ID NO 17
<211> LENGTH: 20
<212> TYPE: DNA
<213> ORGANISM: Artificial Sequence
<220> FEATURE:
<223> OTHER INFORMATION: CDH1 Forward Primer

<400> SEQUENCE: 17
taccctggtg gttcaagctg                                               20

<210> SEQ ID NO 18
<211> LENGTH: 20
<212> TYPE: DNA
<213> ORGANISM: Artificial Sequence
<220> FEATURE:
<223> OTHER INFORMATION: CDH1 Reverse Primer

<400> SEQUENCE: 18
cctgaccctt gtacgtggtg                                               20

<210> SEQ ID NO 19
<211> LENGTH: 20
<212> TYPE: DNA
<213> ORGANISM: Artificial Sequence
<220> FEATURE:
<223> OTHER INFORMATION: LGR5 Forward Primer

<400> SEQUENCE: 19
ctcccaggtc tggtgtgttg                                               20

<210> SEQ ID NO 20
<211> LENGTH: 20
<212> TYPE: DNA
<213> ORGANISM: Artificial Sequence
<220> FEATURE:
<223> OTHER INFORMATION: LGR5 Reverse Primer
```

```
<400> SEQUENCE: 20
gctcgcaatg acagtgtgtg                                          20

<210> SEQ ID NO 21
<211> LENGTH: 20
<212> TYPE: DNA
<213> ORGANISM: Artificial Sequence
<220> FEATURE:
<223> OTHER INFORMATION: CTNNB Forward Primer

<400> SEQUENCE: 21
agcaatttgt ggaggggtc                                           20

<210> SEQ ID NO 22
<211> LENGTH: 20
<212> TYPE: DNA
<213> ORGANISM: Artificial Sequence
<220> FEATURE:
<223> OTHER INFORMATION: CTNNB Reverse Primer

<400> SEQUENCE: 22
agcagctgca caaacaatgg                                          20

<210> SEQ ID NO 23
<211> LENGTH: 20
<212> TYPE: DNA
<213> ORGANISM: Artificial Sequence
<220> FEATURE:
<223> OTHER INFORMATION: CD44 Forward Primer

<400> SEQUENCE: 23
agcaccattt caaccacacc                                          20

<210> SEQ ID NO 24
<211> LENGTH: 20
<212> TYPE: DNA
<213> ORGANISM: Artificial Sequence
<220> FEATURE:
<223> OTHER INFORMATION: CD44 Reverse Primer

<400> SEQUENCE: 24
gcagtggtgc catttctgtc                                          20

<210> SEQ ID NO 25
<211> LENGTH: 21
<212> TYPE: DNA
<213> ORGANISM: Artificial Sequence
<220> FEATURE:
<223> OTHER INFORMATION: PGC Forward Primer

<400> SEQUENCE: 25
tgtctttggg ggtgtggata g                                        21

<210> SEQ ID NO 26
<211> LENGTH: 24
<212> TYPE: DNA
<213> ORGANISM: Artificial Sequence
<220> FEATURE:
<223> OTHER INFORMATION: PGC Reverse Primer

<400> SEQUENCE: 26
atgaggaact cttcaatgcc aatc                                     24

<210> SEQ ID NO 27
```

```
<211> LENGTH: 20
<212> TYPE: DNA
<213> ORGANISM: Artificial Sequence
<220> FEATURE:
<223> OTHER INFORMATION: MUC6 Forward Primer

<400> SEQUENCE: 27
cagctcaaca aggtgtgtgc                                               20

<210> SEQ ID NO 28
<211> LENGTH: 20
<212> TYPE: DNA
<213> ORGANISM: Artificial Sequence
<220> FEATURE:
<223> OTHER INFORMATION: MUC6 Reverse Primer

<400> SEQUENCE: 28
tggggaaagg tctcctcgta                                               20

<210> SEQ ID NO 29
<211> LENGTH: 20
<212> TYPE: DNA
<213> ORGANISM: Artificial Sequence
<220> FEATURE:
<223> OTHER INFORMATION: MUC5AC Forward Primer

<400> SEQUENCE: 29
ggaggtgccc acttctcaac                                               20

<210> SEQ ID NO 30
<211> LENGTH: 19
<212> TYPE: DNA
<213> ORGANISM: Artificial Sequence
<220> FEATURE:
<223> OTHER INFORMATION: MUC5AC Reverse Primer

<400> SEQUENCE: 30
cttcaggcag gtctcgctg                                                19

<210> SEQ ID NO 31
<211> LENGTH: 20
<212> TYPE: DNA
<213> ORGANISM: Artificial Sequence
<220> FEATURE:
<223> OTHER INFORMATION: CHGA Forward Primer

<400> SEQUENCE: 31
ccaaggagag ggcacatcag                                               20

<210> SEQ ID NO 32
<211> LENGTH: 20
<212> TYPE: DNA
<213> ORGANISM: Artificial Sequence
<220> FEATURE:
<223> OTHER INFORMATION: CHGA Reverse Primer

<400> SEQUENCE: 32
tcttccaccg cctctttcag                                               20

<210> SEQ ID NO 33
<211> LENGTH: 20
<212> TYPE: DNA
<213> ORGANISM: Artificial Sequence
<220> FEATURE:
<223> OTHER INFORMATION: ATP4b Forward Primer

<400> SEQUENCE: 33
```

-continued

```
tgggtgtgga tcagcctgta                                             20

<210> SEQ ID NO 34
<211> LENGTH: 20
<212> TYPE: DNA
<213> ORGANISM: Artificial Sequence
<220> FEATURE:
<223> OTHER INFORMATION: ATP4b Reverse Primer

<400> SEQUENCE: 34
ctggtcttgg tagtccggtg                                             20

<210> SEQ ID NO 35
<211> LENGTH: 21
<212> TYPE: DNA
<213> ORGANISM: Artificial Sequence
<220> FEATURE:
<223> OTHER INFORMATION: IL-8 Forward Primer

<400> SEQUENCE: 35
acactgcgcc aacacagaaa t                                           21

<210> SEQ ID NO 36
<211> LENGTH: 21
<212> TYPE: DNA
<213> ORGANISM: Artificial Sequence
<220> FEATURE:
<223> OTHER INFORMATION: IL-8 Reverse Primer

<400> SEQUENCE: 36
attgcatctg gcaaccctac a                                           21

<210> SEQ ID NO 37
<211> LENGTH: 20
<212> TYPE: DNA
<213> ORGANISM: Artificial Sequence
<220> FEATURE:
<223> OTHER INFORMATION: TNF Forward Primer

<400> SEQUENCE: 37
tccccaggga cctctctcta                                             20

<210> SEQ ID NO 38
<211> LENGTH: 21
<212> TYPE: DNA
<213> ORGANISM: Artificial Sequence
<220> FEATURE:
<223> OTHER INFORMATION: TNF Reverse Primer

<400> SEQUENCE: 38
gagggtttgc tacaacatgg g                                           21

<210> SEQ ID NO 39
<211> LENGTH: 21
<212> TYPE: DNA
<213> ORGANISM: Artificial Sequence
<220> FEATURE:
<223> OTHER INFORMATION: sFRP1 Forward Primer

<400> SEQUENCE: 39
acgtgggcta caagaagatg g                                           21

<210> SEQ ID NO 40
<211> LENGTH: 19
<212> TYPE: DNA
```

```
<213> ORGANISM: Artificial Sequence
<220> FEATURE:
<223> OTHER INFORMATION: sFRP1 Reverse Primer

<400> SEQUENCE: 40
cagcgacacg ggtagatgg                                                    19

<210> SEQ ID NO 41
<211> LENGTH: 21
<212> TYPE: DNA
<213> ORGANISM: Artificial Sequence
<220> FEATURE:
<223> OTHER INFORMATION: sFRP2 Forward Primer 1

<400> SEQUENCE: 41
acgtgggcta caagaagatg g                                                 21

<210> SEQ ID NO 42
<211> LENGTH: 19
<212> TYPE: DNA
<213> ORGANISM: Artificial Sequence
<220> FEATURE:
<223> OTHER INFORMATION: sFRP2 Reverse Primer 1

<400> SEQUENCE: 42
cagcgacacg ggtagatgg                                                    19

<210> SEQ ID NO 43
<211> LENGTH: 19
<212> TYPE: DNA
<213> ORGANISM: Artificial Sequence
<220> FEATURE:
<223> OTHER INFORMATION: sFRP2 Forward Primer 2

<400> SEQUENCE: 43
ctggcccgac atgcttgag                                                    19

<210> SEQ ID NO 44
<211> LENGTH: 22
<212> TYPE: DNA
<213> ORGANISM: Artificial Sequence
<220> FEATURE:
<223> OTHER INFORMATION: sFRP2 Reverse Primer 2

<400> SEQUENCE: 44
gcttcacata cctttggagc tt                                                22

<210> SEQ ID NO 45
<211> LENGTH: 22
<212> TYPE: DNA
<213> ORGANISM: Artificial Sequence
<220> FEATURE:
<223> OTHER INFORMATION: sFRP3 Forward Primer 2

<400> SEQUENCE: 45
acacagactt acagggcttg at                                                22

<210> SEQ ID NO 46
<211> LENGTH: 23
<212> TYPE: DNA
<213> ORGANISM: Artificial Sequence
<220> FEATURE:
<223> OTHER INFORMATION: sFRP3 Reverse Primer 2

<400> SEQUENCE: 46
gagcccatac tcatcaagta ccg                                               23
```

<210> SEQ ID NO 47
<211> LENGTH: 19
<212> TYPE: DNA
<213> ORGANISM: Artificial Sequence
<220> FEATURE:
<223> OTHER INFORMATION: sFRP4 Forward Primer

<400> SEQUENCE: 47
cctggaacat cacgcggat                                           19

<210> SEQ ID NO 48
<211> LENGTH: 19
<212> TYPE: DNA
<213> ORGANISM: Artificial Sequence
<220> FEATURE:
<223> OTHER INFORMATION: sFRP4 Reverse Primer

<400> SEQUENCE: 48
cggcttgata gggtcgtgc                                           19

<210> SEQ ID NO 49
<211> LENGTH: 22
<212> TYPE: DNA
<213> ORGANISM: Artificial Sequence
<220> FEATURE:
<223> OTHER INFORMATION: sFRP5 Forward Primer

<400> SEQUENCE: 49
aggagtacga ctactatggc tg                                       22

<210> SEQ ID NO 50
<211> LENGTH: 19
<212> TYPE: DNA
<213> ORGANISM: Artificial Sequence
<220> FEATURE:
<223> OTHER INFORMATION: sFRP5 Reverse Primer

<400> SEQUENCE: 50
ggtcggcagg gatgtcaag                                           19

<210> SEQ ID NO 51
<211> LENGTH: 23
<212> TYPE: DNA
<213> ORGANISM: Artificial Sequence
<220> FEATURE:
<223> OTHER INFORMATION: DKK1 Forward Primer

<400> SEQUENCE: 51
ccttgaactc ggttctcaat tcc                                      23

<210> SEQ ID NO 52
<211> LENGTH: 23
<212> TYPE: DNA
<213> ORGANISM: Artificial Sequence
<220> FEATURE:
<223> OTHER INFORMATION: DKK1 Reverse Primer

<400> SEQUENCE: 52
caatggtctg gtacttattc ccg                                      23

<210> SEQ ID NO 53
<211> LENGTH: 19
<212> TYPE: DNA
<213> ORGANISM: Artificial Sequence
<220> FEATURE:

```
<223> OTHER INFORMATION: DKK2 Forward Primer

<400> SEQUENCE: 53
ctcacagatc ggcagttcg                                                    19

<210> SEQ ID NO 54
<211> LENGTH: 21
<212> TYPE: DNA
<213> ORGANISM: Artificial Sequence
<220> FEATURE:
<223> OTHER INFORMATION: DKK2 Reverse Primer

<400> SEQUENCE: 54
atgccagtcc ttggtacatg c                                                 21

<210> SEQ ID NO 55
<211> LENGTH: 20
<212> TYPE: DNA
<213> ORGANISM: Artificial Sequence
<220> FEATURE:
<223> OTHER INFORMATION: DKK3 Forward Primer 1

<400> SEQUENCE: 55
aggacacgca gcacaaattg                                                   20

<210> SEQ ID NO 56
<211> LENGTH: 23
<212> TYPE: DNA
<213> ORGANISM: Artificial Sequence
<220> FEATURE:
<223> OTHER INFORMATION: DKK3 Reverse Primer 1

<400> SEQUENCE: 56
ccagtctggt tgttggttat ctt                                               23

<210> SEQ ID NO 57
<211> LENGTH: 20
<212> TYPE: DNA
<213> ORGANISM: Artificial Sequence
<220> FEATURE:
<223> OTHER INFORMATION: DKK3 Forward Primer 2

<400> SEQUENCE: 57
acgagtgcat catcgacgag                                                   20

<210> SEQ ID NO 58
<211> LENGTH: 20
<212> TYPE: DNA
<213> ORGANISM: Artificial Sequence
<220> FEATURE:
<223> OTHER INFORMATION: DKK3 Reverse Primer 2

<400> SEQUENCE: 58
gcagtccctc tggttgtcac                                                   20

<210> SEQ ID NO 59
<211> LENGTH: 21
<212> TYPE: DNA
<213> ORGANISM: Artificial Sequence
<220> FEATURE:
<223> OTHER INFORMATION: DKK4 Forward Primer

<400> SEQUENCE: 59
acggactgca ataccagaaa g                                                 21
```

<210> SEQ ID NO 60
<211> LENGTH: 21
<212> TYPE: DNA
<213> ORGANISM: Artificial Sequence
<220> FEATURE:
<223> OTHER INFORMATION: DKK4 Reverse Primer

<400> SEQUENCE: 60
cgttcacaca gagtgtccca g                                              21

<210> SEQ ID NO 61
<211> LENGTH: 21
<212> TYPE: DNA
<213> ORGANISM: Artificial Sequence
<220> FEATURE:
<223> OTHER INFORMATION: DKKL1 Forward Primer

<400> SEQUENCE: 61
ctctaccctg gtgatcccct c                                              21

<210> SEQ ID NO 62
<211> LENGTH: 22
<212> TYPE: DNA
<213> ORGANISM: Artificial Sequence
<220> FEATURE:
<223> OTHER INFORMATION: DKKL1 Reverse Primer

<400> SEQUENCE: 62
cgaagcaggt tacctttcag ga                                             22

<210> SEQ ID NO 63
<211> LENGTH: 23
<212> TYPE: DNA
<213> ORGANISM: Artificial Sequence
<220> FEATURE:
<223> OTHER INFORMATION: USAG1 Forward Primer

<400> SEQUENCE: 63
gccatcagag atgtatttgg tgg                                            23

<210> SEQ ID NO 64
<211> LENGTH: 21
<212> TYPE: DNA
<213> ORGANISM: Artificial Sequence
<220> FEATURE:
<223> OTHER INFORMATION: USAG1 Reverse Primer

<400> SEQUENCE: 64
gtgctcccta actggattgg a                                              21

<210> SEQ ID NO 65
<211> LENGTH: 22
<212> TYPE: DNA
<213> ORGANISM: Artificial Sequence
<220> FEATURE:
<223> OTHER INFORMATION: WIF1 Forward Primer

<400> SEQUENCE: 65
tctccaaaca cctcaaaatg ct                                             22

<210> SEQ ID NO 66
<211> LENGTH: 19
<212> TYPE: DNA
<213> ORGANISM: Artificial Sequence
<220> FEATURE:
<223> OTHER INFORMATION: WIF1 Reverse Primer

```
<400> SEQUENCE: 66
gacactcgca gatgcgtct                                                    19

<210> SEQ ID NO 67
<211> LENGTH: 21
<212> TYPE: DNA
<213> ORGANISM: Artificial Sequence
<220> FEATURE:
<223> OTHER INFORMATION: BARX1 Forward Primer

<400> SEQUENCE: 67
ttccacgccg gacagaatag a                                                 21

<210> SEQ ID NO 68
<211> LENGTH: 20
<212> TYPE: DNA
<213> ORGANISM: Artificial Sequence
<220> FEATURE:
<223> OTHER INFORMATION: BARX1 Reverse Primer

<400> SEQUENCE: 68
agtaagctgc tcgctcgttg                                                   20

<210> SEQ ID NO 69
<211> LENGTH: 19
<212> TYPE: DNA
<213> ORGANISM: Artificial Sequence
<220> FEATURE:
<223> OTHER INFORMATION: TFF2 Forward Primer

<400> SEQUENCE: 69
cggggagtga gaaaccctc                                                    19

<210> SEQ ID NO 70
<211> LENGTH: 21
<212> TYPE: DNA
<213> ORGANISM: Artificial Sequence
<220> FEATURE:
<223> OTHER INFORMATION: TFF2 Reverse Primer

<400> SEQUENCE: 70
cactggagtc gaaacagcat c                                                 21

<210> SEQ ID NO 71
<211> LENGTH: 23
<212> TYPE: DNA
<213> ORGANISM: Artificial Sequence
<220> FEATURE:
<223> OTHER INFORMATION: GAPDH Forward Primer

<400> SEQUENCE: 71
ggtatcgtgg aaggactcat gac                                               23

<210> SEQ ID NO 72
<211> LENGTH: 23
<212> TYPE: DNA
<213> ORGANISM: Artificial Sequence
<220> FEATURE:
<223> OTHER INFORMATION: GAPDH Reverse Primer

<400> SEQUENCE: 72
atgccagtga gcttcccgtt cag                                               23

<210> SEQ ID NO 73
<211> LENGTH: 31
```

```
<212> TYPE: DNA
<213> ORGANISM: Artificial Sequence
<220> FEATURE:
<223> OTHER INFORMATION: rDNA 16s H.pylori Forward Primer

<400> SEQUENCE: 73
tttgttagag aagataatga cggtatctaa c                                31

<210> SEQ ID NO 74
<211> LENGTH: 28
<212> TYPE: DNA
<213> ORGANISM: Artificial Sequence
<220> FEATURE:
<223> OTHER INFORMATION: rDNA 16s H.pylori Reverse Primer

<400> SEQUENCE: 74
cataggattt cacacctgac tgactatc                                    28

<210> SEQ ID NO 75
<211> LENGTH: 19
<212> TYPE: DNA
<213> ORGANISM: Artificial Sequence
<220> FEATURE:
<223> OTHER INFORMATION: gDNA hGAPDH Forward Primer

<400> SEQUENCE: 75
gacttcaaca gcgacaccc                                              19

<210> SEQ ID NO 76
<211> LENGTH: 25
<212> TYPE: DNA
<213> ORGANISM: Artificial Sequence
<220> FEATURE:
<223> OTHER INFORMATION: gDNA hGAPDH Reverse Primer

<400> SEQUENCE: 76
agaagatgaa aagagttgtc agggc                                       25
```

GENERATION, PROLIFERATION AND EXPANSION OF EPITHELIAL CELLS FROM PRIMARY TISSUE INTO MUCOSOID CULTURES

CROSS REFERENCE TO RELATED APPLICATION

This application is a 35 U.S.C. 371 National Phase Entry Application from PCT/EP2019/051287, filed Jan. 18, 2019, which claims the benefit of European Patent Application No. 18152395.2 filed on Jan. 18, 2018 and European Application No. 18157173.8 filed Feb. 16, 2018, the disclosures of which are incorporated herein in their entirety by reference.

The instant application contains a Sequence Listing which has been submitted via EFS-Web and is hereby incorporated by reference in its entirety. Said Sequence Listing, created on Jan. 18, 2018, is named 2923-1362_Sequence_Listing.TXT and is 18 kilobytes in size.

SUMMARY OF THE INVENTION

Subject of the invention is a method for long-term culture of columnar epithelial cells and the application thereof. The cells in culture survive more than 6 months and they can be expanded due to their regenerative capacity. The epithelial cells are seeded on a thin matrix-coated solid semi-permeable filter and cultivated in an air liquid interface to form a coherent monolayer. The cultivation method allows for the regeneration and expansion of the culture by enzymatic removal of the cells from the filters and seeding on a new filter. The proliferation, longevity and regenerative capacity of the cells rely on the maintenance of the stem cell niche in vitro. The stem cells are capable of multi-lineage differentiation. The cultures are sensitive to morphogens and grow factors that are inducing proliferation and/or differentiation into the specific cell lineages typical of the healthy tissue of origin. Specialized cell lineages maintain their function of origin also in the culture of the invention. By mimicking a pathological condition in the cultures of the invention, the distribution of the cells in the specific cell lineages can be altered and other lineages that are not typical of the tissue of origin may emerge (e.g. Metaplasia, neoplasia). Cultured cells of the invention maintain features of the tissue of origin including height and polarization. Polarization segregates the apical side from the basal side wherein the basal side is adjacent to the semi-permeable surface of the filter and in contact with the culture medium. The cells of the culture of invention are producing and accumulating mucus on the apical side. The apical and the basal side of the cells represent two different locations where the epithelial cells can conduct their secretory and absorptive function. The combination of these two functions may result in an active transport of substances form the apical to the basal side or vice-versa.

The cells in the culture are able to respond to a variety of stimuli. The stimulus can be applied in the culture at the apical, basal or both sides. Result of the stimulation may be the activation of a specific signaling pathway that would promote the transcription of genes involved in a specific cellular function (e.g. regulation in: inflammation, differentiation, proliferation, migration, metabolism, transport, secretion, absorption and others). The stimulus can be of various sources including physical stimulation (e.g., heat, electromagnetic radiation, contact and others) chemical stimulation (e.g. natural or synthetic molecules) or biological stimulation (e.g., whole or part of organisms such as gamete, zygotes, embryos, bacteria, viruses or parasites).

Other types of non-epithelial cells can be co-cultured. For example, stromal cells isolated from the same tissue can be co-cultivated below the epithelium or below the porous filters support in the same vessel reproducing the complexity of the whole mucosa. Similarly, cells of the hematopoietic lineage can be co-cultivated within or below the epithelium or below the porous filters support.

We name the epithelial culture of the invention "mucosoid culture", in reference to the fact that they recapitulate key characteristics of the polarized, mucus-secreting epithelial layers and they can optionally include other cells from the mucosa.

The cultures originate from explanted epithelial cells and columnar epithelial cells. The epithelial cells can be derived from primary cells isolated from any embryonic or adult vertebrate, preferentially mammalian or human tissue; alternatively, the cell can be derived from other types of epithelial cultures that allow maintenance of stem cells in vitro, preferentially organoids or planar feeder supported culture. Cells prior cultivation into mucosoid culture can be genetically modified (e.g., using recombinant nucleic acids). The mucosoid culture of this invention can also be derived from other types of non-epithelial cells, providing they have been transformed or re-programmed to become epithelial cells, reminiscent to the authentic cells described in this invention. For example, fibroblasts can be converted into induced pluripotent cells (iPS) and the re-differentiated to form polarized epithelial cells. While the induction of pluripotency and the process of redifferentiation are not the topics of this invention, however, the outcome of the redifferentiation process, i.e. the epithelial cells, is part of the invention providing they are used as mucosoid cultures, as described herein.

The mucosoid cultures are a source of mucus, cells and substances secreted in the culture medium. Analysis or direct use of these tree components, as a result of the mucosoid cultivation or of the stimulation of the mucosoid cultures, is part of this invention.

The established mucosoid cultures serve a variety of purposes, including (i) the long-term maintenance or amplification of epithelial cells used in this invention, (ii) the exploration of the behavior of the cells in response to extrinsic stimuli, (iii) the transport of substances or factors from apical to basolateral directions, or vice versa, or the translation of biological, chemical and physical signals arriving from either direction, (iv) their usage as a production tool or factory for biological factors useful for technical and medical purposes, (v) their usage as an apical platform to facilitate and reproduce various extracorporeal biological processes, (vi) their usage in more complex biological settings with additional cell populations beyond the semi-permeable filter to reproduce various intracorporeal processes, and (vii) human diagnostic or therapeutic applications.

BACKGROUND

The lining of cavities and organs in the animal body is protected by a continuous layer of cells constituting different type of epithelia. The shape of the epithelial cells can be rather squamous, cuboidal or columnar and they can be arranged as a simple layer or in a stratified manner. The simple columnar epithelia are typical of the digestive tract (stomach, small intestine, colon, rectum, gallbladder), the female reproductive tract (endocervix, endometrium, fallopian tube) and the male reproductive tract (ejaculatory duct, bulbourethral glands). The simple columnar epithelium (monolayer) can have both a secretory and an absorptive function. The simple secretory columnar epithelium provides a protective function like all other epithelia but it is in addition specialized to secrete mucins beyond the apical surface of the epithelium. Mucins are a family of large glyocproteins that are dominated by their carbohydrate moiety. The freshly synthetized material is stored in large secretory granules in the apical part of the cytoplasm and released into the extracellular space through the fusion of secretory vesicles with the plasma membrane. Once secreted, the mucins are hydrated, causing them to swell, forming an unstirred layer of mucus on the epithelial surface. Mucus lubricates, moistens, and protects the surface it bathes. Absorptive cells are equipped with hair-like cytoplasmic surface projections, microvilli that increase the absorptive surface of these cells. Microvilli are relatively rigid, non-motile, measure approximately 1 micrometer in length. Columnar epithelia, especially from the fallopian tube, can be equipped with cilia, which are structures used to move mucus and other substances as well as propel gametes and embryos in the female genital tract. Recent advancement in the stem cell biology has made possible to generate organoid from different epithelial tissues as a way of maintaining adult stem cells in vitro. Although the organoids improved the general understanding of the epithelial biology and are also use for testing drugs or chemical compounds, their spherical structure and the typical polarization make it difficult to the access of the apical side and substantially limit the analysis of any apically cell secreted compound. A solution to this problem is to build a polarized monolayer on a permeable filter that is fed only from medium provided basally and that is exposed to air on the apical side. The epithelium would be able to protect the apical surface by secreting and accumulating mucins. The epithelium would keep its regenerative capacity and allow expansion of the culture to obtain a larger number of cells.

RELEVANT LITERATURE RELATED TO THE INVENTION

Past literature reports various methods for cultivating different types of primary epithelial cells including columnar epithelial cells from mammalian species. For example Nossol et al. (2011) [1] describe air-liquid interface cultures of intestinal porcine epithelial cells. Yokoyama et al. (2007) [2] describe differentiation of gastric mucous cells induced by air-liquid interface by cultivation in a collagen gel. The described methods refer to cultures which do not have regenerative capacity, and epithelial cells cannot be expanded using those methods.

Ootani et al. (2003) [3] disclose foveolar differentiation of mouse gastric mucosa in vitro. Mouse gastric epithelial cells were co-cultured in a three-dimensional collagen gel system, and the reconstructed mucosal surface was treated with an air-liquid interface. US 2014/0302491 discloses a method for long-term culture of mammalian organoids obtained from mammalian tissue by culture in a collagen gel with an air-liquid interface. These described methods refer to culture which do not form a coherent monolayer of cells and are embedded in abundant extracellular matrix impairing the analysis of mucus or other secreted factors.

Definitions

In the following descriptions, a number of conventional terms are use. To provide a better understanding, the following definitions are provided 1. The term "cell culture" or "culture" includes the maintenance of cells in an artificial in vitro environment. In addition, the term "culture" encompasses the cultivation not only of epithelial cells, but of entire tissue and the supporting mucosal cells.

2. An 'epithelial cell culture' as meant in this invention is derived from one or more epithelial cells capable of forming a coherent monolayer of highly polarized epithelial cells on the surface of a semi-permeable filter (see definition of semi-permeable filter).

3. The term "culture method" or "culture system" refers to a specific protocol followed for a "cell culture".

4. The term "mucosoid culture" refers to the "culture method" described in this invention.

5. The term "passage" and the verb "passaging" indicate the result or the action of the enzymatic removal of the cells from one semi-permeable surface or filter (see semi-permeable surface) and re-seeding on multiple semi-permeable surfaces or filters.

6. The term "air-liquid interface" (ALI) is the interface to which the cells are exposed in the "mucosoid culture". The air-liquid interface condition can be established when only the basal side of the cells is in contact with the culture medium used in the method of the invention. The culture medium is provided only from one side, in particular from the side of the surface opposite to where the cells are located. The other side is the atmospherically condition of the cell-incubator. The apical poles of the cells (see polarization) in a mucosoid culture are covered only by fluids and factors released from their apical surface such as mucus (see mucus). The released fluid materials then contact a humid atmosphere to form an air-liquid interface.

7. The term 'polarization' of the epithelial cells of a culture means that the cells exhibit an apical pole with an apical cell surface and a basolateral pole with basolateral surfaces. The two poles have pronounced distinct features and differentially expressed markers. The apical side and the basal side of contiguous cells are separated by cell junctions. A typical apical tight junction marker is occludin. The extreme distances of the two pole surfaces define the minimal degree of cell polarization of the epithelial cell culture.

8. "Cell orientation": In the epithelial cell culture according to this invention, the polarized cells are oriented with their basolateral pole towards one side of the semi-permeable filter on which they have been placed onto.

9. "Semi-permeable surface" or "Semi-permeable solid surface" includes material found in supports that are also known as "transwell permeable support" or "culture plate inserts". It can be made typically by polycarbonate, polyethylene terephthalate or polytetrafluoroethylene. In particular, the pore size suitable for the mucosoid culture of the invention is big enough to preserve the contact of the liquid with the basal side of the mucosoid culture, but small enough to prevent the cells to migrate through it. Therefore, extrinsic factors such as small molecules or biological substances can be functionally assessed from either side or both the apical and basolateral sides of the mucosoids. In the text, the word "filter" is used as a synonym.

10. The term "organoid" is used to mean a 3-dimensional growth of mammalian cells in culture that retains features of the tissue in vivo. Contrary to the "mucosoid culture", the organoids are embedded in an extra cellular matrix and they do not form a continuous epithelium, but rather separate three-dimensional structures.

11. The term "monolayer" means that the cells are not stratifying, in particular under the standard cultivation condition described herein. The cells of the invention in the monolayer are adjoining and they form a coherent monolayer.

12. The term "coherent monolayer" is referring to the condition of the cells in the epithelium of the mucosoid culture: every epithelial cell is in direct or indirect contract, through other cells, to any cell of the mucosoid culture. The cells are therefore adjoining. Synonyms are "continuous" or "contiguous" epithelial monolayer.

13. The term "columnar epithelium" refers to the simple columnar epithelium as a type of epithelium that is not stratified, not squamous and not cuboidal.

14. "Stem cells" refer to yet another essential feature of the mucosoid culture of this invention. The stem cells have the ability of self-renewal and of generating cell progeny with specific functions. Notably, an induction of cell differentiation may lead to a termination of the regenerative capacity of the mucosoid culture. Therefore, although the ability to undergo differentiation is a hallmark of this invention, the cell differentiation may be on the cost of the regenerative capacity (see definition of regenerative capacity) of the mucosoid culture.

15. The "regenerative capacity" or "stemness" of the epithelial cell culture means that a starting cell of an epithelial cell culture or that in an established epithelial cell culture a sufficient number of cells possesses the ability to undergo several rounds of cell division. An essential feature of the mucosoid culture of this invention is that it maintains a sufficient relative number of such regenerative cells so that the culture can be expanded and is long-lived, as further described in this invention. "Regeneration", as used herein, relates (1) to the capacity of a cell to regenerate itself. Without wishing to be bound by theory, this can be due to the stemness potential that is maintained, and which allows expansion of the cells in culture. "Regeneration", as used herein, also relates (2) to the capacity of epithelial cells of regenerating a polarized epithelial monolayer, if, for example an epithelial cell is isolated, for example from an organ. Epithelial cells can form an epithelial monolayer in our body. After isolation of those cells, the original polarized monolayer can be lost. With the cultivation method of the present invention, as described herein, we can "regenerate" the epithelial monolayer in vitro. This is due to the cultivation format of the present invention, as described herein, that allows polarization of cells. In the method of the invention, as described herein, regeneration of (1) and (2) can be combined, and we can generate or/and regenerate polarizes epithelial monolayers.

16. By "induced stem cells", it is referred to the technology by which it is possible to obtain a pluripotent stem cell from a somatic cell and to re-differentiate this into an adult organ specific epithelial cell.

17. "Lineages" are all the possible function specific epithelial cells found in one organ. For example, the parietal cells are the cells producing acid in the stomach; the ciliated cells are the one in the fallopian tube for the propulsion of gametes or embryos.

18. "Mucus" refers to all the apically accumulated proteins and compounds from the epithelium, including the mucins.

19. "Feeder culture" refers to a culture method where the cells of interested are co-cultured with other cells that are providing nutrients and growth factors.

20. Cell "adherence" describes the ability of a cell to attach to a surface through cell adhesion molecules that are including selectins, integrins, syndeans and cadherins.

DETAILED DESCRIPTION

1) Generation and Propagation of Columnar Epithelial Cells into Cultivable Polarized Cell Monolayers In the present invention, air-liquid interface (ALI) methodology is used to establish functional, long-lived, highly polarized columnar epithelial monolayers of healthy mammalian columnar epithelial cells which fully recapitulate the different cell lineages found in situ. We name the culture of the invention "mucosoid culture". The cells in the mucosoid cultures are long-living, and this cultivation method allow long-term regeneration and expansion of the cells in the culture by enzymatic removal of the cells from one filter and re-seeding on multiple filters. The cells of the mucosoid cultures maintain their features unaltered through the passaging. The regeneration ability relies on the preservation of the stem cells in vitro. The stem cells are preserved by providing factors in the cultivation media that are mimicking the stem cell niche in vivo. Yet another feature of the culture that enables regeneration is the high-density of the cells in the mucosoid cultures. In the mucosoid culture of the invention, the polarization of the cells reflects that observed in the organ of origin, with the apical side facing up, where mucus is accumulating, and the basal side facing the filter, where nutrients and growth factors are taken up. In relation to the organism from where the mucosoids are derived, the apical cell side resembles the extracorporeal site or space, whereas the basal side resembles the intracorporeal space or environment. Nuclei are usually localized on the basal side while E-cadherin is expressed predominantly on the basolateral side. The expression of the tight junction marker occludin is usually restricted to the apical side. From a top view, the tight junctions appear as characteristic dots connecting apically contiguous cells, forming a coherent barrier. Since epithelial barriers have a high turnover, proliferation as well as cell extrusion are equally important to preserve constant cell numbers. The epithelial cells of the mucosoid culture are able to proliferate and dying cells are ejected in the mucus layer. All the mentioned advances were obtained by combining established cultivation methods based on solid semi-permeable surfaces (for example, polycarbonate filters) [3, 4] with more recent knowledge about propagation of primary gastrointestinal cells from adult stem cells [5-8]. In the mucosoid culture of the invention, the polarized columnar epithelium of different mucosae is regenerated. In contrast to standard ALI cultures, the mucosoid ones are long-lived and can regenerate. They are stable cultures consisting of highly polarized cells comprised of all lineages and they produce and accumulate mucins on the apical side. By commonly known culture techniques, these features cannot be achieved.

A first aspect of the invention relates to a method of long term culturing epithelial cells on a solid semi-permeable surface, comprising the steps:
  (a) providing epithelial cells,
  (b) contacting the epithelial cells with a solid semi-permeable surface,
  (c) culturing the cell of (b) under air-liquid interface conditions,
  (d) obtaining the cells, the mucus and the cultivation media from the culture of (c), and
  (e) optionally, use the cell from step (d) as a source of cells for (a) and repeat steps (b), (c), and (d).

The epithelial cell provided in step (a) can be any epithelial cell. Epithelial cells suitable for mucosoid cell culture are known to the skilled person. In particular, the epithelial cells are from a columnar epithelium.

The epithelial cells of (a) can be derived from primary cells isolated from any embryonic or adult vertebrate, preferentially mammalian or human tissue; the organism of origin can be a genetically modified organism or may carry genetic constructs that are useful for test and/or cell production proposes. The organism or the tissue of origin may be healthy or diseased and in particular, the cells may carry genetic or epigenetic defects potentially connected with a pathologic state including cancer. The organism of origin may be infected with pathogens as viruses, bacteria or parasites.

The epithelial cells of (a) can be derived from a prior cultivation performed using other methods. In particular, the cells of the mucosoid cultures can derive from an organoid culture or a feeder culture comprising epithelial cells. The preparation of organoid cultures or feeder cultures of epithelial cells is known to the skilled person. Organoid and feeder cultures as a source of epithelial cells can be advantageous, if a cell culture having defined and reproducible characteristics shall be obtained by the method of the invention.

The epithelial cells of (a) derived from prior cultivations can be genetically modified or derived from genetically modified organisms; for example, cells comprising recombinant nucleic acids. Genetic modifications of the cells prior cultivation into mucosoid cultures include the insertion of genetic constructs that are useful for test and/or cell production purposes. The cells prior cultivation into mucosoid cultures may be genetically or epigenetically manipulated to mimic a condition correlated to a pathologic state. The cells prior cultivation into mucosoid cultures may be infected with pathogens such as virus, bacteria or parasites. Manipulation of the cells prior cultivation into mucosoid culture may include epithelial generated e.g. via induced pluripotent stem cells technology (iPS) and subsequentially differentiate into epithelial cells. In particular, at least some of the cells can maintain their stemness potential and regenerative potential if, for example, stem cell promoting factor are included into the cultivation medium. Examples of stem cell promoting factors are the one activating directly the b-Catenin signaling pathway like WNT family proteins or RSPO family proteins. Examples of stem cells promoting factors are also the one inhibiting the TGF-beta receptor family like Noggin. In particular, the cells maintaining their stemness potential are capable to differentiate.

In the method of the invention, cells can be seeded at confluent density onto the solid semi-permeable surface.

The degree of confluency (density) at seeding can be in the range of 50% to 100%, or can be at least 80%, at least 85%, at least 90% or at least 95%. At least 90% or at least 95% confluency at seeding are preferred. Under these conditions, the cell culture of the invention can be obtained. In the present invention, "degree of confluency" at seeding describes the percentage of the solid surface covered by cells at seeding. 50.000 to 500.000 epithelial cells per 0.6 cm$^2$ can be seeded to obtain the cell culture of the invention. The amount of cells to be seeded can depend upon the cell type.

The solid surface to which is epithelial cell can be contacted in step (b) is a semi-permeable surface which is porous. The semi-permeable surface is located within a carrier. The carrier can be located in a cell culture vessel. The culture medium within the pores is in fluid communication with the culture medium in the cell culture vessel. In a suitable arrangement, compounds can diffuse through the pores and have access to the basal surface of the cultured cell.

The semi-permeable can be a horizontal surface wherein the cells to be cultured are located on the upper surface. The culture medium within the pores is in fluid communication with the culture medium below the carrier. An exemplary embodiment is described in FIG. 1.

In particular, the pores in the porous surface have a pore size so that during cell culture, the cells do not pass through the porous surface. The pores can have a size in the range 0.2 μm to 1 μm, in particular a size of about 0.4 μm.

The surface can be any surface suitable for cell culture. In particular, the surface is a polycarbonate surface, a polycarbonate filter, a PET surface, or a PET filter. It is preferred that the surface is a polycarbonate surface, such as a polycarbonate filter.

In particular, the solid surface is coated with an agent suitable to increase the adherence of the epithelial cell. In this context, "adherence" describes the capability of a cell to be cultured to adhere to a surface, in particular a solid surface. The skilled person knows suitable agents. For example, the solid surface can be coated with collagen or Matrigel. The amount to be applied to the surface can depend upon the cell type. Cells having a larger adherence (such as gastric cells) need smaller amounts, whereas cells having a smaller adherence (such as colon cells) need larger amounts. The skilled person knows suitable conditions for the cell types as described herein.

In the present invention, the agent suitable to increase the adherence of the epithelial cell is in particular an extracellular matrix protein. The extracellular matrix protein can be of natural or synthetic origin. Preferably, the extracellular matrix protein is selected from collagen, gelatin, laminin, elastin, fibronectin, heparin sulfate, chondroitin sulfate, keratin sulfate, hyaluronic acid, gelatinous proteins from the Engelbreth-Holm mouse sarcoma cells, hydrogel and combinations thereof. A preferred extracellular matrix protein is selected from collagen and gelatinous proteins from the Engelbreth-Holm mouse sarcoma cells.

Engelbreth-Holm mouse sarcoma cells are also termed Engelbreth-Holm-Swarm (EHS) mouse sarcoma cells. "Matrigel" is the trade name of a gelatinous protein mixture secreted by EHS mouse sarcoma cells.

In the methods as described herein, the surface as described herein is coated with an extracellular matrix protein before contacting the surface with the cell. This step results in a coating of the surface.

The coating may have a thickness of 1 nm to 1 μm. Preferably the coating has a thickness of 200 to 800 nm, 200 to 500 nm or 500 to 800 nm.

A preferred coating comprising an extracellular matrix protein selected from collagen and gelatinous proteins from the Engelbreth-Holm mouse sarcoma cells, has a thickness of 1 nm to 1 μm. Preferably the coating has a thickness of 200 to 800 nm, 200 to 500 nm or 500 to 800 nm.

In particular, the culture in step (b) is performed in a liquid medium. More particular, the culture media in step (b) does not contain a 3D culture matrix, such as a basement membrane-like matrix, e.g. a Matrigel, BME or EHS matrix in an amount capable of forming a 3D culture matrix. In particular, the culture medium is essentially free of collagen, BME (basement membrane extract) and EHS secreted proteins (such as Matrigel).

The air-liquid interface of (c) starts by removing the top medium applied at step (b). The medium is removed when the seeded cells form a coherent monolayer covering the semi-permeable surface. % of coverage is from 50% to 100%, preferentially more than 90%. Incomplete coverage of the semi-permeable surface causes leakage of the medium from the lower side of the semi-permeable surface to the upper one where the cells are located. The air-liquid interface of (c) can be defined as established when the apical side of the cells is not in contact anymore with the culture medium. The air-liquid interface condition of (c) can be obtained by applying cell culture medium from the side of the surface opposite to where the cells are located. The air-liquid interface condition of (c) can be established when only the basal side of the cells is in contact with the culture medium used in the method of the invention.

The cell culture obtained at the step (d) can comprise an epithelial cell monolayer, in particular a coherent epithelial cell monolayer.

The cells resulted from a mucosoid cultures at step (d) are polarized columnar epithelial cells wherein the basal side is adjacent to the surface. The cells can be connected by tight junctions on the apical side.

In particular, during isolation of primary cells, due to the enzymatic digestion, the polarization can be lost. After one to three weeks, repolarization of the cells can be achieved.

The epithelial cells in the culture obtained at step (d) can be connected by tight junctions on the apical side.

The cells resulted from the cultures of (c) secrete and accumulate mucus on their apical side that can be harvested in step (d).

The cells resulted from the cultures of (c) secrete and accumulate molecule in the culture media that can be harvested in step (d).

The cells harvested at the step (d) can be in an active proliferative state.

The cells resulting from the cultures of (c) are stable for >6 months before the harvesting step (d).

In the present invention, the stem cells in the cell culture from (c) to (d) had multilineage differentiation potential. The stem cells can differentiate, in particular, into particular lineages specific of each tissue. Specific cell lineages are found in step (d).

In the present invention, the cells obtained in the cell culture at step (d) can exhibit stemness. In particular, some of the cells maintain their sternness potential and regenerative capacity. The epithelial cells obtained in (d) can comprise undifferentiated cells and/or cells maintaining their stemness potential.

Step (e) depends on the regenerative capacity of the culture and is obtained by enzymatic digestion and dissociation of the cells harvested in step (d). The procedures for cell dissociation are known by the skilled person.

Step (e) can be repeated more than 2 times, more than 5 times, more than 10 times or more than 20 times every 5 to 60 days, preferentially every 14 to 30 days.

The cell culture obtained by the method of the invention can be stably propagated for more than one month, for more than 3 months or for more than 6 months. The cell culture obtained by the method of the invention remains stable for up to one year or longer.

By the method of the invention, an epithelial cell culture can be obtained, reproducing the features of the in vivo phenotype of the epithelium. This cell culture can also be termed "mucosoid culture".

The epithelial cells obtained by the method of the invention can be differentiated when the WNT pathway is not activated or/and when the WNT pathway is at least partially inhibited.

The terms "WNT pathway", "WNT-b-Catenin pathway" and "b-Catenin signaling pathway" are equivalent and describe the same pathway. These terms can be used interchangeably herein.

The epithelial cells obtained by the method of the invention can be differentiated by introducing differentiation niche factors into the culture medium. Examples of differentiation niche factors are BMP family proteins, SFRP family proteins or DKK family proteins. Differentiation niche factors suitable in the present invention are described in the examples (for example, in FIG. 15).

The mucosoid cultures at the step (d) provide a source of
(i) mucus,
(ii) cells, and
(iii) secreted molecules in the cultured medium,
which can be used and/or analyzed separately according to standard methods. Analysis or direct use of these tree components, as a result of the mucosoid cultivation or of the stimulation of the mucosoid cultures, is part of this invention.

Mucus, cells, and the secreted molecule in the culture medium can be used as a source or production of substances.

Use and analysis of the mucus (i) is described in the section "Production, secretion and analysis of the mucus produced by the mucosoid cultures".

The cells of (ii) produced using the method of the invention can be used for regenerative medicine as a source of cells.

Cells of the mucosoid cultures (ii) can be analyzed by any microscopy technology prior preparation known by the skilled person.

Protein content analysis of the epithelial cells (ii) of the mucosoid culture can be performed by any protein detection technology known by the skilled person. In particular, the mucus can be analyzed by western blot or LC-mass spectrometry after protein extraction or by IF or IHC on whole mount sample or sections.

Nucleic acid from the epithelial cells of the mucosoid culture (ii) can be isolated and expression evaluated by qPCR, microarray, sequencing or other methods known by the expert person.

The secretion of factors in the medium (iii) can be analyzed by ELISA, western blot, mass spectrometry or other methods known by the expert person.

The absorption or transport can be analyzed in (i), (ii), or/and (iii), thereby providing a technology which allows the detection of the absorbed or transported molecule.

Any stimulation of the mucosoid cultures including physical stimulation (e.g., heat, electromagnetic radiation, contact and others) chemical stimulation (e.g. natural or synthetic molecules) or biological stimulation (e.g. whole or part of organisms such as gamete, zygotes, embryos, bacteria, viruses or parasites) can result in the modulation of signaling pathways that are affecting cellular functions (including inflammation, differentiation, proliferation, migration, metabolism, transport, secretion, absorption, repair). Readout of these cellular functions can be found after stimulation in the mucus in the cells or in the molecules secreted in the culture medium.

The epithelial cell provided in step (a) can be a primary epithelial cell. Example 1 describes isolation of primary gastric mucosa cells following preparation of mucosoid culture. Example 2 describes isolation of colon mucosa cells and following preparation of mucosoid culture. Example 3 describes isolation of gallbladder mucosa cell following preparation of mucosoid culture. Example 4 describes isolation of primary and fallopian tube mucosa following preparation of mucosoid culture.

Gastric epithelial cells can be seeded in a density of 150,000 to 300,000 cells per 0.6 $cm^2$, preferably 200,000-250,000 cells per 0.6 $cm^2$.

Colon epithelial cells can be seeded in a density of 250,000 to 350,000 cells per 0.6 cm$^2$, preferably 300,000 cells per 0.6 cm$^2$.

Gallbladder epithelial cells can be seeded in a density of 250,000 to 350,000 cells per 0.6 cm$^2$, preferably 300,000 cells per 0.6 cm$^2$.

Fallopian tube epithelial cells can be seeded in a density of 250,000 to 350,000 cells per 0.6 cm$^2$, preferably 300,000 cells per 0.6 cm$^2$.

Figure 2:
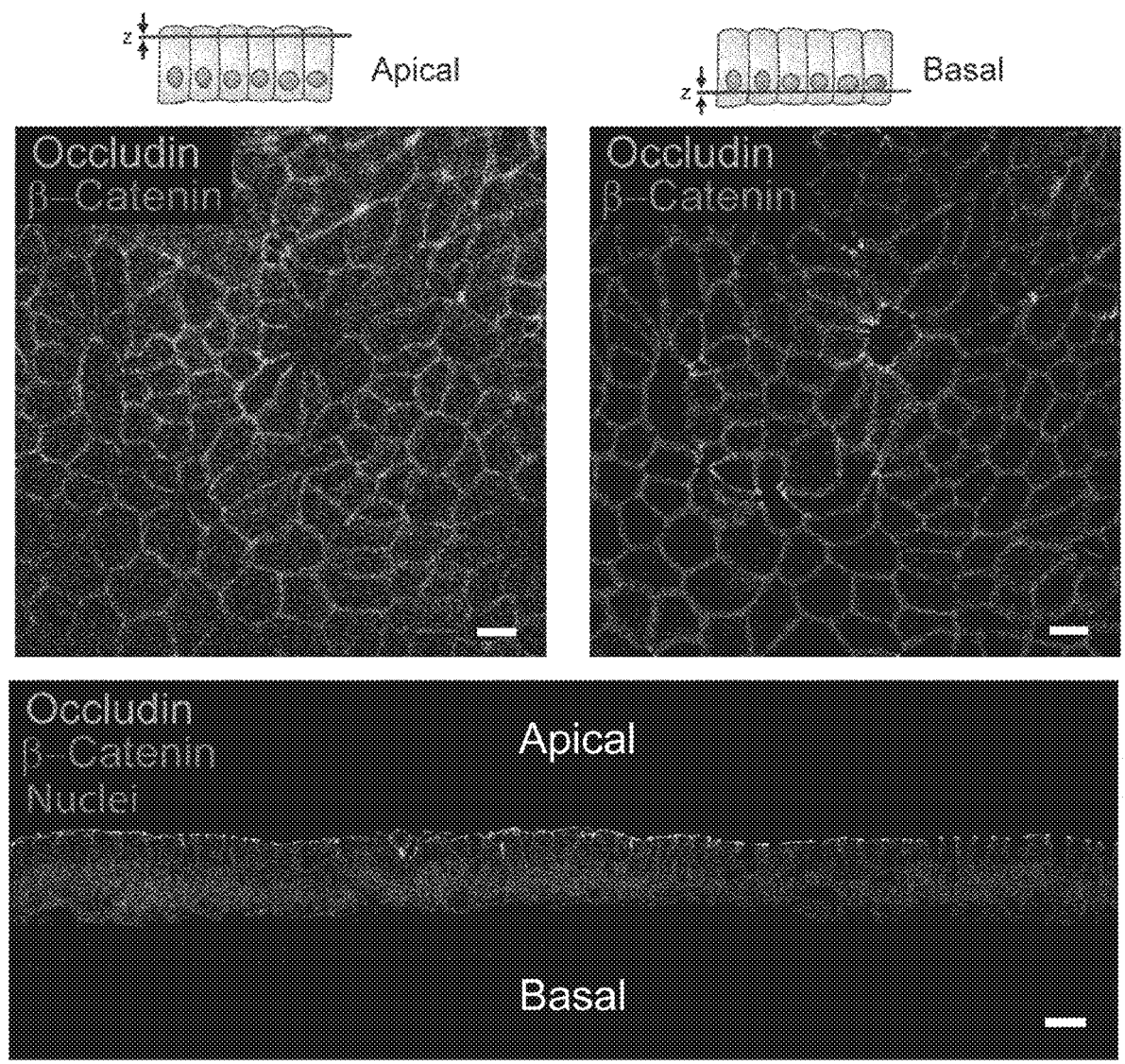

FIG. 2 shows the presence of occludin, indicating the presence of tight junctions in the cell culture of the invention.

Figure 3:
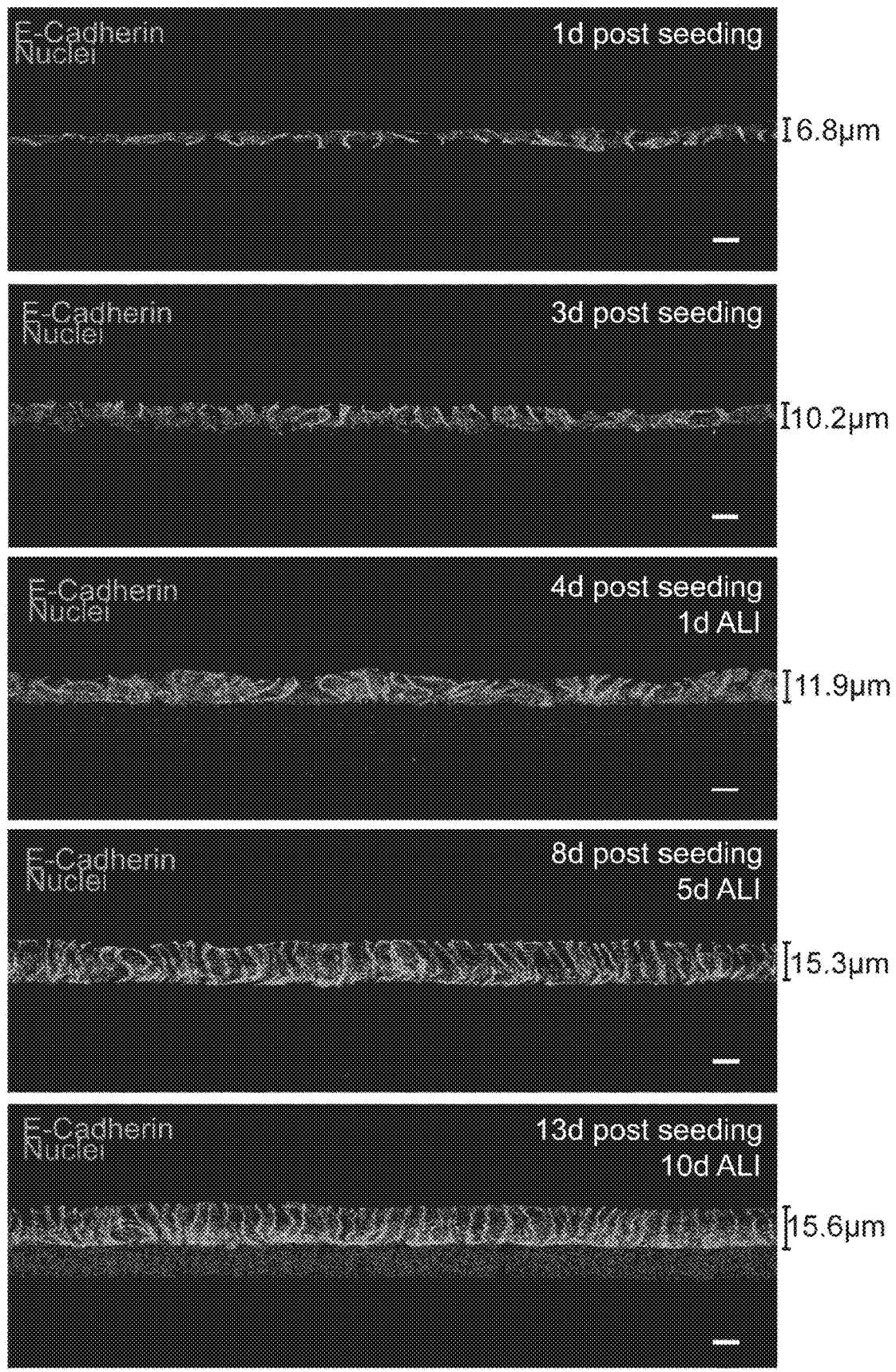

In FIG. 3, cells are seeded at confluent density onto polycarbonate filters. One day after seeding, cells have formed a confluent monolayer. In the subsequent days from 1 to 14, cells are repolarizing. Cells one day after seeding have a height <5 μM. Cells during the cultivation period are increasing their height and after 10 to 13 days and in particular after 13 days have a height of >15 μM.

Figure 4:
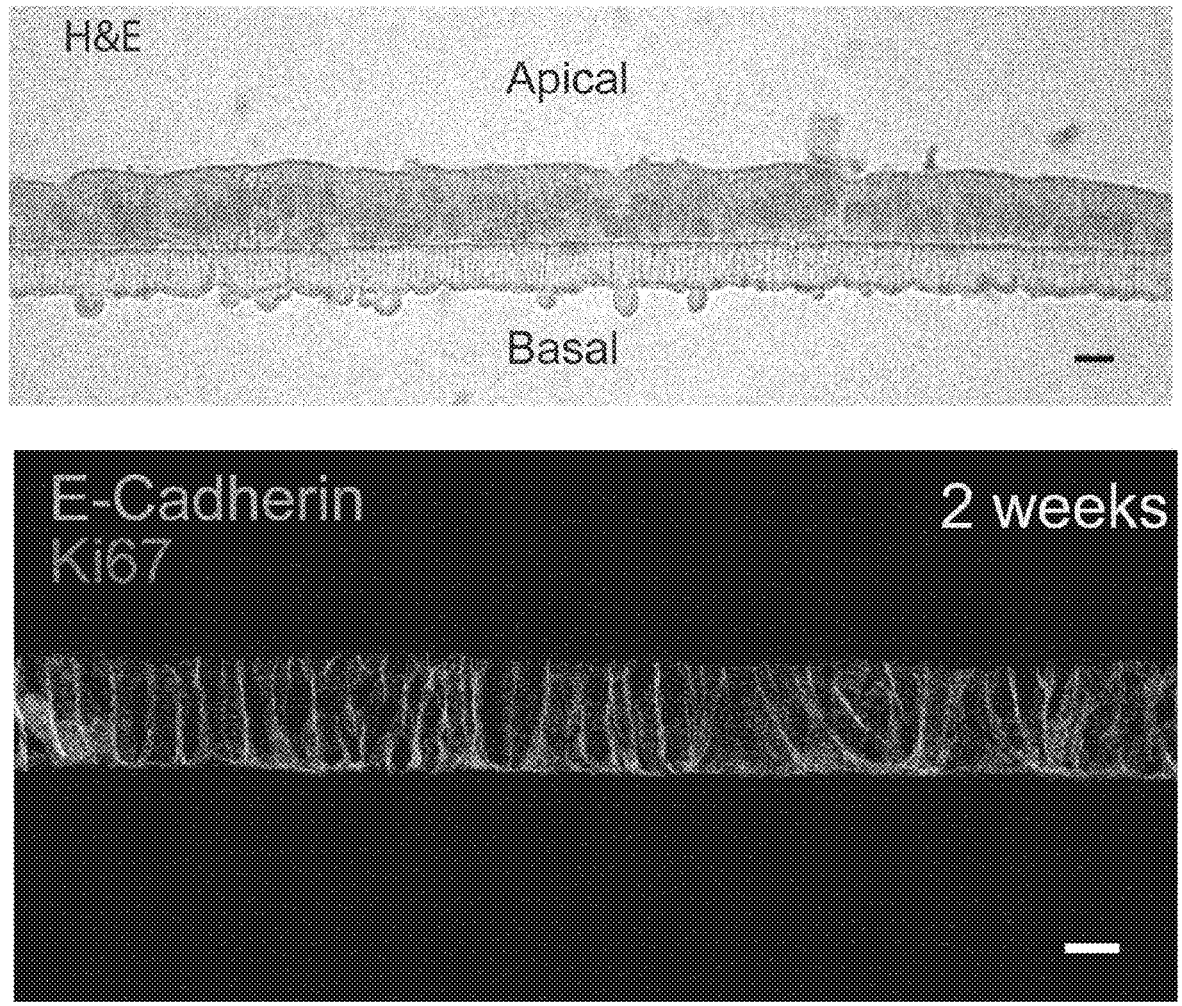
Figure 5:
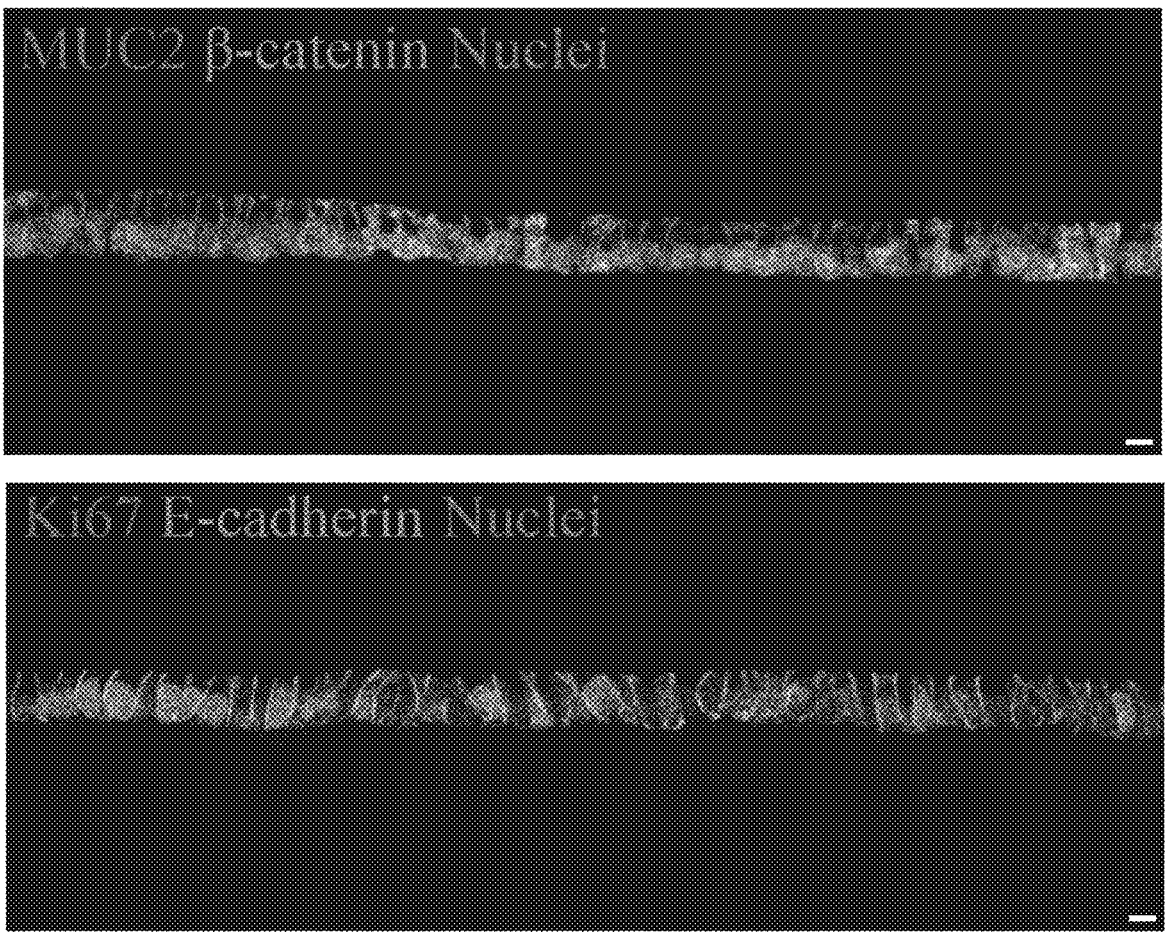
Figure 6:
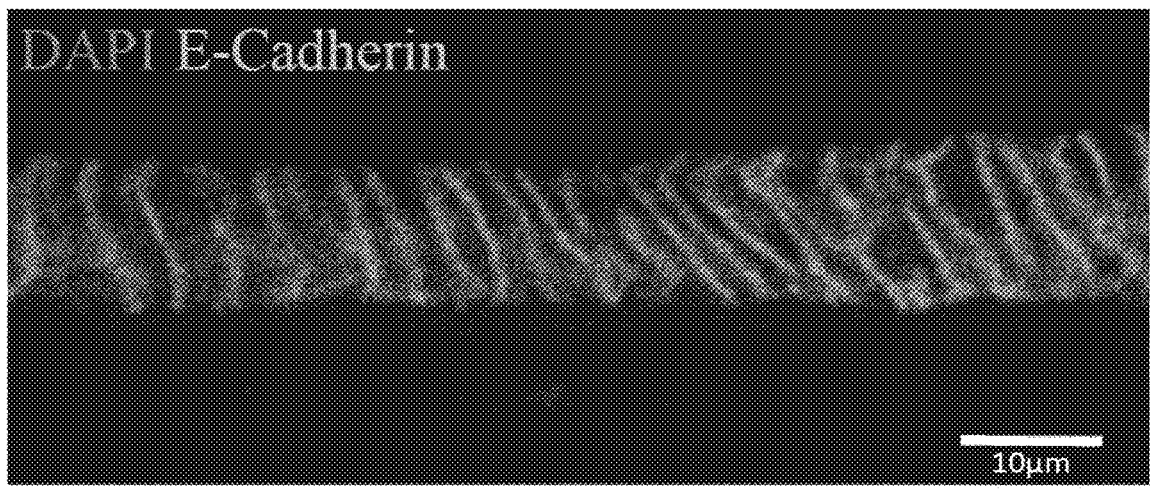
Figure 6:
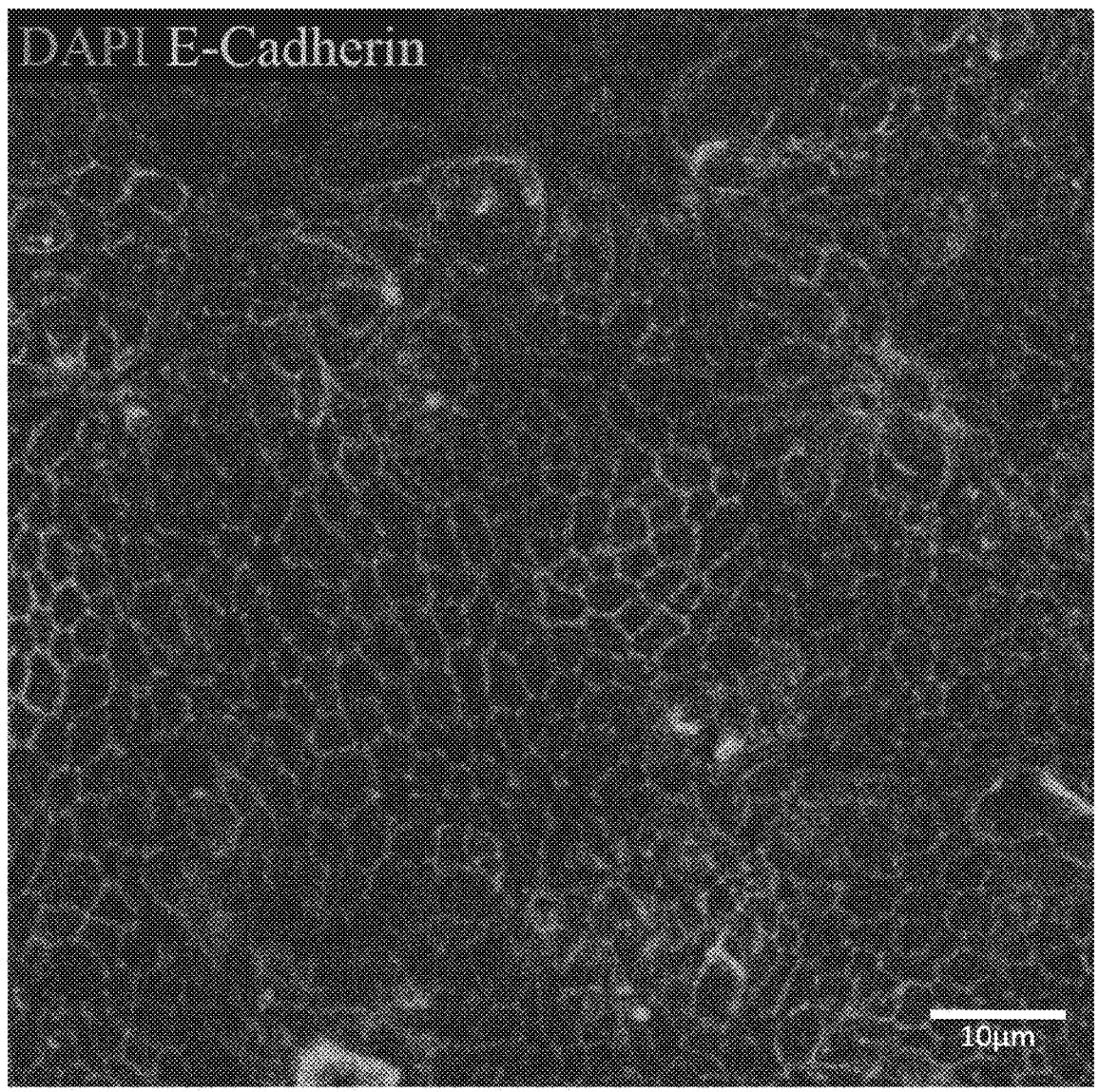
Figure 7:
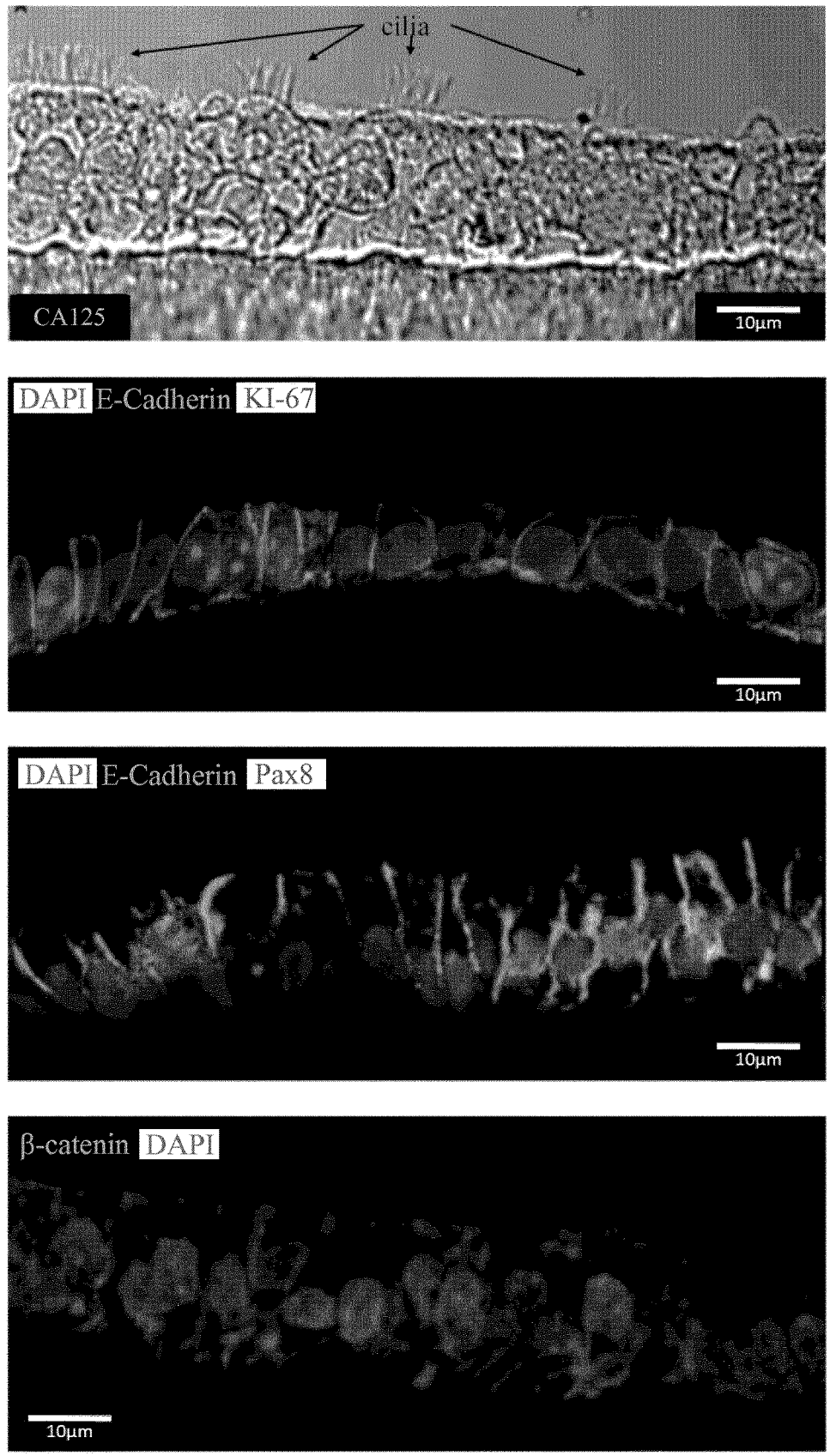

FIGS. 4 to 7 show the culture of epithelial cells by the method of invention. FIG. 4 shows the culture of gastric epithelial cells and Ki67 positive proliferating cells in the mucosoid culture. FIG. 5 shows the culture of colon epithelial cells expressing the typical colon mucin MUC2 and Ki67 proliferating cells in the mucosoid culture. FIG. 6 shows gallbladder epithelial cells in the mucosoid culture from a lateral and from a top view. FIG. 7 shows the culture of Fallopian tube epithelial cells in the mucosoid culture including ciliated cells, Ki67 positive proliferating cells, PAX8 positive stem cells and cells with activated WNT/β-Catenin pathway. Example 6 describes how to perform a test to screen bactericidal activity of the mucus produced by mucosoid cultures.

Figure 8:
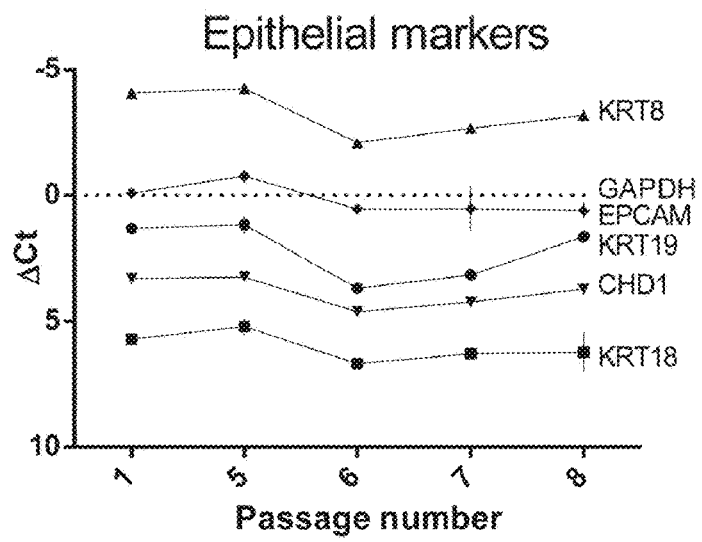
Figure 8:
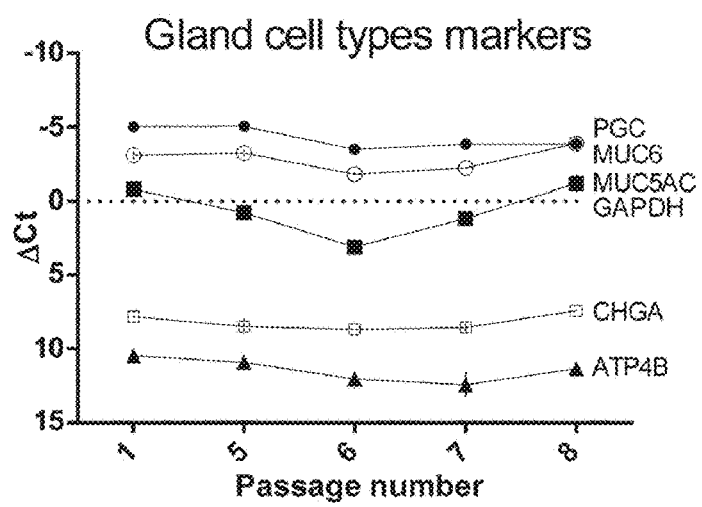
Figure 8:
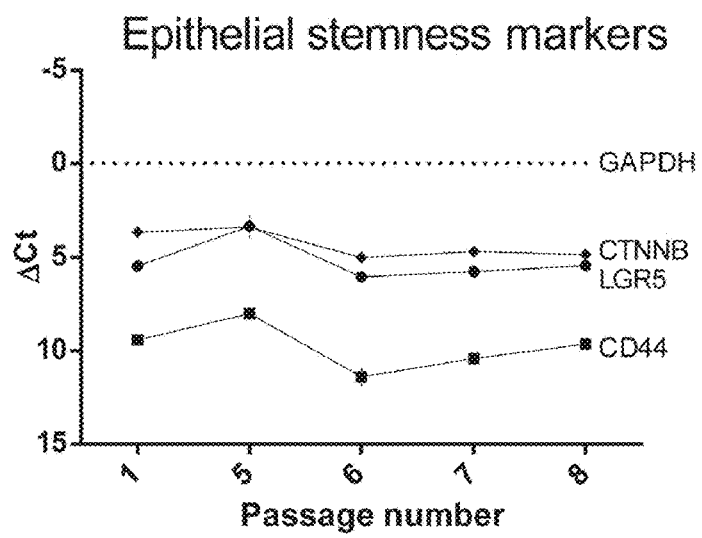

FIG. 8 shows that expression of markers of gastric cells remained stable for up to seven months, indicating that the phenotypic composition of the cells remains unchanged over time. In particular in the mucosoid culture of the stomach, EPCAM, CDH1, CTNNB, CD44 and LGR5 maintain a stable relative level of expression compared to the housekeeping gene GAPDH.

2) Production, Secretion and Analysis of the Mucus Produced by the Mucosoid Cultures In the mucosoid of the invention, freshly synthetized mucins are stored in large secretory granules in the apical half of the cytoplasm and released into the extracellular space through the fusion of secretory vesicles with the plasma membrane. Analyzing by immunofluorescence the presence of mucins in these secretory granules, it is found for example that the gastric mucosoid culture are characterize by the expression of the typical stomach mucins MUC6 and MUC5AC and the colon is instead characterize by the expression of MUC2. The mucins are secreted together with other proteins forming the mucus. In the mucosoid culture of the invention, the mucus is secreted and accumulated on the apical side and can be further analyzed. The secreted mucus prevents contact with epithelial cells constituting a barrier against bacterial or chemical insult. The robust and regulated mucus production is enabling research of important mucosal component and can provide new options for future therapeutic drug targeting. For example, compounds that can affect secretion of epithelial protein in the mucus can be screened in the mucosoid culture of the invention to test enhancement of antimicrobial activity in the mucus. These compounds can be added in the culture medium or in the apical side in direct contact with the mucus. Living pathogen, dead pathogen or portions of pathogens can be also added to the mucosoid culture to test enhancement or decrease of antimicrobial activity. Here, a method for production and analysis of mucus from the mucosoid culture is provided.

The production of mucus can comprise the following steps:
(a) providing epithelial cells,
(b) contacting the epithelial cells with a solid semipermeable surface,
(c) culturing the cell of (b) under air-liquid interface conditions,
(d) optionally administration of factors to the culture of (c) that can affect mucus composition,
(e) accumulation of the mucus on the apical surface of the culture of (c) and (d), and
(f) harvesting of the mucus accumulated in (e).

The options for the steps (a), (b) and (c) are described herein, in particular in the section "Generation and propagation of columnar epithelial cells into cultivable polarized cell monolayers". The epithelial cells obtained by the method of the invention can be differentiated by introducing differentiation niche factors into the culture medium. Examples of differentiation niche factors are BMP family proteins, SFRP family proteins or DKK family proteins. Differentiation niche factors suitable in the present invention are described in the examples (for example, in FIG. 15).

Of particular importance is the origin of the cells for the step (a). The mucus that is produce may be different if, e.g., cells are from different animals, different tissue, cells are infected or genetically modified.

The compound that affects epithelial secretion in the mucus (d) can be a small molecule, a mammalian cytokine, a mammalian genetically modified cytokine.

The compound that affects epithelial secretion in the mucus (d) can be a living organism, a genetically modified organism, a dead organism or part of a dead organism.

The compound that affects epithelial secretion in the mucus (d) can be added on the apical or on the basal side of the monolayer.

Accumulation of the apical mucus of step (e) can be performed for 12 h to >60 days, preferentially for 3 to 10 days.

The amount of mucus produced from the "mucosoid cultures" that can be harvested at step (f) varies from 5 to 50 μl each 24 h each cm$^2$ of culture.

Mucus of (f) can be used as a source or production of substances.

The mucus of (f) can be used as a medicament, as a vehicle of molecules in the organism or as an in-vitro environment for the cultivation or maintenance of organism (including gametes, embryos, bacteria, parasites).

Protein analysis of the mucus (f) can be performed by any protein detection technology known by the skilled person. In particular, the mucus can be analyzed by western blot or LC-mass spectrometry.

Biological, chemical or physical activity of the mucus (f) can also be tested. Activity refers to the possibility to measure a phenomenon after the mucus is applied, e.g. bactericidal activity, pH, density, viscoelasticity etc.

Example 5 shows a high-throughput analysis of the mucus secreted by the mucosoid cultures of the stomach and Example 6 shows an analysis of the bactericidal activity of the gastric mucus.

3) Induction of Different Epithelial Cell Lineages Inside the Mucosoid Cultures

The epithelia lining the cavity of our body are derived from epithelial residing stem cells that have the capacity to differentiate into all specialized lineages. The mucosoid culture of the invention rely on the intrinsic capacity of epithelial stem cells to differentiate into all the specialized lineages. For example, in the mucosoid culture of gastric origin, different cell types including foveolar cells, chief cells, parietal cells and enteroendocrine cells can be found. For example, in the mucosoid culture of fallopian tube origin, ciliated cells can be found. For example, in the colon derived mucosoid culture, mucus-secreting cells can be found. In the mucosoid of the invention specific cell lineages can be enriched inside the culture by varying the composition of the culture media and activating specific signaling pathways. Variation in the composition of the media consists in the administration or deprivation of specific factors that are able to activate specific cell-signaling pathways regulating differentiation. Differentiation into specific lineages might be accompanied by a drastic reduction of the stemness of the cells in the mucosoid culture, which impairs further propagation. Mimicking a pathological condition in culture (e.g. introducing a specific mutation into the cells of the cultures or using a compound which alters the physiological regulation of a specific cell signaling pathway) might result in an aberrant differentiation into lineages that are not normally resident in the tissue (e.g. metaplasia) in a neoplasia. The mucosoid culture of the invention represents therefore also a valid system to test the effect of natural or artificial compounds on stem cell differentiation and enables the cultivation of specific cell lineages.

The induction of specific epithelial cell lineages requires the following steps:
  (a) providing an epithelial cell,
  (b) contacting the epithelial cell with a solid semi-permeable surface,
  (c) culturing the cell of (b) under air-liquid interface conditions,
  (d) administration or depletion of factors to the culture of (c) that can affect the differentiation of a specific lineage, and
  (e) harvesting of the cells, mucus and culture medium of (c) and (d) and comparative analysis the proportion of the different specialized cells.

The options for the steps (a), (b) and (c) are described herein, in particular in the section "Generation and propagation of columnar epithelial cells into cultivable polarized cell monolayers"

The compound (d) of that affect epithelial differentiation can be a small molecule, a mammalian cytokine, a mammalian genetically modified cytokine. In particular, the epithelial cells are differentiated when the WNT pathway is not activated or/and when the WNT pathway is at least partially inhibited. The epithelial cells can be differentiated by introducing differentiation niche factors into the culture medium. Examples of differentiation niche factors are BMP family proteins, SFRP family proteins or DKK family proteins. Differentiation niche factors suitable in the present invention in the examples (for example, in FIG. 15).

In particular the epithelial cells obtained in step (d) of the method of the invention as described herein are differentiated when the WNT pathway is not activated or/and when the WNT pathway is at least partially inhibited. The epithelial cells obtained in step (d) can be differentiated by introducing differentiation niche factors into the culture medium. Examples of differentiation niche factors are BMP family proteins, SFRP family proteins or DKK family proteins. Differentiation niche factors suitable in the step (d) are described in the examples (for example, in FIG. 15).

The compound (d) that affects epithelial differentiation in the mucus can be a living organism, a genetically modified organism, a dead organism or part of a dead organism.

The compound (d) that affects epithelial differentiation can be added apically or basally in the culture medium. In particular, it is added apically in the mucus if the compound is expected to have an apical cellular receptor or basally in the culture medium if the opposite.

The cells, the mucus and the culture medium of (d) can be analyzed by standard methods known by the expert person.

For example, in the mucosoid culture of gastric origin, it is demonstrated that directed differentiation into foveolar or basal phenotypes can be obtained by WNT signaling modulation. Example 7 is showing how WNT3A and RSPO1 promote the lineage that is typical of the base of the gastric-antral gland and which is important to retain the stem cell niche. The foveolar and basal phenotypes reflect in the mucosoid culture the typical mucin expression pattern found in the real organ: MUC5AC is found more expressed in the foveolar type while MUC6 is found in the basal type. Deprivation of WNT3A and RSPO1 reduces the level of the stem cell marker of the stomach LGR5 and the regeneration capacity of the cultures.

For example, in the mucosoid culture of gastric origin, it is demonstrated that directed differentiation into parietal cells can be obtained by BMP pathway activation. Example 8 is showing that the BMP pathway and histamine are promoting gastric parietal cell differentiation and acid production.

4) Screen of Pro or Anti-Inflammatory Compounds Using the Mucosoid Cultures

The mucosoid cultures of the invention comprise cells of epithelial origin. Being the epithelium the first barrier that protects the organs against infection or xenobiotic substances, it has the capacity of starting and modulating an inflammatory response in concert with other cells populating or migrating inside the gastric mucosa. One of the master mediators of inflammatory response in the epithelium is the NF-kB pathway. Under a variety of stimuli including the one mediated by Toll-like receptors the P65 subunit of the NF-kB complex translocate in to the nucleus and mediate the activation of pro-inflammatory genes including chemotactic factors involved in the recruitment of cells of the innate and adaptive immune response. In the mucosoid culture of the invention, the cultured epithelial cells are responding to inflammatory stimuli, and it is possible to measure the response by analyzing the expression of the mRNA of pro or anti-inflammatory mediators or by analyzing the amount of mediators released in the culture medium. Different epithelial cell lineages as indicated in the section "Induction of different epithelial cell lineages inside the mucosoid cultures" may have different sensitivity to pro or anti-inflammatory compounds.

The test of specific pro or anti-inflammatory compounds in the mucosoid cultures requires the following steps:
  (a) providing an epithelial cell,
  (b) contacting the epithelial cell with a solid semi-permeable surface,
  (c) culturing the cell of (b) under air-liquid interface conditions,
  (d) administration of factors to the culture of (c) that can affect inflammatory response, and
  (e) harvesting of the cells, mucus and the culture medium of (d) and analysis The options for the steps (a), (b) and (c) are described herein, in particular in the section "Generation and propagation of columnar epithelial cells into cultivable polarized cell monolayers".

The factor of (d) can be added in the culture medium or on the apical surface.

The factor of (d) can be a mammalian cytokine or a genetically modified mammalian cytokine.

The factor of (d) can be a living organism, a genetically modified organism, a dead organism or part of a dead organism.

Of particular interest is the comparison of the RNA expression level of NF-kB target genes, interferon mediated genes and any pro or anti-inflammatory cytokine. in particular, Example 9 illustrates the effect of recombinant TNFα and IL1 b In promoting the expression of the pro-inflammatory cytokine mRNA expression IL8 in mucosoid culture cultivated stimulated with WNT3A and RSPO1 and unstimulated.

5) Co-Cultivation of Epithelial Cells and other Mucosal Derived Cells in the Mucosoid Culture A further aspect of the presented invention is the possibility to study the interaction between epithelial and non-epithelial compartment of the mucosa by co-cultivation and sub-sequential analysis of the two component of the culture. The epithelium represents only the outer layer of the mucosa that consists also of stromal fibroblast, adipocytes, endothelial cells, muscle cells, but also hematopoietic derived cells (like leucocytes, erythrocytes and platelets) that can infiltrate the mucosa. The maintenance and defense of a functional mucosa depends on the interaction between the different compartments, which can be mediated by direct contact or by secreted factors that are targeting specific cells on the epithelium having the corresponding receptor. The epithelial and non-epithelial compartments can be mutually influenced. With the mucosoid culture, it is possible to study the effect of the interaction of epithelial cells with other cells typically found in the mucosa.

To study the interaction between epithelial cells and the underlying stromal and hematopoietic derived cells of the mucosa the following steps are required:
(a) providing an epithelial cell,
(b) providing a mucosal non-epithelial cell,
(c) contacting the epithelial cell of (a) with a solid semi-permeable surface,
(d) contacting the cell of (b) on a different solid surface,
(e) culturing the cell of (c) under air-liquid interface conditions,
(f) culturing the cell of (b) in liquid conditions,
(g) co-culture the cells coming from step (e) with the cell from step (f), and
(h) harvest and analysis of the mucus, cells and culture medium of (a) and (b) after the co-culture of (g).

The cell of (a) can be from any source of epithelial cells of the mucosoid cultures described herein, in particular in the section "Generation and propagation of columnar epithelial cells into cultivable polarized cell monolayers".

The mucosal non-epithelial cell of (b) is a cell that is resident in the mucosa but is not an epithelial cell. In particular, it can be a stromal fibroblast, adipocyte, endothelial cell, muscle cell.

The mucosal non-epithelial cell of (b) is also a cell that is not resident in the mucosa but migrates in the mucosa e.g. during inflammatory processes. In particular, it can be a leucocyte, an erythrocyte or platelet.

The cell of (b) is a cell from the same or different donor.
The cell of (b) is a cell from the same or different organ.

The cells of (b) can be cultivated in the bottom of the culture vessel which at step (g) is including the carrier of the semi-permeable surface with the cells of (a).

The cell of (b) can be cultivated below the basal side of the epithelium and in this case the cells of (b) are seeded on the semi-permeable surface of the step (c) before the cells of (a). The steps (d) and (f) are in this case not applicable.

The step of (d) can be performed using a cell density of 20,000 to 100,000 cells per $cm^2$, preferably 50,000 cells/$cm^2$.

The co-culture of (g) can be performed for 15 min to >30 days, preferably from 1 to 5 days.

Example 10 shows the co-cultivation of gastric mucosoid culture with stromal cells of the gastric lamina propria isolated from the same patient. In the mucosoid culture of gastric origin stromal cells secrete Wnt inhibitors and drive differentiation of the upper cultivated epithelium towards a foveolar phenotype.

In particular, Example 10, FIG. 17B shows the effect of the co-cultivation and co-cultivation conditioned medium on the expression level of the epithelial LGR5 in the stomach derived mucosoid cultures.

6) Infection of the Mucosoid Culture

The forefront of large part of the gastrointestinal and genital tract mucosa consists mainly of a continuous polarized epithelial monolayer, protected by mucus. This strong defense barrier can be colonized by pathogens that trigger acute and chronic inflammation. Due to the infection, the epithelium may respond by regulating pro-inflammatory signaling pathways. Because of this regulation, the epithelium secretes pro-inflammatory cytokines and especially chemokines for the recruitment of immune cells. In addition, the epithelium might secrete antimicrobial proteins in the mucus. The mucosoid culture of the invention can be a tool to investigate host response to infectious agent. Being the apical compartment easily accessible, the mucosoid culture can be infected with pathogen. The effect on the host can be studied using the mucosoid culture by harvesting the mucus, the cells or the culture medium for subsequent analysis. The mucus produced by the mucosoid culture represents a physical barrier to the infection.

The steps required for the infection of the mucosoid cultures are:
(a) providing an epithelial cell,
(b) contacting the epithelial cell of (a) with a solid semi-permeable surface,
(e) culturing the cell of (c) under air-liquid interface conditions,
(f) providing the pathogenic organism,
(g) co-culture the cells coming from step (e) with the pathogenic organism from (f), and
(h) harvest and analysis of: mucus, culture medium, epithelial cells, pathogen.

The options for the steps (a), (b) and (c) are described herein, in particular in the section "Generation and propagation of columnar epithelial cells into cultivable polarized cell monolayers".

The pathogenic organism of (f) can be a bacterium, a virus or a eukaryotic parasite.

The pathogenic organism of (f) can be isolated from infected individuals, it can be found in the environment or it is a laboratory strain.

The pathogenic organism added to the co-culture of (g) can be genetically modified.

In particular, the pathogen of (f) may be a functional mutant lacking the expression of virulence factors. In particular, the pathogen of (f) may carry genes encoding fluorescent proteins for its detection.

The ratio of pathogenic organisms to epithelial cells (MOI) can be from 0.01 to 1000, preferentially from 10 to 100.

The pathogenic organism can be added dead or alive in the co-culture of (g).

The pathogenic organism can be found dead or alive after the co-culture of (g). The epithelial cells of the mucosoid culture might secrete antimicrobial factor in the mucus after infection that are reducing the viability of bacteria.

The time of co-cultivation of (g) can be extended to >4 weeks.

The pathogenic organism can be added in the co-culture of (g) in liquid medium.

The pathogenic organism can be added in the co-culture of (g) after removing the mucus layer or leaving it.

The pathogenic organism can be added in the co-culture of (g) inside the mucus layer.

The effect of the infection of (g) can be tested after inducing a specific epithelial lineage as indicated herein, in particular in the section "Induction of different epithelial cell lineages inside the mucosoid cultures".

The effect of the infection of (g) can be tested in the co-cultivation conditions indicated herein, in particular in the section "Co-cultivation of epithelial cells and other mucosal derived cells in the mucosoid culture".

In particular, the mucosoid culture of gastric origin can be infected with *Helicobacter pylori* or *Salmonella Paratyphi* A. Examples 11 and 12 are showing the result of the infection with *Helicobacter pylori* and *Salmonella Paratyphi* A of the mucosoid culture of stomach and gallbladder. *Helicobacter pylori* is used at an MOI from 10 to 100. *Salmonella Paratyphi* A is used at an MOI from 10 to 100. *Helicobacter pylori*, after contacting the apical epithelium, is able to inject the virulence factor CagA which is phosphorylated in the host. In particular, infections with *Helicobacter pylori* trigger a high NF-kB related inflammatory response only if the mucosoid culture is cultivated under the condition in which the WNT pathway is activated (Example 11). In particular, *Salmonella Paratyphi* A is able to colonize the epithelium of the culture and internalize inside the epithelial cells. Infection with *Helicobacter pylori* and *Salmonella Paratyphi* can be extended to 4 weeks. Example 6 shows that the mucus produced by infected epithelial monolayers display a bactericidal activity.

Utility of the Invention

The established mucosoids serve for a variety of purposes, including (1) the long-term maintenance or amplification of epithelial cells used in this invention, (2) the exploration of the behavior of the cells in response to extrinsic stimuli, (3) the transport of substances or factors from apical to basolateral directions, or vice versa, or the translation of biological chemical and physical signals arriving from either direction, (4) their usage as a production tools for biological factors useful for technical and medical purposes, (5) their usage as an apical platform to facilitate and reproduce various extracorporeal biological processes, (6) their usage in more complex biological settings with additional cell populations beyond the semi-permeable filter to reproduce various intracorporeal processes, and (7) human diagnostic or therapeutic applications.

1) Amplification of cells: Larger amounts of epithelial cells are often required to allow for biological, pharmaceutical and medical purposes. Examples include the use of cells derived from mucosoids as high-throughput screening tools, as source for the generation of biological products, and for medical diagnostic or therapeutic purposes. An advantage of the current invention is the relatively inexpensive production of such amounts of cells, specified in this invention.

2) Cellular processes: There is great need to screen or otherwise assess the features of synthetic or natural molecules with regard to their activity on epithelial cells, such as outlined in this invention. The mucosoids resemble ideal systems to assess the biological effects of any kind of extrinsically exerted stimulus in either isolated assays or high-throughput formats. Such exerted stimuli could, for example, be physical pressure or electrical signals, pharmacologically active substances, and biological factors such as infectious agents, hormones and cytokines, all of which could be provided from either one or both the apical and basolateral sides of the mucosoids. Accordingly, mucosoids may be used as assay systems to assess the biological features of small molecule compounds as well as to elucidate the molecular mechanisms by which epithelial cells respond to exerted stimuli.

3) Transport and signal transduction: The polarized epithelial cells of living organisms as they are represented in mucosoids exert numerous molecular transport functions and are exquisitely equipped to transmit signals from either apical to basolateral or vice versa. Such transfer of signals might involve binding of a molecule to a cellular surface receptor which, after intracellular processing of the signal, might lead to the exposition or the release of a cellular molecule at the opposite pole of the mucosoid cells. Alternatively, a signaling molecule could bind to the surface of a mucosoid cell and become transported itself to the opposite pole of that cell. Finally, signals may be transferred laterally from cell to cell within the mucosoid monolayer. The trigger of the signaling processes in the mucosoids and the subjects of transport through and in between cells of the mucosoids might be singular molecules, molecular assemblies of multiple molecules (such as vesicles), or even larger particles such as infectious agents (such as viruses, microbes). Thus, any kind of extrinsic trigger, including infectious agents, vesicles etc., could be applied onto the apical surface of the mucosoids or applied to the semi-permeable filter surface to target the basolateral surfaces of the mucosoid cells. The resulting responses can then be measured under (a) live conditions of the mucosoids by analyzing secreted or transported material or by means of physical measurements, including microscopy and (b) by harvesting the mucosoid cells and analyzing their content.

4) Production tools: The mucosoids are found to exhibit unique epithelial properties, which do not effectively proceed in epithelial cells when cultured other than as mucosoids. One example is the production and apical secretion of mucous. Mucous is a valuable component of mucosal surfaces and associated with additional factors besides the core protein component, the mucins. The capacity of mucosoids to produce large amounts of mucins can be extrapolated to other cellular products, particularly also recombinant products. Moreover, since mucosoids are very active in selectively transporting molecular cargo in either direction of the two poles they can be employed for such processes. Examples include the selective transport of bile acids and of antibody from the basolateral to the apical pole of the cells. A further example is the transport apical transport of protons mediated by the H+/K+ ATPase pump of the stomach derived mucosoids. Importantly, very often, such as in the case of transporting dimeric IgA antibody, the molecular cargo will be specifically modified during the passage through the mucosoid cells. The mucosoids, therefore constitute valuable tools for the production and refinement of medically or biologically valuable substances. Intermediate stages or final products of this refinement process can be harvested from the extracellular compartments of the mucosoids.

5) Representation of the extracorporeal environment: Numerous biological processes take place on the apical surfaces of the mucosa which can be reproduced by the use of mucosoids. One prominent example includes the process of fertilization, where the oocyte is in close contact to the epithelial surface of the Fallopian tubes of the female reproductive tract. In vitro fertilization of oocytes both of animal or human origin in currently insufficient and involves the risk of genetic damage. The invention of mucosoids will therefore be useful to facility the process of in vitro fertilization and, by providing an authentic environment, decrease the risk of genetic damage. Another example refers to the microbiome, which is known to have multiple effects on physiological processes and human health. Using the mucosoids, the biological processes involving the microbiome can now be investigated under authentic conditions. This is because the microbiome undertakes constant molecular communication with the apical surface of the mucosa, which is now presented as a mucosoids. Furthermore, the microbiome in influenced by the surrounding atmosphere, including oxygen concentrations and pH. Notably, the mucosoids are suited to adjust differential conditions of media and atmospheric properties on either side of the monolayer. Therefore, by performing cultivation of any microbiome on suitable apical mucosoid surfaces can lead to the identification of critical factors involved the cross-talk between microbiome components, including pathogenic agents, as well as signaling molecules acting between the microbiome and the mucosal surfaces.

6) Representation of the intracorporeal environment: Numerous biological processes also take place at or beyond the basolateral pole of the cells contained in the mucosoids including the compartment beyond the semi-permeable filter, used as a base of the mucosoid. In the natural mucosa, this intracorporeal compartment includes a variety of cells of different lineages, such as mesenchymal cells, fibroblasts, hematopoietic cells, and endothelial cells. By the use of mucosoids these cells can be brought into a condition of cross-talk via the diffusion of biologically active molecules from either cell type. Moreover, depending on the pore size of the filters used, protrusions of the intracorporeal cells can additionally obtain direct contact to the basolateral poles of the mucosoids. This way, the mucosoids serve to dissect the complex cross-talk and signaling factors involved within the intracorporeal host cell networks. The identification of such signaling factors will not only promote basic understanding of fundamental physiological processes but inevitably lead to the identification and production of technically and medically important compounds.

7) Direct medical use: The epithelial cells contained in the mucosoids constitute themselves a valuable product for medical use. Wherever there is replacement or substitution of polarized epithelial surface needed such cells can be derived from mucosoid cultures. One of the exquisite advantages of the mucosoids is that they can be obtained under controlled GMP conditions with components needed for their propagation, which suffice the high standards required for medical use. For example, the propagation of mucosoids does not depend on the presence of relatively undefined matrix materials, such as Matrigel.

EXAMPLES

Example 1

Generation of Gastric Derived Mucosoid Cultures

The gastric tissue is resected from obese patients undergoing sleeve gastrectomy. A 2×2 cm from the resection is preferentially use as a starting material for the isolation. The gastric tissue is washed PBS/supplemented with 50 µg/ml gentamicin, 100 U/m1 penicillin and 100 µg/ml streptomycin) to remove the blood (or chill protect buffer BIOCHROME for longer times). The tissue is cleaned from muscle, adipose tissue, blood vessels and if possible from lamina propria under the dissecting scope. The tissue is washed in PBS. The tissue is chopped into small pieces (1 mm) and washed in 25 ml of sterile PBS solution by vortexing. Fat tissue is slowly precipitating compared with the epithelium. After vortexing, wait for the epithelium to precipitate and remove the supernatant with the fat tissue. Repeat until the SPNT is clear (usually 5-8 times with 25 ml of PBS each time). Discard SPNT and incubate with 45 ml chelating solution (distilled water with 5.6 mM $Na_2HPO_4$, 8.0 mM $KH_2PO_4$, 96.2 mM NaCl, 1.6 mM KCl, 43.4 mM sucrose, 54.9 mM D-sorbitol, 0.5 mM DL-dithiothreitol, 2 mM EDTA) for 20/30 min at 37°, (or 3-4 hours at 4° rocking). SPNT is discarded and pieces are put into a sterile petri dish. The pieces are pressed with a sterile microscope glass slide with a pressure that allows extraction of the gland without damaging the cells. Pieces are recovered with 3 ml of media with FCS (to inactivate the chelating solution). The pieces are washed from the glass with 3 ml of the same media and from the petri dish. Put the total 6 ml in a 15m1 falcon tube and pipette 3-4 times up and down. Transfer the supernatant in a new falcon and repeat the procedure until all the big pieces are gone. Transfer 10 ul in a plate and count the gland fragments under the microscope. Make the calculation for three different gland dilution (ex 400 200 100 or 500 250 50). Dissolve in DMEM F12 (w/o FCS) Centrifuge the glands (1200 rpm 5 min 4°) and dry the pellet. Dissolve the equivalent of 200,000 to 250,000 and seed in 200 µl culture medium into collagen-coated (Gibco A10644-01, 15 µg/cm2) transwell inserts (Millipore PIHP01250) placed in a 24-well plate at 37° C., 5% $CO_2$ in a humidified incubator. A "transwell insert" supplied by Millipore, is a polycarbonate cell culture insert with pore size of 0.4 µm used in a 24-well plate for cell attachment, cell culture, cell differentiation, drug transport & permeability. The space between filter and well was filled with 400 µl culture medium (Table 1). On day three, the medium overlying the cells was removed from the well insert to start the ALI culture. The 500 µl medium below the filter was replaced twice a week.

TABLE 1

| Medium composition | | | |
|---|---|---|---|
| Component | Concentration | Manufacturer | Cat. No. |
| ADF | 18.45% V/V | Thermo Fischer | 12634 |
| conditioned Wnt3A-medium (as described in Willert et al), | 50% V/V | | |
| 25% conditioned R-spondin1 medium | 25% V/V | | |
| 4-(2-hydroxyethyl)-1-piperazine-ethane-sulfonic acid, | 10 mM | Thermo Fischer | 15630-056 |

TABLE 1-continued

Medium composition

| Component | Concentration | Manufacturer | Cat. No. |
|---|---|---|---|
| Glutamax | 1% V/V | Thermo Fischer | 35050-087 |
| B27 | 2% V/V | Thermo Fischer | 17504044 |
| N2 | 1% V/V | Thermo Fischer | 17502048 |
| human epidermal growth factor (EGF) | 20 ng/ml | Thermo Fischer | PHG0311 |
| human noggin (Peprotech) | 150 ng/ml | Peprotech | 120-10C-1000 |
| human fibroblast growth factor (FGF)-10 | 150 ng/ml | Peprotech | 100-26-1000 |
| nicotinamide | 10 mM | Sigma | N0636 |
| human gastrin | 10 nM | Sigma | G9145 |
| A83-01 | 1 µM | Calbiochem | 616454 |
| Y-27632* | 7.5 µM | Sigma | Y0503 |

*after the 3rd day the concentration was reduced to 1.5 µM

We used qRT-PCR to monitor the long-term stability of cultures that were passaged once a month. Expression of the gastric epithelial markers KRT8, 18 and 19, EPCAM and CHD1 remained constant for up to seven months (FIG. 8). Expression of the gastric stem cell marker LGR5[11] also remained constant after the first passage, as did β-catenin and CD44, a marker of proliferating and stem cells in the stomach [7] (FIG. 8). At the same time, markers of differentiated gland phenotypes were also expressed at constant levels, including PGC for chief cells, MUC6 for cells at the gland base, MUC5AC for foveolar, CHGA for enteroendocrine and ATP4B for parietal cells (FIG. 8) indicating that the phenotypic composition remains unchanged over time.

Figure 9:
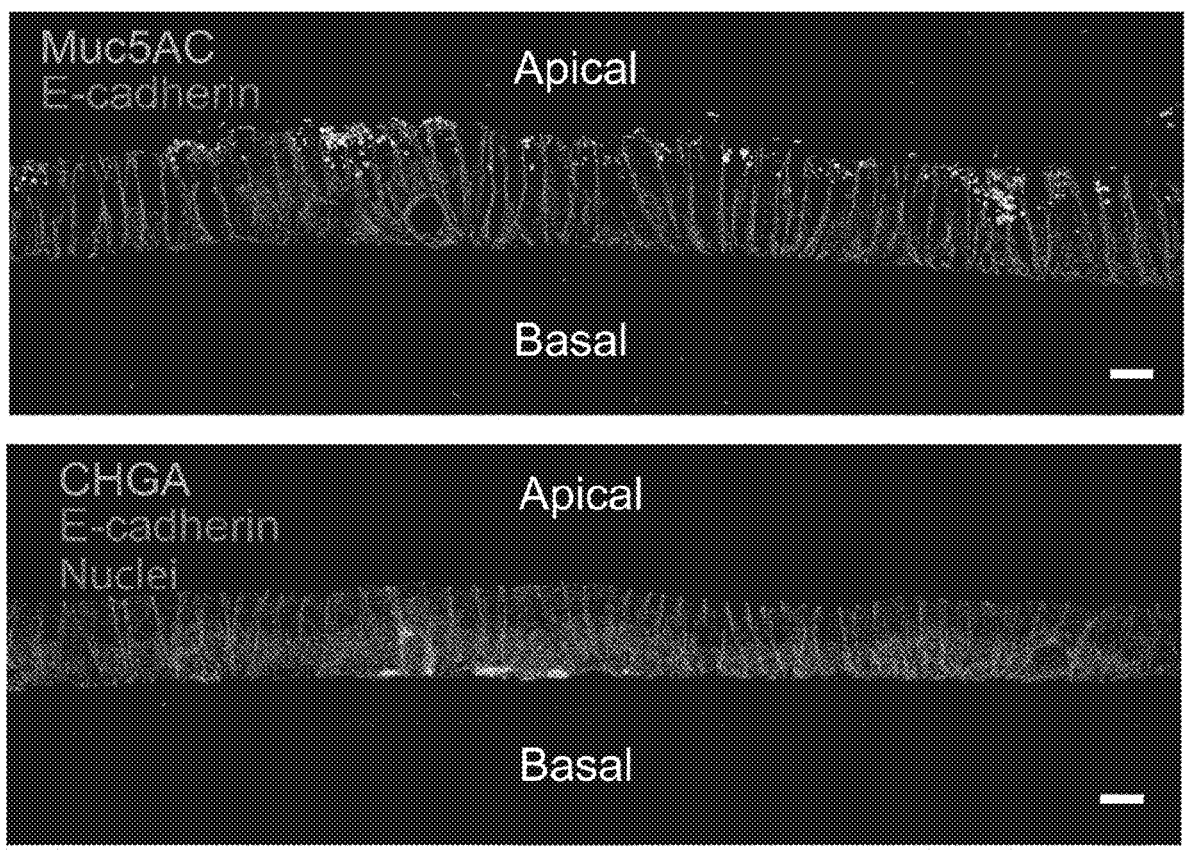

The polarization of mucosoid cultures reflects that observed in the stomach with the apical side facing up where mucus is accumulating and the basal side facing the filter where nutrients and growth factors are taken up. Nuclei were localized on the basal side (FIG. 4), while E-Cadherin was expressed only basolaterally and never apically (FIG. 4) and that expression of the tight junction marker occludin is restricted to the apical side (FIG. 2B). Trans-epithelial electrical resistance (TEER) to ion migration ranged from 370 to 470 Ω*cm$^2$, depending on cell density, which is higher than colon but lower than lung epithelium. [12] A top view shows that tight junctions (green) appear as characteristic dots connecting apically contiguous cells forming a continuous barrier (FIG. 2). Since epithelial barriers have a high turnover, proliferation as well as cell extrusion are equally important to preserve constant cell number. Interestingly, when we imaged lower stacks, we found invaginations of tight junctions that formed rosette-like structures with the surrounding cells (FIG. 2). A similar phenomenon was described as a process of cell extrusion which trigger basal physiological rearrangement of tight junctions [9, 10] to maintain the epithelial barrier integrity. To further stress the high polarization degree of the mucosoid cultures we analyzed gastric epithelial secreted proteins in the apical or in the basal compartment. The glands are populated by many cells producing mucus and in particular the mucin MUC5AC. Analysis of undifferentiated mucosoid culture also revealed intracellular MUC5AC granules that accumulate apically for secretion (FIG. 9) and which contribute to the formation of an apical mucus layer. On the contrary, we observed basal accumulation of chromogranin A granules typical for enteroendocrine cells (FIG. 9).

Example 2

Generation of Colon Derived Mucosoid Cultures

Tissue samples are collected in Chillprotec buffer (Biochrom F2283) supplemented with 50 µg/ml gentamicin, 100 U/ml penicillin and 100 µg/ml streptomycin, then washed in DPBS and cut into <0.5 mm pieces. The tissue fragments were incubated in chelating solution (distilled water with 5.6 mM Na$_2$HPO$_4$, 8.0 mM KH$_2$PO$_4$, 96.2 mM NaCl, 1.6 mM KCl, 43.4 mM sucrose, 54.9 mM D-sorbitol, 0.5 mM DL-dithiothreitol, 2 mM EDTA) for 30min at 4° on a rolling platform. The tube containing the tissue pieces is vigorously shaken to extract the colon crypts subsequently the bigger tissue fragments are settled down by gravity. The supernatant is centrifuged at 100 g for min, pellet resuspendend in medium containing 10% heat-inactivated fetal calf serum (FCS; Biochrom), and the last washing step repeated once more. 25000 cells are seeded in a 50 µl drop of Matrigel (Corning) supplemented with medium. After 10-14 days of culture the organoids are dissociated in 0.05% trypsin/EDTA using a narrowed Pasteur pipette. Dissociated cells are washed once by centrifugation and resuspension in ADF medium containing 5%FCS. 300.000 cells are seeded in 200 µl culture medium into Matrigel-coated (20% in DMEM) transwell inserts (Millipore PIHP01250) placed in a 24-well plate. The space between filter and well was filled with 400 µl culture medium. On day three, the medium overlying the cells was removed from the well to start the ALI culture, the 400 µl of medium below and around the insert is replaced with 500 µl of new medium refreshed every 3-4 days. The medium used is identical to the used to grow organoids.

Composition of the Media

Advanced DMEM/F12 (ADF, GIBCO), 50% (4× concentrated) conditioned WNT3A-medium and 25% conditioned R-spondin1 medium 24 supplemented with 10 mM 4-(2-hydroxyethyl)-1-piperazineethanesulfonic acid, 1% Glutamax, 2% B27, 1% N2, 20 ng/ml human epidermal growth factor (EGF) (all Invitrogen), 150 ng/ml human noggin, 150 ng/ml human fibroblast growth factor (FGF)-10 (both Peprotech), 10 mM nicotinamide, 10 nM human gastrin, 2 µM SB202190, 9 µM Y-27632, 1 nM CHIR99021 and 1 µM PGE2 (all Sigma) 1 µM A83-01 (Calbiochem). Murin epithelial cells were cultivated using the same medium but with murin derived EGF and noggin.

Example 3

Generation of Gallbladder Derived Mucosoid Cultures

Tissue samples are collected in Chillprotec buffer (Biochrom F2283) supplemented with 50 µg/ml gentamicin, 100 U/ml penicillin and 100 µg/ml streptomycin. Bile acids and mucus are removed by washing with PBS and by gently scraping the mucosa. The sample is transferred into a 50 ml tube containing 25 ml PBS shaken and supernatant discarded. This operation is repeated till the supernatant is not yellow anymore, indicating the complete removal of bile acids. The mucosa of the gallbladder is then immersed with the apical side facing a 10 cm Petri dish filled with 15 ml of 0.2% type IV collagenase in PBS for 5 min at 37° C. The mucosa is abraded thoroughly with the edge of glass coverslip held with an angle of 45°. The resulted cells are collected by flushing with DMEM. The operation in repeated 3 times and the supernatant containing cells is strained thorough a 70 µm filter. The filtrated liquid is centrifuged to remove excess of SPNT. 25,000 cells are seeded in a 50 µl drop of Matrigel (Corning) supplemented with medium and after 14 days of culture the organoids are dissociated in 0.05% trypsin/EDTA using a narrowed Pasteur pipette. Dissociated cells are washed once by centrifugation and resuspension in ADF medium containing 5% FCS. 300,000 cells are seeded in 200 µl culture medium into Collagen-coated (Gibco A10644-01 1.5 µg/cm2) transwell inserts (Millipore PIHP01250) placed in a 24-well plate. The space between filter and well was filled with 400 µl culture medium. On day three, the medium overlying the cells was removed from the well to start the ALI culture. The 400 µl of medium below and around the insert is replaced with 500 µl of new medium refreshed every 3-4 days. The medium used is identical to the used to grow organoids.

Composition of the Medium

25% R-spondin conditioned medium, noggin 150 ng/ml, hEGF20 ngµl, HGF 25 ng/ml, FKS 10 µM, B27 2%, N2 1%, Nicotinamide 10 µM, 7.5 µM Y-27632, 0.5 µM TGF-β R Kinase Inhibitor IV. Murin epithelial cells were cultivated using the same medium but with murin derived EGF and noggin.

Example 4

Generation of Fallopian Tube Derived Mucosoid Cultures

Tissue samples are collected in Chillprotec buffer (Biochrom F2283) supplemented with 50 µg/ml gentamicin, 100 U/ml penicillin and 100 µg/ml streptomycin, then washed in DPBS and cut into <0.5 mm pieces. The tissue fragments were incubated in chelating solution (distilled water with 5.6 mM Na2HPO4, 8.0 mM KH2PO4, 96.2 mM NaCl, 1.6 mM KCl, 43.4 mM sucrose, 54.9 mM D-sorbitol, 0.5 mM DL-dithiothreitol, 2 mM EDTA) for 30 min at 4° C. on a rolling platform. The tube containing the tissue pieces is vigorously shaken to extract the colon crypts subsequently the bigger tissue fragments are settled down by gravity. The supernatant is centrifuged at 100 g for min, pellet resuspendend in medium containing 10% heat-inactivated fetal calf serum (FCS; Biochrom), and the last washing step repeated once more. 25,000 cells are seeded in a 50 µl drop of Matrigel (Corning) supplemented with medium. After 10-14 days of culture the organoids are dissociated in 0.05% trypsin/EDTA using a narrowed Pasteur pipette. Dissociated cells are washed once by centrifugation and resuspension in ADF medium containing 5% FCS. 300,000 cells are seeded in 200 µl culture medium into Matrigel-coated (20% in DMEM) transwell inserts (Millipore PIHP01250) placed in a 24-well plate. The space between filter and well was filled with 400 µl culture medium. On day three, the medium overlying the cells was removed from the well to start the ALI culture, the 400 µl of medium below and around the insert is replaced with 500 µl of new medium refreshed every 3-4 days. The medium used is identical to the used to grow organoids.

Composition of the Media

Advanced DMEM/F12 (ADF, GIBCO), 50% conditioned WNT3A-medium and 25% conditioned R-spondinl medium 24 supplemented with 10 mM 4-(2-hydroxyethyl)-1-piperazineethanesulfonic acid, 1% Glutamax, 2% B27, 20 ng/ml human epidermal growth factor (EGF) (all Invitrogen), 150 ng/ml human noggin, 150 ng/ml human fibroblast growth factor (FGF)-10 (both Peprotech), 10 mM nicotinamide, 10 nM human gastrin, 2 µM SB202190, 9 µM Y-27632, 1 nM CHIR99021 and 1 µM PGE2 (all Sigma) 1 µM A83-01 (Calbiochem).

Example 5

High-Throughput Analysis of the Mucus Secreted by the Mucosoid Cultures 10 days after starting ALI culture the mucus is removed and new accumulation of it started for 5 days. The analysis shows the differential composition of the mucus when the WNT pathway is activated by exogenous WNT3A and RSPO-1 administration and without. FIG. 10A shows the analysis of the differential composition of the mucus when the WNT pathway is activated by exogenous WNT3A and RSPO-1 administration and without. Other proteins like the antimicrobial muramidase Lysozyme, trefoil factors, and hormone like gastrokine are also found expressed in the mucus of the mucosoid cultures. The relative amount of the different protein found in the mucus might change upon differential stimulation of the mucosoid culture. In this specific example the effect of WNT3A and RSPO1 is shown.

Example 6

Analysis of the Bactericidal Activity of the Mucus

FIG. 10B shows that the mucus constitutes a physical barrier against infectious agents like *Helicobacter pylori*. Paraffin section of a mucosoid culture infected with *Helicobacter pylori* at MOI 50 for 72 h. The bright layer indicates the cell layer. The bacteria are mostly bound to a continuous mucus layer that only a few have managed to infiltrate (arrowheads). FIG. 10C shows that the mucus produced after infection has bactericidal activity. Epithelial cells from healthy human stomach were grown as mucosoid culture for 10 days and were either mock infected or infected at MOI-100 with *H. pylori* P12. After 3 days, mucus layer was collected in microcentrifuge tubes. In parallel, *H. pylori* P12-GFP (kanR) were grown on GC agar plates with vancomycin and kanamycin. Bacteria were collected and washed once with PBS, and a suspension containing ~2×10$^7$ CFU/ml was prepared in PBS. Aliquots of 5 µl (~10$^5$ CFU) were mixed with 20 µl of fresh mucus collected from ALI cultures. After incubation at 37° C., surviving bacteria were enumerated following culture on GC agar plates with vancomycin. To kill wild type bacteria used for cell infection, GC plates also contained kanamycin. Results are expressed as the percentage of bacteria surviving from the initial input.

Example 7

Figure 12:
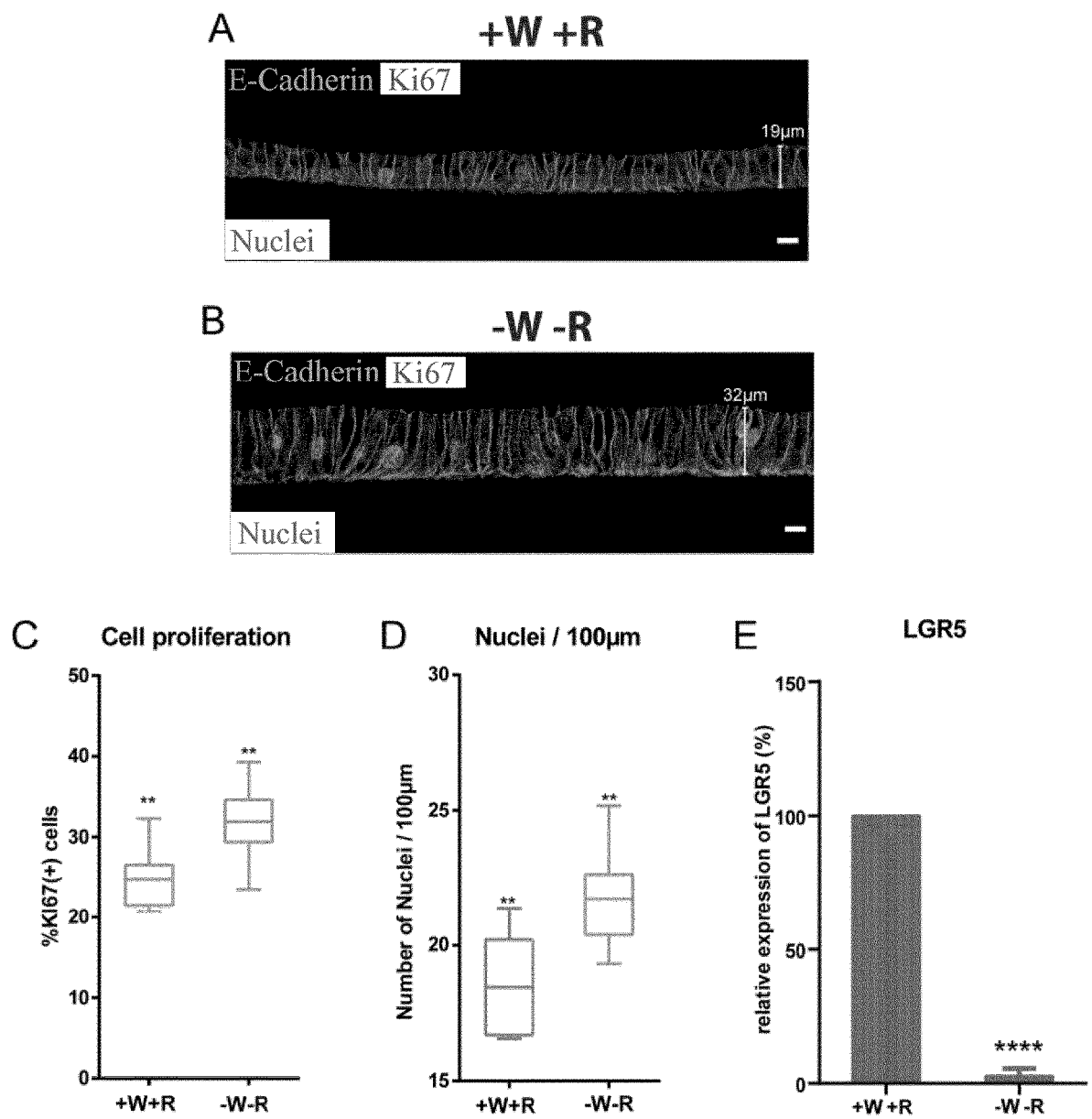
Figure 13:
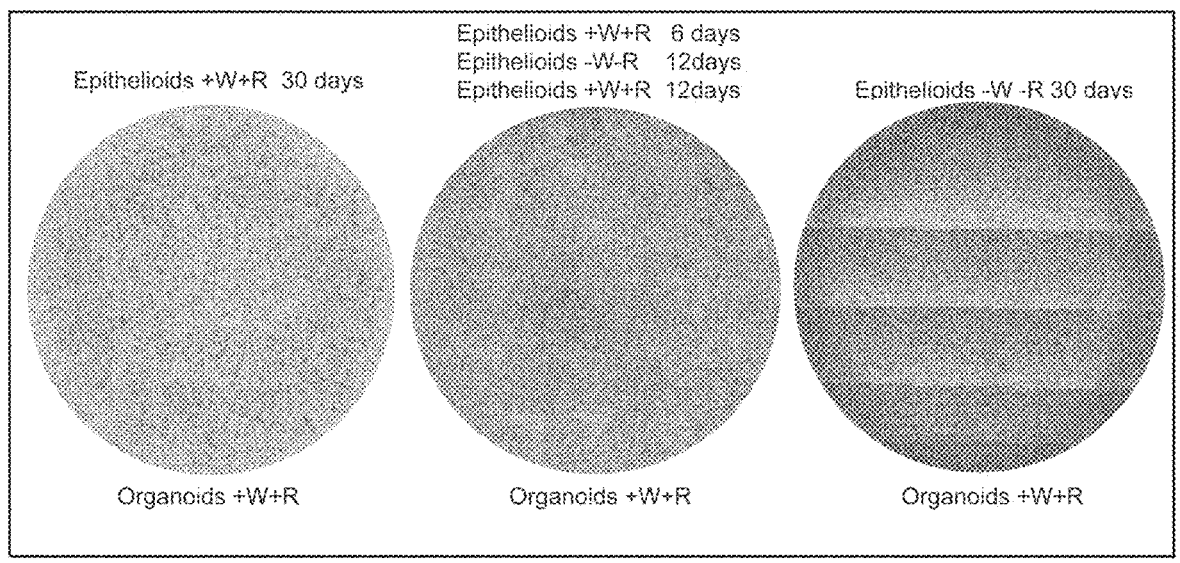
Figure 14:
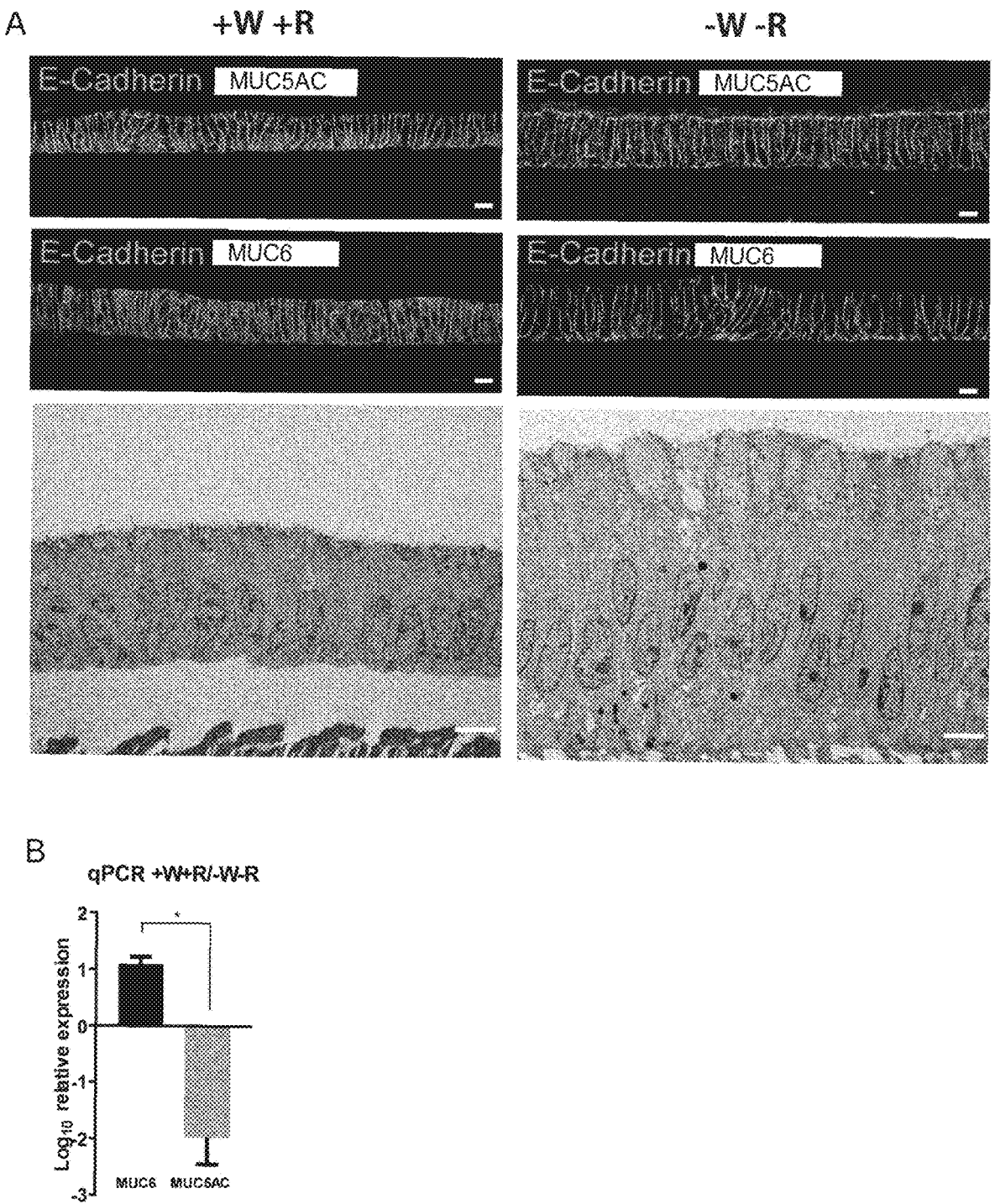

Activation of the WNT Pathway Promotes the Expansion of Cells Belonging to the Base of the Gastric Antral Gland in the Mucosoid Cultures The WNT pathway is driving the expression of the base of the gland cells of the antral part of the stomach. Lineage tracing experiments in mice have demonstrated that the base of the gland in the Antrum is populated by Lgr5-expressing stem cells that are able to re-populate the whole gland. These cells proliferate and migrate up to the pit of the gland, forming the foveolar lineage [11]. The stem cell niche in vivo largely depends on activation of the WNT pathway, which is mimicked by supplementing the culture medium with recombinant WNT3A (+W) and RSPO1 (+R) [13]

leading to the release of β-catenin in the cytoplasm and translocation into the nucleus (FIG. 11), where it acts as a transcriptional coactivator of transcription factors. Depriving cultures of WNT3A/RSPO1 (−W−R) for 6 days removes β-catenin from the nucleus (FIG. 11) and mimics the process of differentiation into the foveolar phenotype. A continuous proliferative zone in the stomach is found in the glands parallel to gastric mucosa. In the antrum, which is characterized by a longer foveolar compartment, this zone is located deep in the pits [14]. By depriving WNT3A and RSPO1 we noticed an increase number of KI67+ proliferative cells (from 25% to 32% of total cells) that increases the height (from 19 μm to 32 μm) and the of density cells (from 17 nuclei to 22 nuclei each linear 100 μm) which is typical for the pits (FIG. 12 A, B, C, D). Deprivation of WNT3A and RSPO1 further induced as expected a drastic reduction in the expression of the stem cell marker LGR5 (2% of the initial expression) FIG. 12 E). To test whether this differentiation is reversible, we seeded primary cells on filters to establish a mucosoid culture and then withdrew WNT3A and RSPO1 for 12 or 30 days. Single cells were transferred to organoid culture conditions, restoring the supply of WNT3A and RSPO1. The ability to form organoids was greatly and permanently reduced (<1%) compared to controls even when WNT and RSPO were only withdrawn for 12 days (FIG. 13). The glands of the gastric mucosa are protected against acid and digestive enzymes by a mucus gel that polymerizes at different densities. In the normal gastric mucosa MUC5AC is produced on the surface, while MUC6 is expressed deeper in the gland [15, 16]. Similarly, low levels of MUC5AC (red) are detectable if mucosoid cultures are kept in +W+R medium (FIG. 14A), while −W−R medium induces extensive production of this mucin (FIG. 14A). The opposite is observed for MUC6, which is produced at high levels in +W+R medium (FIG. 14A) and drastically diminished after 6 days in −W−R medium (FIG. 14A). The mRNA expression levels of MUC6 and MUC5AC are respectively 10 times higher and 100 times lower when the mucosoid cultures cultivated with WNT and RSPO are compared to the counterpart cultivated without.

Example 8

Figure 15:
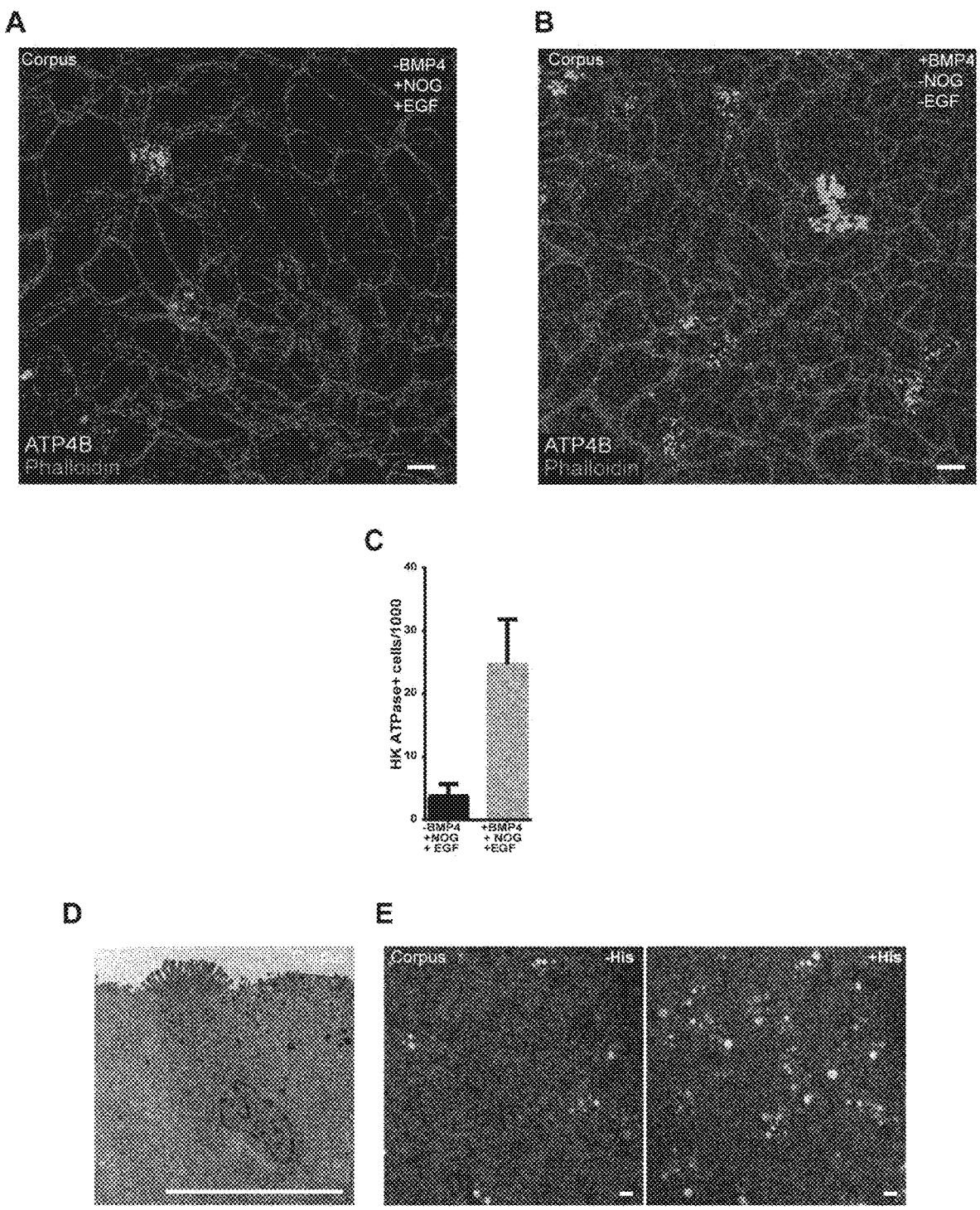

The BMP Pathway Promotes Gastric Parietal Cell Differentiation and Histamine Induces Acid Production FIG. 15 shows the effect of the activation of the BMP pathway and histamine in the activation of functional acid producing parietal cells. We found for example that ATP4B+ parietal cells are present but particularly rare in the gastric-corpus derived mucosoid cultures. Specific signals are needed to drive the parietal cell lineages and in particular the activation of BMP4 and the suppression MEK/MAPK pathway [17]. When we provided BMP4 in the absence of Noggin (an inhibitor of BMPs) and EGF (an activator of MEK/MAPK) for two weeks we noticed an augment from 0,4% to 2,4% of ATP4B$^+$ parietal cells (FIG. 15 A,B,C). The parietal cells show an intense concentration of mitochondria next to numerous tubolovesicles on the apical side which is a reminiscence of their typical ultrastructure (FIG. 15D). Furthermore these cells are able to produce acid after stimulation with histamine as detectable using the dye acridine orange, which changes to an orange color in acidic micro-environment (FIG. 15E).

Example 9

Figure 16:
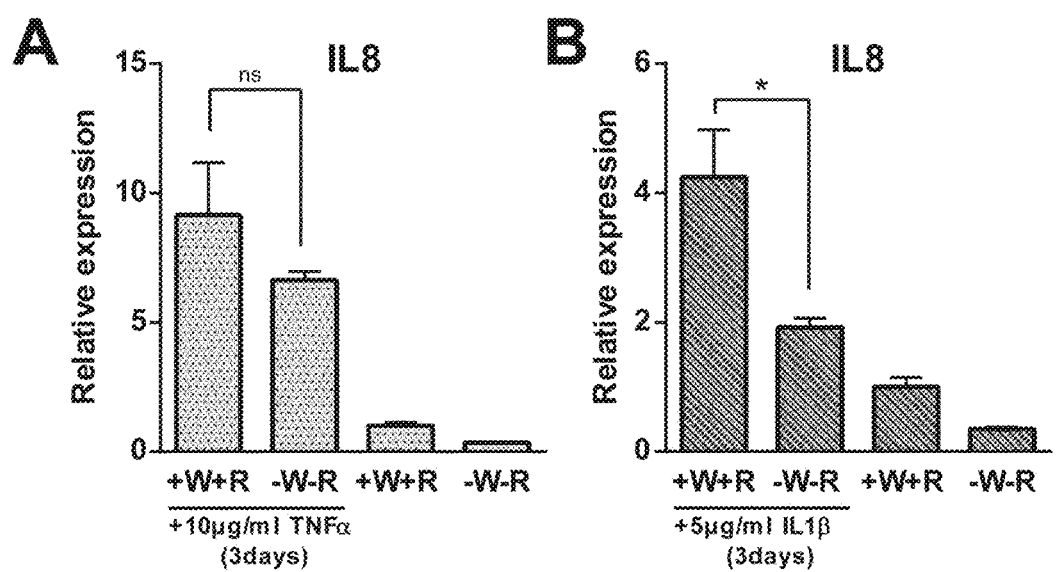

Analysis of the Pro-Inflammatory Effect of TNFα and IL1b in Mucosoid Culture where the WNT Pathway is Activated or Not FIG. 16 shows the effect of the proinflammatory stimuli mediated by TNFα and IL1b to cells derived from mucosoid culture of the foveolar type (−WNT−RSPO) or of the basal type (+WNT+RSPO) To this end +W+R and −W−R gastric-antrum mucosoid cultures were treated with either TNF-α or IL1-β for 3 days, followed by qPCR. TNF-α induced IL-8 expression regardless of W/R, (FIG. 16A, while IL1-β induced IL-8 preferentially in +W+R cultures (FIG. 16B). This result shows that the base of the gland are more responsive to inflammatory stimulus compared to the foveolae.

Example 10

Figure 17:
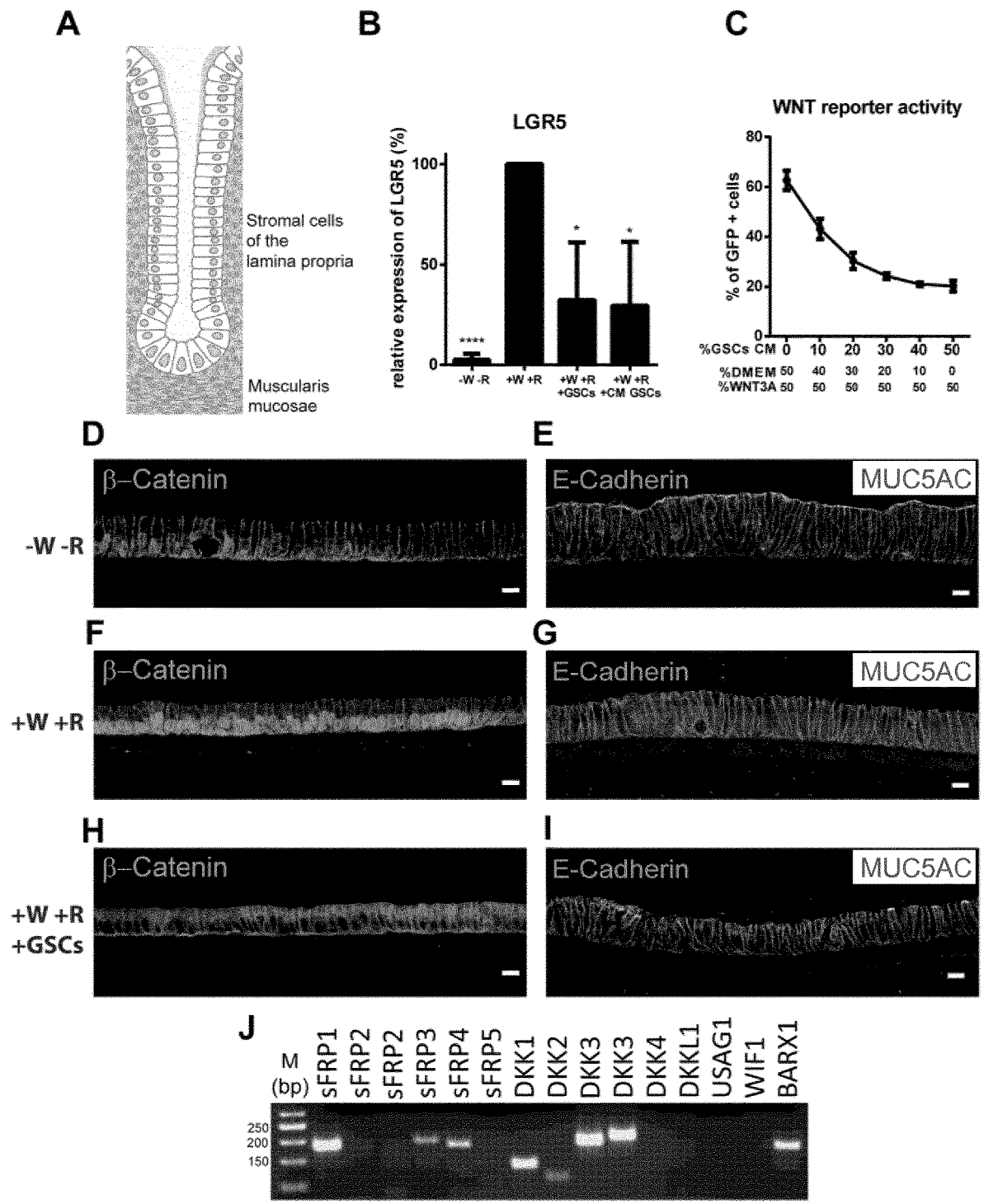

Co-Cultivation of Gastric Mucosoid with Stromal Cells from the Gastric Lamina Propria Isolated from the Same Patient FIG. 17 shows the effect of the co-cultivation of stromal cells of the lamina propria of the stomach mucosa with the respective epithelium in a mucosoid culture. The gastric mucosa is organized into glands intercalated by the *lamina propria*, which consists of stromal fibroblasts. These stromal cells differ from the myofibroblast of the *lamina muscularis mucosae* directly beneath the glands (FIG. 17A). We isolated and expanded gastric stromal cells (GSCs) of the *lamina propria* and added them to the basal compartment of the mucosoid culture. After six days, the level of epithelial LGR5 mRNA was reduced, as determined by q-PCR. This effect was reproduced by exposing the cultures to GSC-conditioned medium (FIG. 17B), suggesting that it is due to a secreted factor. To test if the reduction in LGR5 expression was due to alterations of the WNT signaling pathway, we titrated the GSC-conditioned medium on a WNT reporter cell line activated with 50% of LWNT3A supernatant (a cell line producing abundant WNT3A) (FIG. 17C). While 50% LWNT3A supernatant generated a strong reporter signal, combination with GSC-conditioned medium reduced the signal (FIG. 16C). Distribution of β-catenin also showed nuclear location only when the WNT pathway is activated by WNT3A and RSPO1 (FIG. 17D, F) but not when cells are co-cultured with GSCs (FIG. 16H) and undergo partial differentiation into foveolar phenotype as shown by an increase in MUC5AC producing cells (FIG. 17I compared to 17G). The stroma of the *lamina propria* thus reduces the sternness capacity of the epithelium and induces partial differentiation via secreted factors that inhibit the WNT pathway in a β-catenin-dependent fashion. To further analyze which factors are responsible for the reduction in LGR5 expression, we tested mRNA expression of all the soluble WNT inhibitors. We observed strong expression of sFRP1, DKK1 and DKK3, as well as BARX1, a transcription factor regulating sFRPs (FIG. 17J). As epithelial homeostasis is tightly controlled, signals coming from other cells might perturb this equilibrium. This indicate that with the mucosoid culture co-cultivation it is possible to model epithelium-stroma communication and that it is a sensitive system to analyze sternness and epithelial homeostasis.

Example 11

Infection of Gastric Mucosoid Culture with *Helicobacter Pylori*

Figure 18:
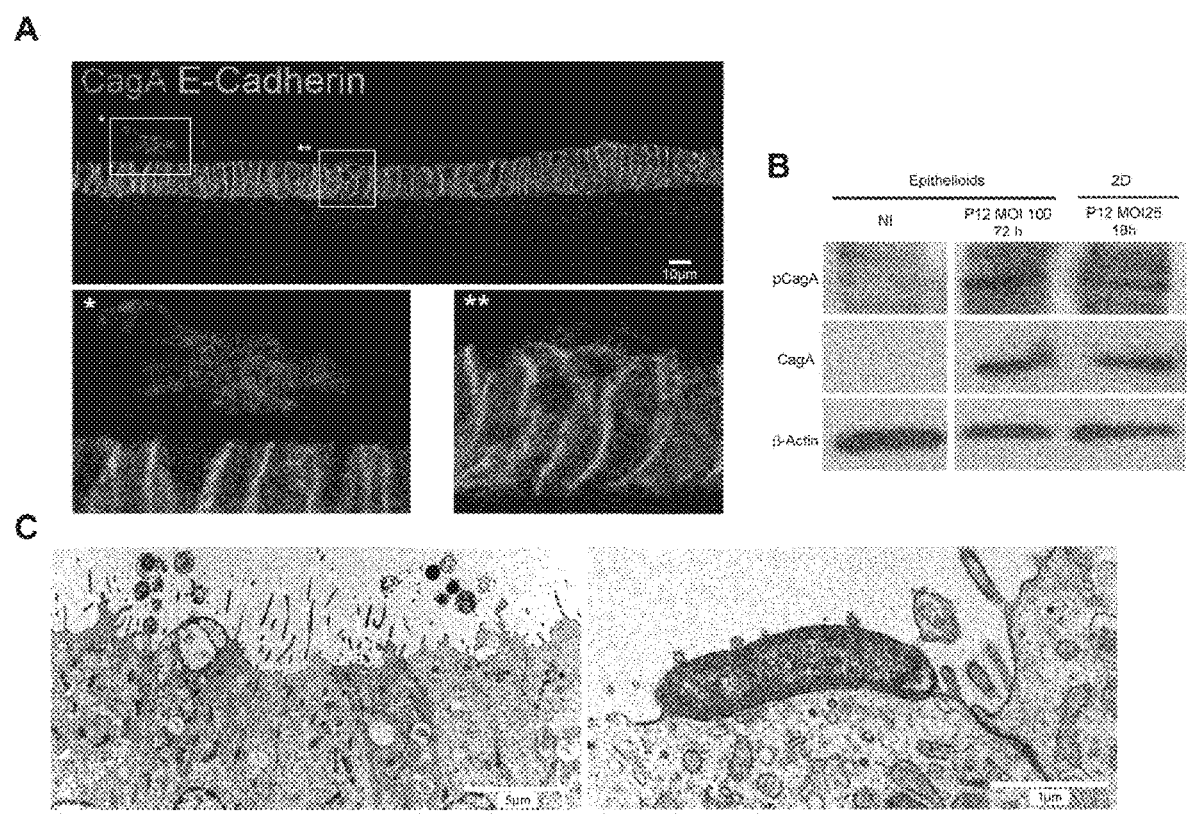

FIG. 18 shows that mucosoid culture derived from healthy human gastric samples can be infected with *Helicobacter pylori* and that the host cells show a response against infection. During the infection the bacteria are always organized in foci and do not disrupt the monolayer as in conventional 2D culture. We therefore investigated adhesion dynamics and the role of the mucus in controlling the infection. Confocal images of the infected gastric-antrum mucosoid cultures (+W+R) at 72 h show some of these colonies still trapped in the mucus (FIG. 18A left enlargement) or adhering to the surface of the epithelium (FIG. 18A right enlargement). Translocation of the bacterial CagA protein was confirmed by the presence of phosphorylated protein detected by western blotting (FIG. 1B). To improve the resolution we have used a GFP expressing isogenic strain and trimmed the filter containing the infected mucosoid culture in the area containing green fluorescence. These little squares enriched in infected cells where sectioned and processed for electron microscopy. Interestingly, we found that most of the bacteria are coccoid after 12-24 h, that they produce a large number of vesicles and that the majority of the bacteria do not contact the epithelium on the apical surface but rather through the microvilli (FIG. 18C left panel). However also helical shaped bacteria can be found adhering to the surface 6 h after infection started (FIG. 18C right panel).

We next tried to model long-term infection with *H. pylori*. We infected gastric mucosoid cultures for 24 h at MOI-100, and washed the surface with PBS after the first day to remove free swimming bacteria; to monitor the dynamics of the bacteria, we used an isogenic P12 strain expressing GFP. Infections were terminated after four weeks which by far exceeds any other infection model, especially when using extracellular bacteria. The accumulating mucus containing bacteria was removed regularly but its cultivation on agar plates sporadically formed colonies probably due to the high toxicity of the mucus. Confocal images of the long-term infected monolayers show that the bacteria are highly condensed in clusters of ~5 µm diameter (FIG. 19A). High magnification images show that individual bacteria outside of the clusters have a coccoid shape, reminiscent of the action of defensins [18] (FIG. 19B and enlargement). The relative amount of bacteria vs human cells was monitored every week by qPCR on the respective genomic DNA (FIG. 19C). At d=0 bacteria and cells on the mucosoid cultures were lysed immediately. At d=1 the lysis was done after PBS washing, and every week after removing the mucus. The results indicate that the number of bacteria diminishes with time and that at four weeks may totally disappear (FIG. 19C). However, when we measured the mRNA levels of the pro-inflammatory cytokines TNF-α and IL-8, we noticed that they are only slightly increased at two weeks (FIG. 19D) but become markedly elevated by four weeks of infection (FIG. 19E). Expression of MUC5AC mRNA was drastically reduced at both time points (FIGS. 19D and E). We conclude that our system is able to model the effect of long-term infection and shows persistent inflammation.

To explore how "basal" and "foveolar" gastric mucosoid culture respond to infection, gastric mucosoid culture from the antrum of three patients were cultured for 13 days, before withdrawing WNT3A and RSPO1 from half of the cultures for 5 days. The resulting undifferentiated MUC6$^{hi}$ and foveolar type MUC5AC$^{hi}$ monolayers were infected for 3 days with *Helicobacter pylori* at MOI of 100 then analyzed by qPCR and microarray. No significant changes were observed in the viability of bacteria under +W+R vs −W−R condition (FIG. 20A).

We next focused on the NF-κB-mediated inflammatory response. Upon infection IκBα is normally degraded, allowing p65 to enter the nucleus and activate transcription of κB-responsive genes, including IκBα itself, generating a negative feedback loop. Interestingly, transcription of IκBα was much higher if infection was performed in the +W+R condition compared to −W−R (FIG. 11B), suggesting that the ability of the basal compartment to sense bacteria is considerably higher compared to the foveolae. To confirm this observation, we analyzed all potential NF-κB target genes on our microarray. We used qPCR to validate several important NF-κB-dependent inflammation mediators, including the T-cell-recruiting chemokines 1L8 (CXCL8), CXCL1, CXCL3, CCL20 and IL23A, as well as lymphotoxin B (LTB) (FIG. 20C-H), all of which are only strongly upregulated in response to infection in +W+R medium. *H. pylori* induces expression of TNF-α preferentially in +W+R cultures (FIG. 7H), supporting our observation that the gastric stem cell compartment preferentially responds to infection, while cells in the foveolar compartment remain silent.

Example 12

Figure 21:
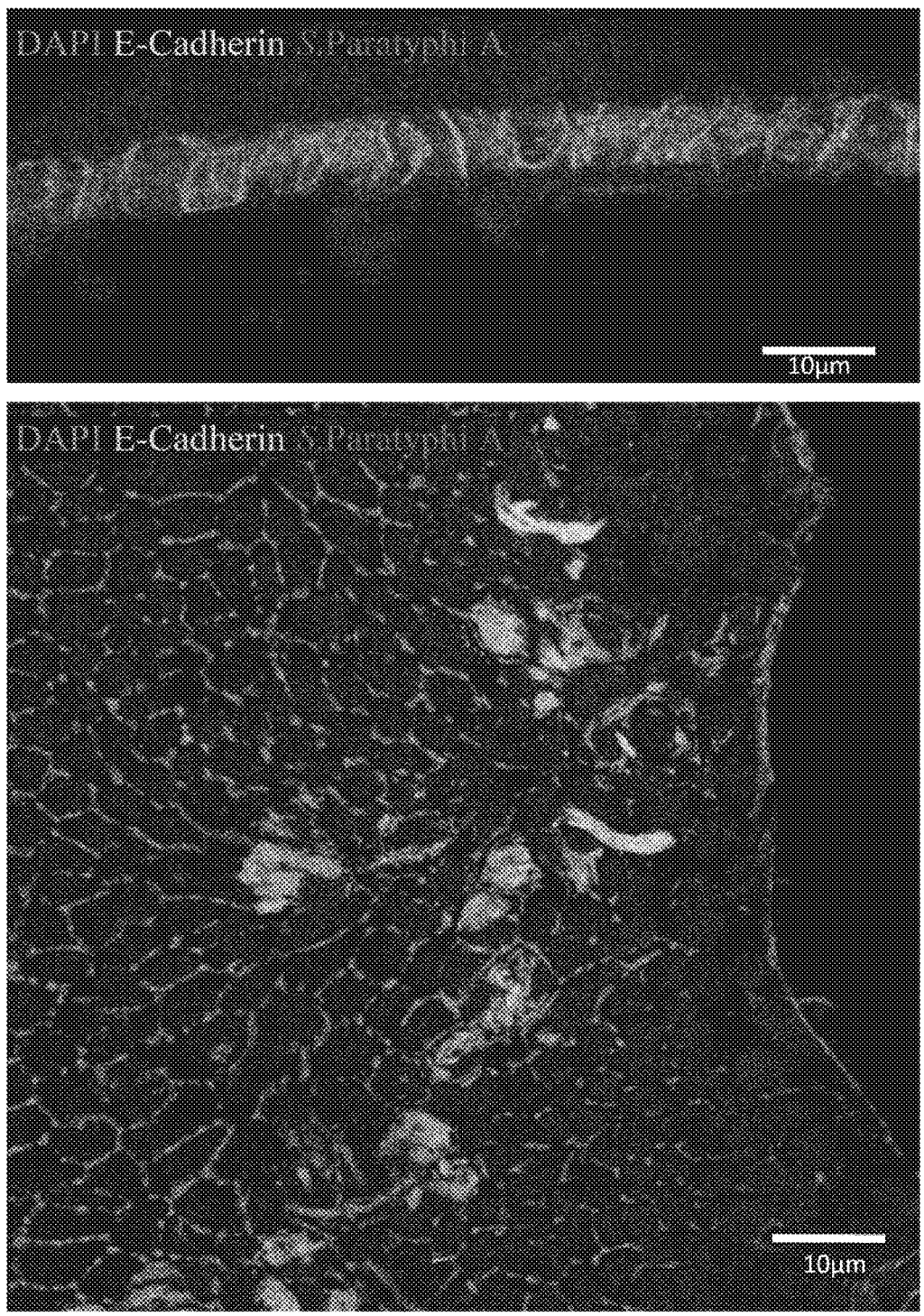

Infection of Gallbladder Derived Mucosoid Culture with *Salmonella Enterica Paratyphi* A FIG. 21 shows a gall bladder derived mucosoid culture infected with *Salmonella enterica Paratyphi* A. The gall bladder mucosoid cultures were infected with the human restricted carcinogenic strain *Salmonella enterica Paratyphi* A. The bacterium used is an isogenic strain expressing mCherry red fluorescent protein. The GBmucosoid cultures were infected 3 weeks after seeding at in 50 ul of medium. The bacteria were kept on the cells for 20 h, then the gentamycin protection assay was performed adding 100 ul of medium supplemented with 100 ug/ml gentamycin in the upper compartment, and 500 ul in the lower. After 1 h of incubation the cells were washed with PBS and the concentration of gentamycin was lowered to 10 ug/ml. No medium was added in the upper compartment. The images were taken 6 days after infection. FIG. 21 shows typical intracellular *salmonella*.

Methods Used in the Examples

Propagation of Cells on Filters

After 13 days cells can be passaged. Top and bottom of inserts are washed twice with PBS, followed by 30-60 min incubation with 0.05% trypsin/EDTA (Thermo Scientific 25300) on both sides of the filter. Cells are harvested, washed, and reseeded at 200,000 cells per new filter.

Infection with *H. Pylori*

*H. Pylori* P12 (strain collection no. P511) and isogenic P12-GFP strain were grown and collected for infection as described before [13]. Bacterial number was determined by measuring the optical density at 550 nm. Infection was carried out in 30 µl of PBS on top of the filters for 6 h to 3 days. Long term infection (2 and 4 weeks) was performed at MOI 100 for one day followed by flushing with PBS and removal of the exceeding mucus every change of media.

Infection with *Salmonella Enterica Paratyphi* A

The Gallbladder mucosoid cultures were infected with the human restricted carcinogenic strain *Salmonella enterica*

*Paratyphi* A. The bacterium used is an isogenic strain expressing mCherry red fluorescent protein. The GBpEM were infected 3 weeks after seeding at in 50 ul of medium. The bacteria were kept on the cells for 20 h, then the gentamycin protection assay was performed adding 100 ul of medium supplemented with 100 ug/ml gentamycin in the upper compartment, and 500 ul in the lower. After 1 h of incubation the cells were washed with PBS and the concentration of gentamycin was lowered to 10 ug/ml. No medium was added in the upper compartment. The images were taken 6 days after infection.

Antibacterial Activity of Mucus

Cells grown in mucosoid cultures (+W+R, 10 days) were either mock infected or infected at MOI-100 with *H. pylori* P12. After 3 days, mucus layer was collected in microcentrifuge tubes. In parallel, *H. pylori* P12-GFP (kanR) were grown on GC agar plates with vancomycin and kanamycin. Bacteria were collected and washed once with PBS, and a suspension containing $\sim 2^{\wedge}10^7$ CFU/ml was prepared in PBS. Aliquots of 5 µl ($\sim 10^5$ CFU) were mixed with 20 µl of fresh mucus collected from mucosoid cultures. After incubation at 37° C., surviving bacteria were enumerated following culture on GC agar plates with vancomycin. To kill wild type bacteria used for cell infection, GC plates also contained kanamycin. Results are expressed as the percentage of bacteria surviving from the initial input.

Transmission Electron Microscopy

For fine structural analysis, mucosoid cultures were fixed in 2.5% glutaraldehyde and postfixed with 0.5% Osmium-tetroxide, contrasted with Uranyl-acetate and tannic acid, dehydrated in a graded ethanol series, and infiltrated in Polybed (Polysciences). Cut out pieces of the filters were stacked in flat embedding molds with Polybed. After polymerization, specimens were cut at 60 nm and contrasted with lead citrate. Specimens were analyzed in a Leo 906E transmission electron microscope (Zeiss, Oberkochen. DE) equipped with a sidemounted digital camera (Morada, SIS-Olympus, Münster, DE).

Test of WNT3A and RSPO1 Conditioned Media

The amount of WNT3A and RSPO1 conditioned media used in the cultivation media is 50% and 25%, respectively. WNT3A and RSPO conditioned supernatant were obtained respectively from the producing cell line LWNT3a and 293T HA Rspo1 Fc 3/3. To standardize the amount of WNT3A and RSPO1 used in the culture both conditioned supernatant were exposed for 24 h to 239T test cells transfected with a 7TCF/LEF promoter-binding site driving the expression of GFP and seeded on a poly-L-lysine coated 48-well. Cell were then fixed for 20 min with PFA 4% and stained with Hoechst. The number of green cells over the number of nuclei representing the "activated cells" is determined automatically from images acquired with an automated microscope (Olympus Soft Imaging Solutions).

The lots of WNT3a conditioned media were used only if 20% to 25% of the conditioned media diluted in DMEM could activate 50% of the test cells. Similarly, the lots of RSPO1 were used only if 5% to 10% of 293T HA Respo1 Fc 3/3 conditioned media could activate 50% of the test cells (5% of LWNT3A conditioned media was used as a coactivator in the RSPO1 test).

Isolation and Culture of Gastric Stromal Cells of the Lamina Propria (GSCs)

A 2×2 cm piece of human gastric antrum was excised directly adjacent to the one used for isolating epithelial glands. The mucosa was placed with the glands facing up and the lamina propria gently scraped off with a scalpel, without disturbing the muscularis mucosa. The scraped off cells containing epithelium and stroma were incubated in 2.6 mM DTT and 50 mM EDTA in PBS (GIBCO, without calcium and magnesium) for 20 min at 37° in a shaking incubator, centrifuged, supernatant removed and cells incubated in 0.05% trypsin for 20 min at 37°. Trypsin was inactivated with a 10-fold larger volume of ADF/10% fetal calf serum (Biochrom S0115) and cell aggregates left to settle by gravity. The supernatant was centrifuged and resuspended in 4 ml ADF/10% FCS/7.5 µM Y-27632 in one well of a 6-well plate for one week until colonies of fibroblastic GSCs appear. GSCs can be propagated indefinitely in ADF/10% FCS by passaging onto fresh plates once cells reach confluency using digestion with 0.05% trypsin as before.

WNT Activation Reporter Assay 239T cells were transfected with a vector containing 7 TCF/LEF binding sites driving the expression of GFP. Cells were seeded on a poly-L-lysine-coated 48-well plate and exposed to different media to test for the presence of WNT activators or inhibitors coming from the gastric stromal cells. The percentage of GFP positive cells was normalized against the total number of nuclei (Olympus Soft Imaging Solutions).

DNA, RNA Isolation and qPCR Analysis

Filters were cut out of the insert and directly transferred to a tube containing 1 ml Trizol (Thermo). After vortexing samples were incubated for 10 min at RT, vortexed again and frozen at −80° C. for long-term storage. 500 µl of chloroform was added to thawed samples before vortexing, incubation for 2 min at RT and centrifugation for 15 min at 4° C. The aqueous phase was mixed with isopropanol, inverted 6× and incubated for 10 min at RT. The sample was transferred to a total RNA isolation Kit column (Thermo) and processed according to the manufacturer's instructions. Total RNA was measured using a NanoDrop and reverse transcription carried out using the Tetro cDNA synthesis Kit (Bioline). DNA was extracted using AllPrep DNA/RNA Mini Kit (Qiagen) according to the manufacturer's instructions; Total DNA was measured using a NanoDrop. qPCR (Step One, Applied Biosystem) was performed using the SensiMix™ SYBR® hi-ROX Kit (Bioline, 3-step cycling according to the manufacturer). Primers are listed in Table 2.

Histology

Filters were fixed overnight in 4% paraformaldehyde at 4° C., washed, embedded orthogonally in Histogel (HG-4000-144) inside a casting mould and paraffinized overnight in a Leica TP1020 tissue processor. The paraffin blocks are generated inside a casting mould on a Paraffin console (Microm). 5 µm sections are cut with a paraffin rotation microtome (Microm). For de-waxing and antigen retrieval, sample slides were washed twice with xylene (10 min), followed by a descending series of alcohols (20 sec each), followed by two washes with water and 30 min in target retrieval solution (Dako) at 95° C., 20 min at room temperature (RT) and 5 min under running water. For whole mount samples, the filters were fixed for 20 min in 4% PFA at 37° C. and washed with PBS. A 10 min cold (−20°) methanol shock was use to permeabilize the sample. Rehydrated samples (whole mount or sections) are washed twice with PBS and incubated with blocking solution (PBS, 1% bovine serum albumin, 2% FCS) for 1 h followed by primary antibody (in blocking solution) for 90 min at RT. After 3 washes with PBS, samples were incubated with fluorescently labeled secondary antibodies and Draq5 (1:1000; Cell Signaling) for 90 min in the dark at RT. The antibodies are listed in Supplementary table 4. Samples were washed three times with PBS, mounted in Mowiol and analyzed by confocal microscopy using a Leica TCS SP-8 microscope. Images were processed, analyzed with FIJI and imported into Adobe Illustrator. Antibodies are listed in Table 3.

Protein Lysates and Immunoblot Analysis

100 µl 2× Laemmli buffer (4% SDS, 20% glycerol, 120 mM Tris-HCl (pH 6.8) and 0.02% bromphenol blue) was added to the filters. Cells were gently scraped with a pipette tip and the lysate transferred to a tube. After addition of 5 µl β-mercapto-ethanol samples were boiled for 5 min at 95° C., separated on a 8% SDS-polyacrylamide gel and transferred to a polyvinylidene difluoride membrane by Western blotting. Membranes were blocked with TBS buffer containing 0.1% Tween-20 and 3% BSA for 2 h and incubated with primary antibodies overnight at 4° C., followed by HRP-conjugated secondary antibodies for 2 h. Membranes were covered with Hyperfilm ECL (Amersham) and signals detected with X-ray films. Antibodies are listed in Table 3.

Monitor of Acid Production by Parietal Cells using Acridine Orange

Three corpus samples were taken at passage 4 in ALI and grown for 13 days in regular medium following by 2 weeks treatment with 50 ng/ml of BMP4 and removal of Noggin and EGF. The Corpus-gEPMs on filters were pre-incubated with 1 µm Acridine Orange for 15 min. The filter was cut out of the insert and mounted with the cells facing the glass on a IBIDI chamber with 400 µl of media (the same with AO). A coverslip was put on top. Images were taken with 25× (Glycerol) for 10 min to stabilize the filter and avoid movements. A solution of 10 µl of 5 mM Histamin in medium was applied on the border of the coverslip while imaging. Fluorescence of acridine orange was excited at 488 nm (3-4%) and images were collected in a time series (10sec) at 500-550 nm and 600-650. Pinhole was opened at 180-190 AU. Images were analyzed by Fiji and corrected for (X-Y) drifts of the sample. Pictures were generated by averaging the signal from 9 time points (90 sec). First and last picture are shown in FIG. 31.

Mass Spectrometry Sample Preparation

The mucus samples were prepared according to the FASP method [19] and following the modification published by Rodriguez-Pineiro et al., (2013) [20]. Samples were diluted with 200 µl M guanidinium hydrochloride in 0.1 M Tris/HCl pH 8.5 (GuHCI) according to another previously published protocol and transferred into MRCFOR030 Microcon-30kDa centrifugal filters. Cysteines were reduced by adding 100 µl 0.1M Dithiothreitol (Sigma-Aldrich D0632) at 60° C. for 15 min and alkylated with 100 µl 0.05 M iodoacetamide (Sigma-Aldrich I6125) at room temperature for 20 min in the dark. After washing two times with 100 µl GuHCl followed by two times 100 µl 50 mM ammonium bicarbonate, 5% acetonitrile the proteins were digested with 0.2 µg sequencing-grade modified trypsin (Promega V5111) in 40 µl overnight at 37° C. After digestion peptide mixtures were acidified with TFA to 0.5% (vol/vol), desalted using ZipTip C18 (Millipore, 0.6 µl bed volume) and then lyophilized.

LC-MS/MS Analysis

The peptides were analyzed using a QExactive Plus mass spectrometer (Thermo Fisher Scientific) coupled on line to a Dionex UltiMate 3000 RSLC nano system (Thermo Fisher Scientific). After solubilization in 13 µl 2:98 (v/v) acetonitrile/water containing 0.1% TFA, 10 µl of each sample was loaded on a C18 PepMap 100 trap column (300 µm×5 mm; 5 µm particle size 100 Å pore size; Thermo Fisher Scientific) at a flow rate of 20 µl/min 2:98 (v/v) acetonitrile/water containing 0.1% TFA for pre-concentration and desalting. Separation was performed using an Acclaim C18 PepMap RSLC column (75 µm×250 mm; 2 µm particle size 100 Å pore size; Thermo Fisher Scientific) at a flow rate of 300 nl/min. HPLC solvent A was 0.1% (v/v) FA and peptides were eluted from the column using HPLC solvent B 80:20 (v/v) acetonitrile/water containing 0.1% FA starting from 3%, increasing to 40% in 45 minutes, and to 98% in 5 minutes. The peptides were analyzed in data-dependent acquisition mode that alternated between one MS scan and 10 MS/MS scans for the most abundant precursor ions. MS scans were acquired over a mass range of m/z 350-1600 and resolution was set to 70000. Peptides were fragmented using HCD at 27% normalized collision energy and measured in the orbitrap at a resolution of 17500.

Protein Identification

Proteins were identified and quantified using the Max-Quant software (Version 1.601) [21] [22] searching against the SwissProt human sequence database (released Jul. 11, 2017, 20214 entries). Searches were performed using the following parameters:

max. missed cleavages 2; variable modifications Oxidation (M); Acetyl (Protein N-term); pyro-Glu (Gln) and carbamidomethylation of cysteines as fixed modification. The false discovery rate was set to 0.01 for proteins, peptides and modified sites.

TABLE 2

| | Sequence (5'->3') |
|---|---|
| CXCL1-3 | |
| Forward Primer | CGCCCAAACCGAAGTCATAG |
| Reverse Primer | GCTCCCCTTGTTCAGTATCTTTT |
| CCL20 | |
| Forward Primer | TGCTGTACCAAGAGTTTGCTC |
| Reverse Primer | CGCACACAGACAACTTTTTCTTT |
| LTB | |
| Forward Primer | GTACGGGCCTCTCTGGTACA |
| Reverse Primer | GTCCACCATATCGGGGTGAC |
| IL23A | |
| Forward Primer | CTCAGGGACAACAGTCAGTTC |
| Reverse Primer | ACAGGGCTATCAGGGAGCA |
| KRT19 | |
| Forward Primer | GTCACAGCTGAGCATGAAAGC |
| Reverse Primer | AGCTGGGCTTCAATACCGC |
| KRT18 | |
| Forward Primer | TTCTGGGGGCATGAGCTTCAC |
| Reverse Primer | GCGCCTGCATAGACGCTG |
| KRT8 | |
| Forward Primer | GCTGGCCGTAAACTGCTTTG |
| Reverse Primer | ACATTTGGCAGCCAGCTTTG |
| EPCAM | |
| Forward Primer | GCTGGCCGTAAACTGCTTTG |
| Reverse Primer | ACATTTGGCAGCCAGCTTTG |
| CDH1 | |
| Forward Primer | TACCCTGGTGGTTCAAGCTG |
| Reverse Primer | CCTGACCCTTGTACGTGGTG |

TABLE 2-continued

Sequence (5'->3')

LGR5

Forward Primer CTCCCAGGTCTGGTGTGTTG
Reverse Primer GCTCGCAATGACAGTGTGTG

CTNNB

Forward Primer AGCAATTTGTGGAGGGGGTC
Reverse Primer AGCAGCTGCACAAACAATGG

CD44

Forward Primer AGCACCATTTCAACCACACC
Reverse Primer GCAGTGGTGCCATTTCTGTC

PGC

Forward Primer TGTCTTTGGGGGTGTGGATAG
Reverse Primer ATGAGGTAACTCTTCAATGCCAATC

MUC6

Forward Primer CAGCTCAACAAGGTGTGTGC
Reverse Primer TGGGGAAAGGTCTCCTCGTA

MUC5AC

Forward Primer GGAGGTGCCCACTTCTCAAC
Reverse Primer CTTCAGGCAGGTCTCGCTG

CHGA

Forward Primer CCAAGGAGAGGGCACATCAG
Reverse Primer TCTTCCACCGCCTCTTTCAG

ATP4b

Forward Primer TGGGTGTGGATCAGCCTGTA
Reverse Primer CTGGTCTTGGTAGTCCGGTG

IL-8

Forward Primer ACACTGCGCCAACACAGAAAT
Reverse Primer ATTGCATCTGGCMCCCTACA

TNF

Forward Primer TCCCCAGGGACCTCTCTCTA
Reverse Primer GAGGGTTTGCTACAACATGGG sFRP1

Forward Primer ACGTGGGCTACAAGAAGATGG
Reverse Primer CAGCGACACGGGTAGATGG sFRP2

Forward Primer 1 ACGTGGGCTACAAGAAGATGG
Reverse Primer 1 CAGCGACACGGGTAGATGG sFRP2

Forward Primer 2 CTGGCCCGACATGCTTGAG
Reverse Primer 2 GCTTCACATACCTTTGGAGCTT sFRP3

Forward Primer 2 ACACAGACTTACAGGGCTTGAT
Reverse Primer 2 GAGCCCATACTCATCPGTACCG sFRP4

Forward Primer CCTGGAACATCACGCGGAT
Reverse Primer CGGCTTGATAGGGTCGTGC

TABLE 2-continued

Sequence (5'->3')

sFRP5

Forward Primer AGGAGTACGACTACTATGGCTG
Reverse Primer GGTCGGCAGGGATGTCAAG

DKK1

Forward Primer CCTTGAACTCGGTTCTCAATTCC
Reverse Primer CAATGGTCTGGTACTTATTCCCG

DKK2

Forward Primer CTCACAGATCGGCAGTTCG
Reverse Primer ATGCCAGTCCTTGGTACATGC

DKK3

Forward Primer 1 AGGACACGCAGCACAAATTG
Reverse Primer 1 CCAGTCTGGTTGTTGGTTATCTT

DKK3

Forward Primer 2 ACGAGTGCATCATCGACGAG
Reverse Primer 2 GCAGTCCCTCTGGTTGTCAC

DKK4

Forward Primer ACGGACTGCAATACCAGAAAG
Reverse Primer CGTTCACACAGAGTGTCCCAG

DKKL1

Forward Primer CTCTACCCTGGTGATCCCTC
Reverse Primer CGAAGCAGGTTACCTTTCAGGA

USAG1

Forward Primer GCCATCAGAGATGTATTTGGTGG
Reverse Primer GTGCTCCCTAACTGGATTGGA

WIF1

Forward Primer TCTCCAAACACCTCAAAATGCT
Reverse Primer GACACTCGCAGATGCGTCT

BARX1

Forward Primer TTCCACGCCGGACAGAATAGA
Reverse Primer AGTAAGCTGCTCGCTCGTTG

TFF2

Forward Primer CGGGGAGTGAGAAACCCTC
Reverse Primer CACTGGAGTCGAAACAGCATC

GAPDH

Forward Primer GGTATCGTGGAAGGACTCATGAC
Reverse Primer ATGCCAGTGAGCTTCCCGTTCAG rDNA 16s *H. pylori*

Forward Primer TTTGTTAGAGAAGATAATGACGGTATCTAAC
Reverse Primer CATAGGATTTCACACCTGACTGACTATC gDNA hGAPDH Forward Primer GACTTCAACAGCGACACCC
Reverse Primer AGAAGATGAAAAGAGTTGTCAGGGC

TABLE 3

| Antibody | dilution | manufacturer | code |
|---|---|---|---|
| Histology | | | |
| H+,K+ ATPase beta | 1:200 | Abcam | ab2349 |
| Occludin | 1:200 | Invitrogen | 331500 |
| Pepsinogen II | 1:100 | Abcam | ab9013 |
| CagA-b300 | 1:200 | SCBT | sc-25760 |
| E-Cadherin | 1:100 | BD Bioscience | 610181 |
| KI67 | 1:100 | Cell Signaling | 9027 |
| MUC6 | 1:100 | Abcam | ab49462 |
| Cromogranin A | 1:100 | Abcam | ab15160 |
| MUC5AC | 1:100 | Abcam | ab3649 |
| β-Catenin | 1:100 | Sigma-Aldrich | C2206 |
| Western Blot | | | |
| CagA-b300 | 1:200 | SCBT | sc-25760 |
| pTyr PY99 | 1:500 | SCBT | sc-7020 |
| β-actin | 1:5000 | Sigma | A5441 |

FIGURE LEGENDS

FIG. 1. Schematic of mucosoid culture method: cells are seeded at confluent density onto polycarbonate filters of well inserts placed in a 24-well plate and the medium above the cell layer is withdrawn after 3 days to initiate air-liquid interface culture.

FIG. 2. (top right) top view of a mucosoid culture showing that occludin is present in all cell junctions. (top left) IF image of a lower section of the same monolayer showing basal re-arrangement of apical occludin around cells organized into a rosette-like structure. (bottom) IF labelling against occludin shows that cells are apically connected by tight junctions.

FIG. 3. 1 day after seeding, cells have formed a confluent monolayer. On day 3 they have increased in height and medium above the cells is removed. The height and polarization of the cell layer continues to increase and on day 10 a layer of mucin is present on the surface. Monolayer height was measured using FIJI software FIG. 4. (top) H&E staining of a mucosoid culture section shows basal distribution of the nuclei. (bottom) IF labelling with Ki67 antibody marks proliferating cells in mucosoid cultures at 2 weeks of culture FIG. 5. (top) Staining of a section of Colon pEM (CpEM) with the typical colon mucin marker MUC2 and b-Catenin which stains the membranes and partially the nuclei. (bottom) Staining of a section of Colon mucosoid culture with Ki67 showing the highly proliferative phenotype of the colon epithelium FIG. 6. (top) Immunostaining of a Gall Bladder mucosoid culture section showing a columnar epithelium similar to the one in the organ. (bottom) Whole mount immunostaining of a Gall Bladder mucosoid showing the same culture from a top view.

FIG. 7. (top) Optical section of a Fallopian Tube mucosoid culture showing the ciliated cells and the typical FT marker CA125 the ciliated cells of the Fallopian tube are contributing to the propulsion of gametes and embryos in the genital tract. (mid top) Nuclear b-catenin antibody staining of FTpEM shows strong activation of the WNT/b-catenin pathway in FTpEM. (mid bottom) Nuclear presence of PAX8 indicate presumptive stem cells in the FTpEM. (bottom) Ki-67 antibody staining of FTpEM indicate the mild proliferative phenotype of the FTpEM in vitro.

FIG. 8. mRNA expression levels of genes specific for epithelial (top), stem (mid) and gland cells (bottom) determined from two parallel mucosoid cultures over 8 passages (6 months), as determined by qPCR. ΔCt=difference between the ct of each gene compared to GAPDH FIG. 9. (top) Few granules in the cells from (+W+R) antrum-mucosoid cultures are positive for MUC5AC IF labelling apically. (bottom) IF labelling against chromogranin A showing positive granules on the basal side of hormone producing enteroendocrine cells of an antral mucosoid culture.

Figure 10:
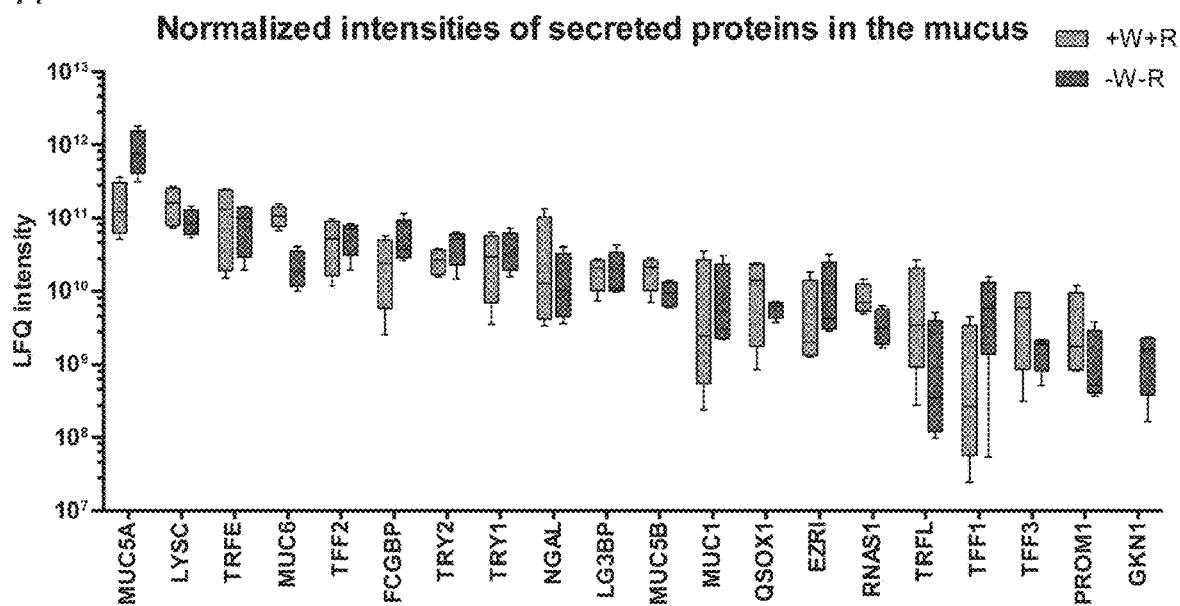
Figure 10:
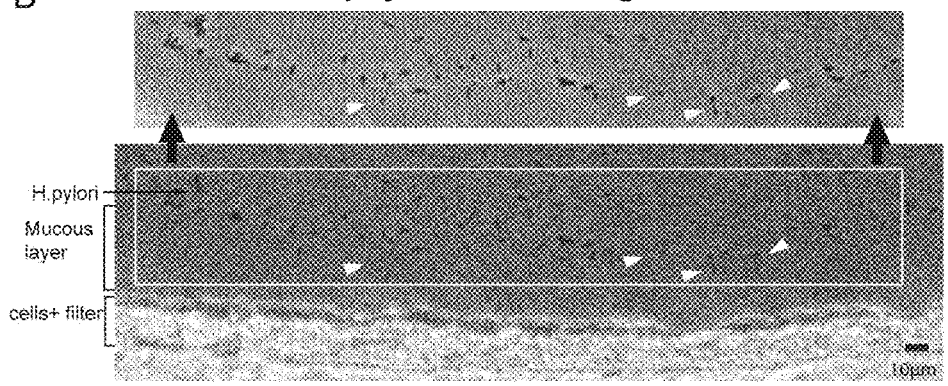
Figure 10:
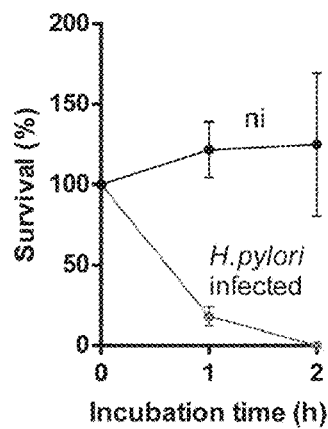

FIG. 10. (A) Proteome analysis of the total mucus produced by four antral mucosoid culture samples revealed differential secretion of mucins, secreted enzymes and other proteins comparing +W+R vs −W−R. Wnt and RSPO were removed for five days. Box and whiskers plot represent the average and min/max of normalized label free quantification signal (LQF) calculated with MaxQuant software (four mucus sample per condition). Only highly secreted proteins with more than two unique peptides in the four condition, with the highest normalized intensity and highest score (>250) and detected in mucus derived from all four antral mucosoid cultures are shown in the graph. (B) Paraffin section of a mucosoid culture infected with P12 at MOI 50 for 72 h. The bright layer indicates the cell layer. The bacteria are mostly bound to a continuous mucus layer that only a few have managed to infiltrate (arrowheads). (C) Mucus was harvested from mucosoid cultures infected with P12 at MOI 100 or uninfected controls, centrifuged to remove bacteria and used to plate the kanamycin resistant isogenic strain P12-GFP for 1 and 2 hours. The sample was plated on kanamycin plates and colonies counted relative to the number of bacteria plated. Results represent % of colony compared to the input +/−SD of three mucus samples.

Figure 11:
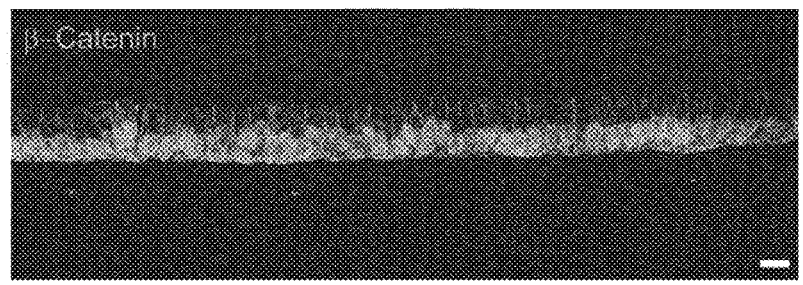
Figure 11:
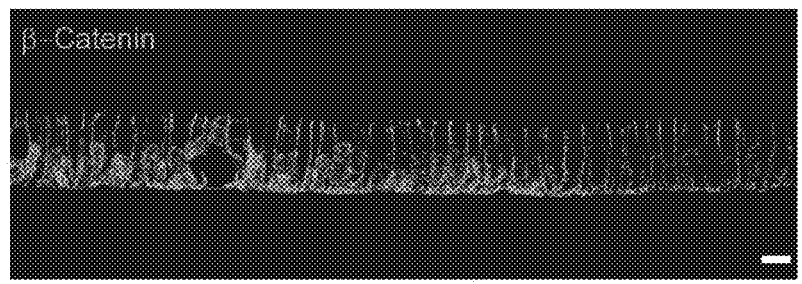

FIG. 11. (left) IF labelling against β-catenin showing universal nuclear localization in +W+R condition. (right) β-catenin is absent from the nucleus after W/R are withdrawn for 6 days.

FIG. 12. (A)(B) Withdrawal of W/R is also accompanied by an increased number of cells positive for the proliferation marker Ki67 and an increase in height. (C)(D) Quantification of the Ki67 positive cells and of the cell density after withdrawal of W/R from 8 sections n>400. (E) LGR5 determined by qRT-PCR relative to that in +W+R medium. Bars represent the mean of three.

FIG. 13. (left): Mucosoid cultures were cultured for 30 days in +W+R medium before passaging into Matrigel cultures in +W+R medium to grow organoids. Shown is a representative images of three independent cultures. (center): Mucosoid cultured for 6 days in +W+R medium followed by removal of Wnt3A and RSPO1 for 12 days, followed by a further 12 days in +W+R medium leads to a drastic reduction of organoid survival. (right): cells cultured without Wnt3A and RSPO1 did not generate any organoids FIG. 14. (A-top) IF labelling against the foveolar marker MUC5AC shows that expression is low in the +W+R condition and increases after W/R are withdrawn for 6 days (−W−R). (A-middle) In contrast, expression of the basal marker MUC6 is high in the +W+R condition and reduces dramatically after W/R are withdrawn for 6 days (−W−R). (A-bottom) EM micrograph of antral mucosoid culture under +W+R condition showing MUC6 enriched apical mucus granules higher accumulation and secretion of MUC5AC enriched granules in antral mucosoid cultures under −W−R condition. (B) qRT-PCR analysis shows that relative mRNA levels of MUC5AC are higher upon W/R withdrawal, whereas levels of MUC6 are high in +W+R. Bars represent mean ±standard deviation of 2 independent experiments *p<0.05.

FIG. 15. (A)(B) Whole mount staining IF labelling against subunit B of the H+/K+ ATPase hydrogen pump (ATP4B) marks increasing acid-producing parietal cells in a corpus-stomach mucosoid culture after treatment with 50 ng/ml BPM4 for 2 weeks in the absence of Noggin and EGF. (C) Quantification of the ATP4B positive cells performed on three independent corpus-stomach mucosoid culture after 2 weeks of BMP4 induction. Bars shows mean and SD. (D) An electron micrograph of a parietal cells in corpus-gEPMs after 2 weeks of BMP4 induction: apical accumulation of mitochondria and tubulovesicles is a reminiscence of parietal cells. (E) corpus-stomach mucosoid culture cultivated with 50 ng/ml of BMP4 are pre-incubated with 1 µM of Acridine Orange for 15 min 37° C./5% CO2 and activated with 10 µl of 5 mM Histamin solution. Fluorescence of acridine orange was excited at 488 and images were collected in a time series (every 10 sec) at 500-550 nm and 600-650.

FIG. 16. Antral mucosoid cultures derived from 3 different patients were cultivated for 13 days. Parallel samples were differentiated by excluding Wnt3A and RSPO1 from the culture for 5 days (A)(B) treatment with 10 µg/ml TNF-α or 5 µg/ml IL-1β for 3 days. Expression of IL-8 was analysed by qPCR and normalized to untreated control cells in +W+R medium. ns: not significant; *p<0.005, unpaired t-test. Error bars represent min and max values from technical replicates.

FIG. 17. (A) Schematic of a gastric gland showing the position of the stroma of the lamina propria from which the isolated GSCs originate. (B) Filters containing antral mucosoid cultures were moved to wells containing GSCs and co-cultured for 6 days, or alternatively cultured with 50% of identical medium conditioned by GSCs. Levels of LGR5 mRNA expression were measured by qPCR and expressed relative to the +W+R condition; Bars represent mean±SEM of three independent biological replicates; * p<0.05, **** p<0.00005, unpaired t-test. (C) 293T cells transfected with a 7×binding site for TCF driving GFP expression were used to measure activation of the Wnt pathway. GSCs-conditioned medium was titrated in the constant presence of 50% LWnt3A-conditioned medium. (D-E) mucosoid cultures cultured in −W−R medium show almost no nuclear p-catenin (D) but highly express MUC5AC (E). (F-G) Antral mucosoid cultures cultured in +W+R medium exhibit nuclear β-catenin (F) but express almost no detectable MUC5AC (G). (H-I) After 6 days of co-culture with GSCs in the presence of +W+R β-catenin is no longer localized to the nuclei (H) and MUC5AC is expressed again (I). (J) Expression of soluble Wnt inhibitors in GSCs as detected by RT-PCR. Expression of SFRP2 and DKK3 was tested with primers against two different exon-spanning regions.

FIG. 18. (A) stomach mucosoid cultures infected for 72 h at MOI 50 labelled with antibody against CagA showing groups of bacteria that have not yet adhered to the cells (*) or adherent to the surface (**). (B) Western blot analysis of phosphorylated CagA detected with an antibody against phosphorylated tyrosine (PY99) in cell lysates from non-infected cells (left lane), antral mucosoid cultures infected with P12 at MOI 200 for 72 h (middle lane), and the same cells seeded as planar monolayers on collagen-coated plastic infected for 18 h at MOI 25 (right lane). (C) left panel: EM micrograph of an antral mucosoid culture showing the interaction between the microvilli and foci of coccoid shaped bacteria 24 h after infection: right panel: a helical bacterium adhering on the apical surface 6 h after infection. P12-GFP MOI=100.

Figure 19:
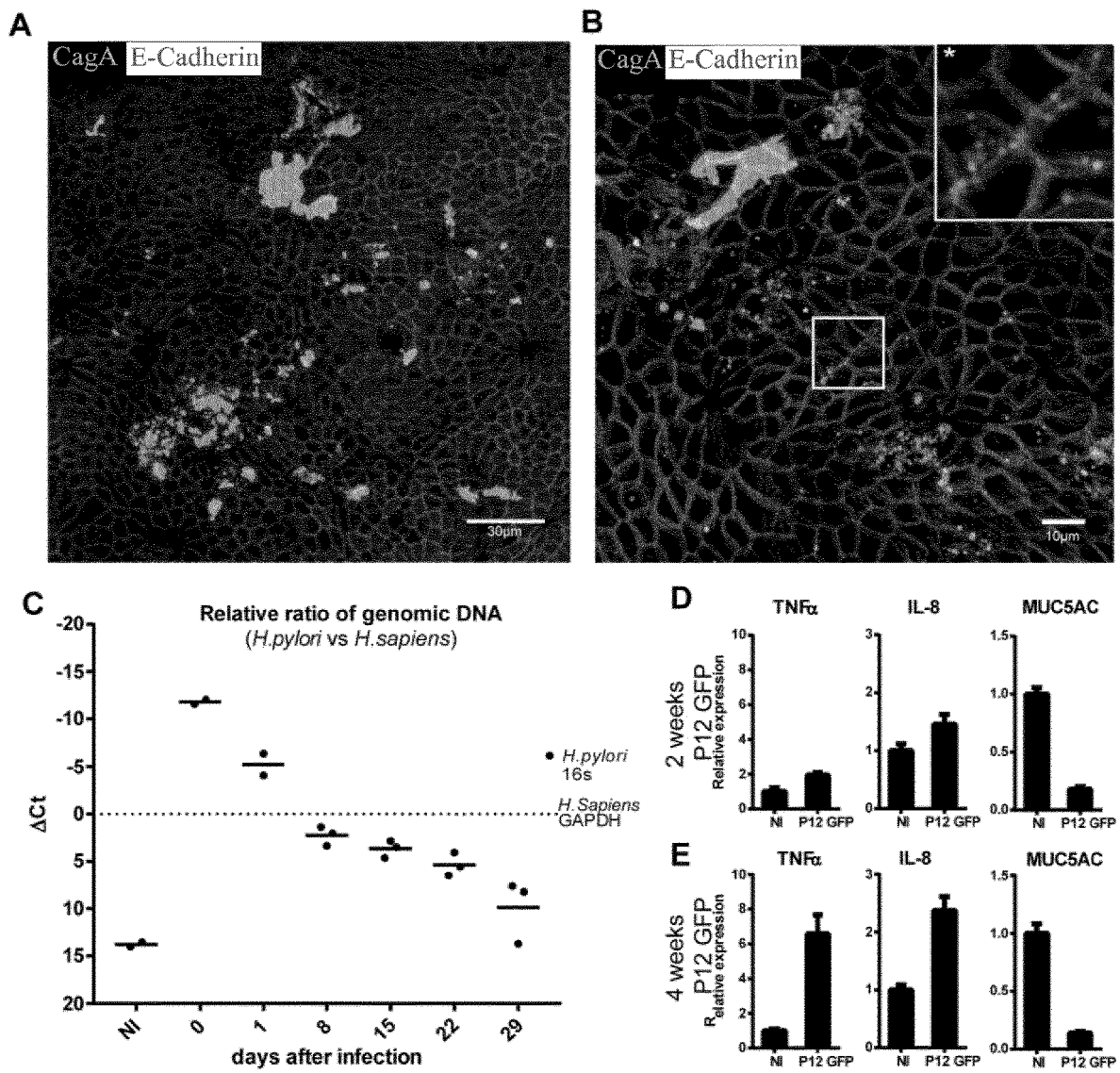

FIG. 19. Stomach mucosoid cultures were infected with the isogenic H. pylori strain P12-GFP at MOI 100. 24 h later the surface was rinsed twice with PBS and mucus removed every three to four days. (A) After two weeks, filters were fixed and labelled with antibodies against cagA and E-cadherin followed by whole mount IF. (B) higher magnification image and detail (*) enlarged in top right corner of the same infection as in (A). (C) The relative amount of P12-GFP to the host cells was calculated by qPCR comparing the abundance of the 16s ribosomal DNA sequence vs the one of human GAPDH. NI=non infected; Day=0 DNA was collected directly after application of bacteria; day=1 DNA was collected after washing with PBS ΔCt=difference between the ct of each gene compared to hGAPDH, the horizontal sign is the average of the values represented by the dots, each dot is one replicate. (D,E) Expression of TNF-α, IL-8 and MUC5AC was analysed by qPCR after 2 and 4 weeks of infection and normalized to non-infected control.

Figure 20:
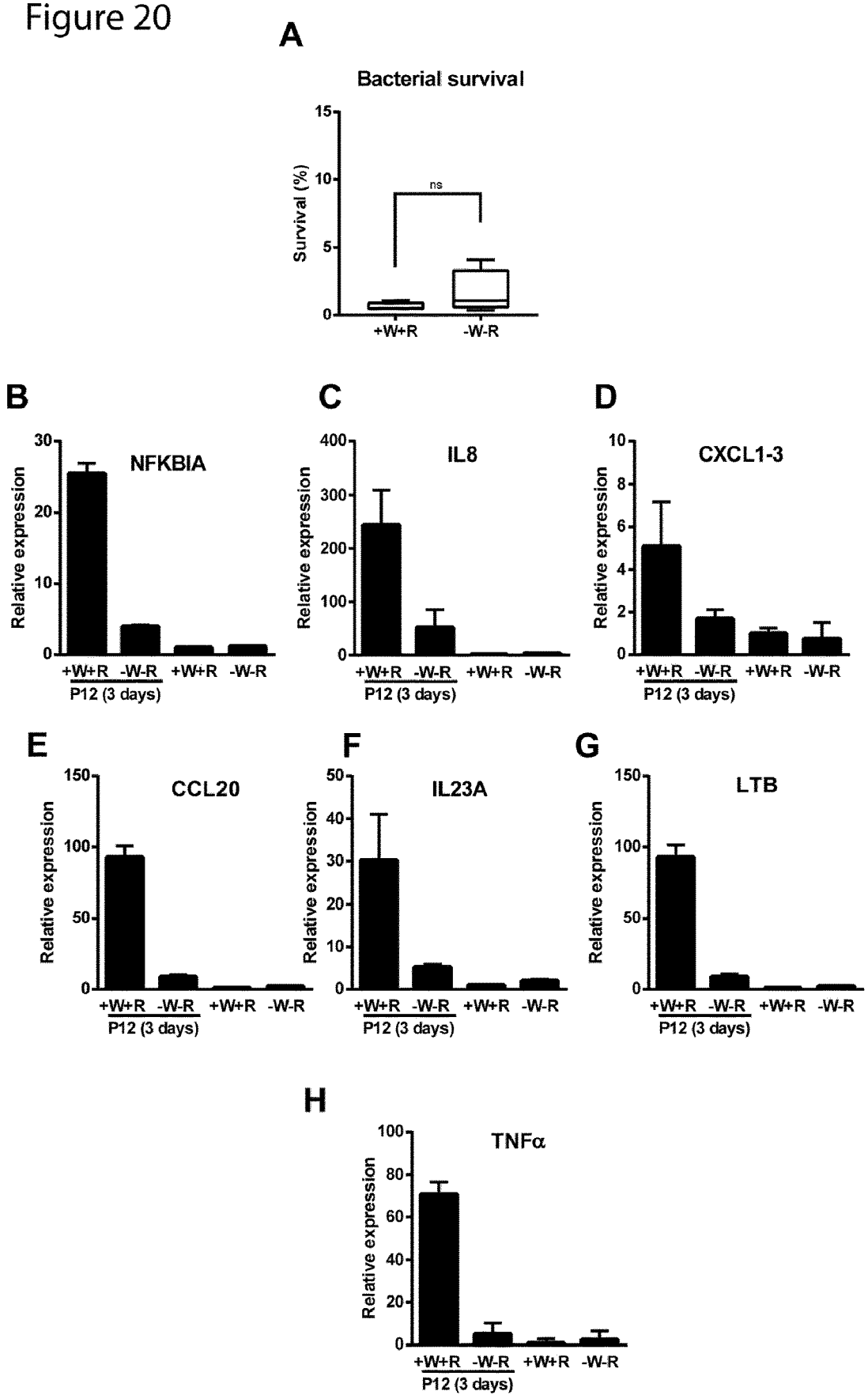

FIG. 20. (A) Survival of bacteria (P12) when infecting +W+R antral mucosoid cultures (MOI=25) compared to −W−R (four different samples per condition) expressed as percentage of input. (B-I) Antral mucosoid cultures derived from 3 different patients were cultivated for 13 days. Parallel samples were differentiated by excluding Wnt3A and RSPO1 from the culture for 5 days, followed by infection with P12 for 3 days at MOI 100. (B-H) Expression of IκB□ (NFKBIA) IL8, CXCL1-3 CCL20 IL23A LTB TNFa was analysed by qPCR and normalized to non-infected control cells in +W+R. Results shown are representative for two biological replicates. Results shown are representative of two biological replicates.

FIG. 21. Gallbladder mucosoid culture infected with *Salmonella Paratyphi* A. The bacterium used is an isogenic strain expressing mCherry red fluorescent protein. The gallbladder mucosoid cultures were infected with an MOI of 100 3 weeks after seeding at in 50 ul of medium. The bacteria were kept on the cells for 20 h, then the gentamycin protection assay was performed adding 100 ul of medium, supplemented with 100 ug/ml gentamycin in the upper compartment and 500 ul in the lower. After 1 h of incubation the cells were washed with PBS and the concentration of gentamycin was lowered to 10 ug/ml. No medium was added in the upper compartment. The images were taken 6 days after infection. The images show infected gallbladder mucosoid cultures with intracellular bacteria from a side view (top) and from a top view (bottom)

REFERENCES

1. Nossol, C., et al., *Air-liquid interface cultures enhance the oxygen supply and trigger the structural and functional differentiation of intestinal porcine epithelial cells (IPEC).* Histochem Cell Biol, 2011. 136(1): p. 103-15.

2. Yokoyama, F., et al., *Differentiation of gastric surface mucous cells (GSM06) induced by air-liquid interface is regulated partly through mitogen-activated protein kinase pathway.* J Gastroenterol Hepatol, 2007. 22(12): p. 2310-5.

3. Ootani, A., et al., *Foveolar differentiation of mouse gastric mucosa in vitro.* Am J Pathol, 2003. 162(6): p. 1905-12.

4. Butor, C. and J. Davoust, *Apical to basolateral surface area ratio and polarity of MDCK cells grown on different supports.* Exp Cell Res, 1992. 203(1): p. 115-27.

5. Schlaermann, P., et al., *A novel human gastric primary cell culture system for modelling Helicobacter pylori infection in vitro.* Gut, 2014.

6. Bartfeld, S., et al., *In vitro expansion of human gastric epithelial stem cells and their responses to bacterial infection.* Gastroenterology, 2015. 148(1): p. 126-136.e6.

Khurana, S. S., et al., *The hyaluronic acid receptor CD44 coordinates normal and metaplastic gastric epithelial progenitor cell proliferation.* J Biol Chem, 2013. 288(22): p. 16085-97.

8. Kessler, M., et al., *The Notch and Wnt pathways regulate sternness and differentiation in human fallopian tube organoids.* Nature communications, 2015. 6: p. 8989-8989.

9. Gudipaty, S. A. and J. Rosenblatt, *Epithelial cell extrusion: Pathways and pathologies.* Semin Cell Dev Biol, 2017. 67: p. 132-140.

10. Madara, J. L., *Maintenance of the macromolecular barrier at cell extrusion sites in intestinal epithelium: physiological rearrangement of tight junctions.* J Membr Biol, 1990. 116(2): p. 177-84.

11. Barker, N., et al., *Lgr5(+ve) stem cells drive self-renewal in the stomach and build long-lived gastric units in vitro.* Cell Stem Cell, 2010. 6(1): p. 25-36.

12. Srinivasan, B., et al., *TEER measurement techniques for in vitro barrier model systems.* J Lab Autom, 2015. 20(2): p. 107-26.

13. Schlaermann, P., et al., *A novel human gastric primary cell culture system for modelling Helicobacter pylori infection in vitro.* Gut, 2016. 65(2): p. 202-13.

14. Choi, E., et al., *Cell lineage distribution atlas of the human stomach reveals heterogeneous gland populations in the gastric antrum.* Gut, 2014. 63(11): p. 1711-20.

15. Nordman, H., et al., *Gastric MUC5AC and MUC6 are large oligomeric mucins that differ in size, glycosylation and tissue distribution.* Biochem J, 2002. 364(Pt 1): p. 191-200.

16. Babu, S. D., et al., *Expression profile of mucins (MUC2, MUC5AC and MUC6) in Helicobacter pylori infected pre-neoplastic and neoplastic human gastric epithelium.* Mol Cancer, 2006. 5: p. 10.

17. McCracken, K. W., et al., *Wnt/beta-catenin promotes gastric fundus specification in mice and humans.* Nature, 2017. 541(7636): p. 182-187.

18. Bauer, B., et al., *The Helicobacter pylori virulence effector CagA abrogates human beta-defensin 3 expression via inactivation of EGFR signaling.* Cell Host Microbe, 2012. 11(6): p. 576-86.

19. Wisniewski, J. R., et al., *Universal sample preparation method for proteome analysis.* Nat Methods, 2009. 6(5): p. 359-62.

20. Rodriguez-Pineiro, A. M., et al., *Studies of mucus in mouse stomach, small intestine, and colon. II. Gastrointestinal mucus proteome reveals Muc2 and Muc5ac accompanied by a set of core proteins.* Am J Physiol Gastrointest Liver Physiol, 2013. 305(5): p. G348-56.

21. Cox, J. and M. Mann, *MaxQuant enables high peptide identification rates, individualized p.p.b.-range mass accuracies and proteome-wide protein quantification.* Nat Biotechnol, 2008. 26(12): p. 1367-72.

22. Tyanova, S., T. Temu, and J. Cox, *The MaxQuant computational platform for mass spectrometry-based shotgun proteomics.* Nat Protoc, 2016. 11(12): p. 2301-2319.

The invention also includes following aspects. The features of these aspects also apply to any other aspect or/and embodiment disclosed herein. It is intended that the features of these aspects can be combined with any other aspect or/and embodiment disclosed herein:

1. A method of culturing columnar epithelial cell on a solid-semi-permeable surface.
2. The method includes ALI.
3. The cells propagate on the filters.
4. The cells form a coherent monolayer.
5. The culture comprises stem cells.
6. The stem cells in the cultures can regenerate.
7. The mucosoid culture can be expanded to further culture by single cell dissociation.
8. The stem cells in the cultures are capable of multi-neage-differentiation.
9. The cells resulting from the mucosoid cultures comprise different lineages.
10. The cells resulting from the mucosoid cultures can be ciliated.
11. The cells resulting from the mucosoid cultures can secrete.
12. The cells resulting from the mucosoid cultures can absorb.
13. The cells of the mucosoid cultures are polarized.
14. The cells of the mucosoid cultures are tall.
15. The cells of the mucosoid cultures produce mucus on the apical side.
16. The cells of the mucosoid cultures can absorb substances from the basal or from the apical side.
17. The cells of the mucosoid cultures can transport substances from the apical side to the basal side and vice-versa.
18. The mucosoid cultures are a source of mucus.
19. The mucosoid cultures are a source of cells.
20. The mucosoid cultures are a source of molecules in the secreted media.
21. Mucus cells and molecules in the media can be analyzed by conventional method.
22. Mucus cells and molecules in the media can be a source for production of molecules.
23. The mucus can be used as a medicament or as a vehicle of drugs.
24. The cells can be used in regenerative medicine.
25. The mucosoid cultures can be co-cultured with other non-epithelial cells.
26. The mucosoid cultures can be co-cultured with bacteria, parasites and viruses or with part of them.
27. The mucosoid cultures respond to physical, chemical or biological stimulations.
28. The response to the stimulation includes inflammation, differentiation, proliferation, migration, metabolism, transport, secretion, absorption, repair.

Furthermore, the invention also includes following aspects. The features of these aspects also apply to any other aspect or/and embodiment disclosed herein. It is intended that the features of these aspects can be combined with any other aspect or/and embodiment disclosed herein:

1. A method of culturing an epithelial cell on a solid surface, comprising the steps:
   (a) providing an epithelial cell,
   (b) contacting the epithelial cell with a solid surface,
   (c) culturing the cell of (b) under air-liquid interface conditions,
   (d) optionally (i) obtaining the cell cultured in step (c), and (ii) repeating steps (b) and (c), and
   (e) obtaining the cell culture of (c),
   wherein the cell culture obtained in step (e) comprises an epithelial monolayer on the solid surface, wherein the epithelial cells are polarized columnar epithelial cells.

2. A method of culturing an epithelial cell on a semi-permeable surface, comprising the steps:
   (a) providing an epithelial cell,
   (b) contacting the epithelial cell with a semi-permeable surface, (c) culturing the cell of (b) under air-liquid interface conditions,
(d) optionally (i) obtaining the cell culture in step (c) or (ii) repeating steps (b) and (c), and
(e) obtaining the cell culture of (c),
wherein the cell culture obtained in step (e) comprises an epithelial monolayer on the solid surface, wherein the epithelial cells are polarized columnar epithelial cells.

3. A method for long term culture of mammalian columnar epithelial cells comprising
(a) providing an epithelial cell, and
(b) culturing mammalian tissue on a semi-permeable solid surface under air-liquid interface condition, wherein the cell culture obtained comprises an adjoining epithelial monolayer on the surface, wherein the epithelial cells are polarized, wherein the basal side is adjacent to the surface, wherein the culture provides stem cells able of multilineage differentiation, that maintains the ultrastructure and differentiation markers characteristic of the tissue.

4. The method of any one of the Items 1 to 3, wherein the solid surface, the semi-permeable surface or the semi-permeable solid surface is a porous surface.

5. The method of Item 4, wherein the pores in the porous surface have a pore size so that during culture, the cells do not pass through the porous surface, in particular through the carrier comprising the porous surface.

6. The method of Item 4 or 5, wherein the pores have a size in the range 0.2 µm to 1 µm, in particular a size of about 0.4 µm.

7. The method of any one of the preceding Items, wherein the surface is a polycarbonate surface, a polycarbonate filter, or a polyethylene terephthalate (PET) surface.

8. The method of any one of the preceding Items, wherein the cells in the cell culture obtained exhibit stemness, in particular, the cells maintain their stemness potential at least partially.

9. The method of any one of the preceding Items, wherein the cells in the cell culture obtained are capable of cellular differentiation, in particular into particular lineages.

10. The method of any of the preceding Items, wherein the polarized columnar epithelial cells comprise a basal side faced to the solid surface, and an apical side.

11. The method of Item 10, wherein the epithelial cells produce mucus on the apical side.

12. The method of Item 10 or 11, wherein the epithelial accumulate mucus on the apical side.

13. The method of any one of the Items 10 to 12, wherein the cells are connected by tight junctions on the apical side.

14. The method of any one of the preceding Items, wherein the epithelial cell provided in step (a) is selected from gastric mucosa cells, colon mucosa cells, gallbladder mucosa cells, and fallopian tube mucosa cells.

15. The method of any one of the preceding Items, wherein the epithelial cell provided in step (a) is isolated from tissues with a columnar epithelium lining, in particular from stomach, colon, gall bladder and fallopian tube.

16. The method of any one of the preceding Items, wherein WNT signaling is activated in the cells.

17. The method of Item 16, wherein WNT signaling is activated by WNT3A or/and RSPO1.

18. The method of Item 16 or 17, wherein the epithelial cell provided in step (a) is a gastric mucosa cell.

19. The method of Item 18, wherein the cell culture obtained in step (e) comprises cells exhibiting a phenotype of a gastric gland base cell.

20. The method of Item 18 or 19, wherein the cell culture obtained in step (e) comprises cells forming a basal glandular compartment.

21. The method of any one of the Items 18 to 20, wherein the cells express MUC6.

22. The method of Item 21, wherein the WNT pathway is not activated, or/and wherein the WNT pathway is at least partially inhibited.

23. The method of Item 22, wherein
(a) the cell is cultured in a medium essentially free of a WNT activator, or/and
(b) wherein the cell is co-cultured with a cell capable of inhibiting at least partially the WNT pathway.

24. The method of Item 22 or 23, wherein the cell is cultured in a medium essentially free of WNT3 and RSPO1.

25. The method of any one of Items 22 to 24, wherein the epithelial cell provided in step (a) is a gastric mucosa cell.

26. The method of Item 25, wherein the cell culture obtained in step (e) comprises a cell exhibiting a foveolar phenotype.

27. The method of Item 26, wherein the cell expresses MUC5AC.

28. The method of any one of the Items 25 to 27, wherein the cell is co-cultured with a gastric stromal cell.

29. The method of any one of the preceding Items, wherein the epithelial cell provided in step (a) is selected from
(i) primary epithelial cells, and
(ii) pluripotent cells.

30. The method of any one of the preceding Items, wherein the cell provided in step (a) comprises a genetically modified cell.

31. The method of any one of the preceding Items, wherein the epithelial cells provided in step (a) are obtained from an organoid comprising epithelial cells.

32. The method of any one of the preceding Items, wherein the epithelial cell is cultured with non-epithelial cells.

33. The method of any one of the preceding Items, wherein the epithelial cell provided in step (a) is a result of Induced stem cells technology.

34. Cell culture, comprising epithelial cells, arranged in an epithelial monolayer on a solid surface, wherein the epithelial cells are polarized columnar epithelial cells.

35. Cell culture, comprising epithelial cells, arranged in an adjoining epithelial monolayer on a solid semi-permeable surface, wherein the epithelial cells are polarized columnar epithelial cells.

36. The cell culture of Item 34 or 35, wherein said polarized columnar epithelial cells comprise a basal side directed to the solid surface, and an apical side.

37. The cell culture of any one of the Items 34 to 36, produced by the method of any one of the Items 1 to 33.

38. A carrier comprising a solid surface, said solid surface comprising an epithelial cell monolayer, wherein the epithelial cells are polarized columnar epithelial cells.

39. The carrier of Item 38, wherein said polarized columnar epithelial cells comprise a basal side directed to the solid surface, and an apical side.

40. The carrier of Item 38 or 39, produced by the method of any one of the Items 1 to 33.

41. A carrier, comprising the cell culture of any one of the Items 34 to 37.

42. Use of a cell culture of any one of the Items 34 to 37 or a carrier of any one of the Items 38 to 41, (a) in a screening method for the identification of a compound capable of interacting with an epithelial cell,
(b) in a method for the determination of the interaction of a compound with an epithelial cell,
(c) in a method for the determination of the interaction of a cell with an epithelial cell, or/and
(d) in a method for the investigation of cellular differentiation of an epithelial cell.

43. Use of a cell culture of any one of the Items 34 to 37 or a carrier of any one of the Items 38 to 41,
(a) in a method for the determination of the interaction of a compound with an epithelial cell,
(b) in a method for the determination of the effect of a compound on epithelial secretion in the mucus,
(c) in a method for the determination of the interaction of a cell with an epithelial cell, or/and
(d) in a method for the investigation of cellular differentiation of an epithelial cell.

44. A method for the determination of the interaction of a compound with an epithelial cell, comprising the steps
(a) providing an epithelial cell culture of any one of the Items 34 to 37 or a carrier of any one of the Items 38 to 41,
(b) contacting the compound with the cell culture or carrier provided in step (a), and
(c) determining interaction of the compound with the cell culture.

45. A method for the determination of the effect of a compound on epithelial secretion in the mucus comprising the steps
(a) providing an epithelial cell culture of any one of the Items 34 to 37 or a carrier of any one of the Items 38 to 41,
(b) contacting the compound with the cell culture or carrier provided in step (a), and
(c) determining the mucus composition.

46. A method for the determination of the interaction of a non-epithelial cell with an epithelial cell comprising the steps
(a) providing an epithelial cell culture of any one of the Items 34 to 37 or a carrier of any one of the Items 38 to 41,
(b) co-cultivating of the epithelial cells with the cell culture or carrier provided in step (a), and
(c) determining the interaction of the non-epithelial cells with the cell culture.

47. The method of Item 46, wherein the non-epithelial cell is an immune cell or a myofibroblast.

48. The method of Item 47 wherein the non-epithelial cell is a pathogenic bacteria or virus or a portion of them.

49. A method for the investigation of cellular differentiation of an epithelial cell, comprising the steps
(a) providing an epithelial cell culture of any one of the Items 34 to 37 or a carrier of any one of the Items 38 to 41,
(b) contacting the cell culture provided in step (a) with an agent capable of inducing cellular differentiation, and
(c) determining cellular differentiation of the cell within the cell culture.

50. A screening method for the identification of a compound capable of interacting with an epithelial cell, comprising the steps
(a) providing an epithelial cell culture of any one of the Items 34 to 37 or a carrier of any one of the Items 38 to 41,
(b) contacting at least one compound with the cell culture provided in step (a),
(c) determining interaction of the at least one compound with the cell culture, and
(d) selecting at least one compound which interact with the cell culture, as determined in step (c).

51. A method for the determination of the interaction of a compound with an epithelial cell, comprising the steps
(a) providing an epithelial cell culture of any one of the Items 34 to 37 or a carrier of any one of the Items 38 to 41,
(b) contacting the compound with the cell culture provided in step (a), and
(c) determining interaction of the compound with the cell culture.

52. The method of Item 50 or 51, comprising culturing the cell culture in co-culture with a non-epithelial cell.

53. The method of Item 52, wherein the non-epithelial cell is a bacterial cell.

54. The method of Item 53, wherein the bacterial cell is a *Helicobacter* cell.

55. The method of Item 52, wherein the epithelial cell culture is a gastric epithelial cell culture, and the cell is a *Helicobacter* cell.

56. The method of Item 52, wherein the non-epithelial cell is an immune cell or a myofibroblast.

57. A method for the determination of the interaction of a non-epithelial cell with an epithelial cell, comprising the steps
(a) providing an epithelial cell culture of any one of the Items 34 to 37 or a carrier of any one of the Items 38 to 41,
(b) contacting the non-epithelial cell with the cell culture provided in step (a), and
(c) determining interaction of the cell with the cell culture.

58. The method of Item 57, wherein the non-epithelial cell is a bacterial cell.

59. The method of Item 58, wherein the bacterial cell is a *Helicobacter* cell.

60. The method of Item 57, wherein the epithelial cell culture is a gastric epithelial cell culture, and the non-epithelial cell is a *Helicobacter* cell.

61. The method of Item 57, wherein the non-epithelial cell is an immune cell or a myofibroblast.

62. The method of any one of the Items 50 to 61, wherein the interaction in affects growth or/and propagation of the cell culture.

63. The method of Item 50 to 62, wherein growth or/and propagation of the cell culture is inhibited.

64. A method for the investigation of cellular differentiation of an epithelial cell, comprising the steps
(a) providing an epithelial cell culture of any one of the Items 34 to 37 or a carrier of any one of the Items 38 to 41,
(b) contacting the cell culture provided in step (a) with an agent capable of inducing cellular differentiation, and
(c) determining cellular differentiation of the cell within the cell culture.

The invention claimed is:

1. A method of culturing an epithelial cell on a solid semi-permeable surface, consisting of the steps:
   (a) providing a primary epithelial cell isolated from tissues with a columnar epithelium lining, or a cell derived from an induced pluripotent stem cell which has been differentiated into an epithelial cell,
   (b) contacting the epithelial cell with a solid semi-permeable surface,
   (c) culturing the cell of (b) under air-liquid interface conditions,
   (d) (i) obtaining the cell culture in step (c), removing the cells from the solid semi-permeable surface by enzymatic digestion, and
   (ii) repeating steps (b) and (c),
   (e) obtaining a mucosoid cell culture and optionally co-culturing the mucosoid cell culture with another cell culture,
   (f) optionally isolating mucus from the cultured epithelial cell, and
   (g) optionally differentiating the epithelial cells obtained in step (e) by introducing differentiation niche factors into a culture medium,
   wherein the mucosoid cell culture obtained in step (e) comprises a continuous epithelial monolayer on the solid semi-permeable surface, wherein the epithelial cells are polarized columnar epithelial cells, and wherein the cell culture maintains a sufficient relative number of regenerative cells possessing the ability to undergo several rounds of cell division so that the mucosoid cell culture can be expanded and is long-lived for at least six months.

2. The method of claim 1, wherein the solid semi-permeable surface is a porous surface, wherein the pores in the porous surface have a pore size so that during culture the cells do not pass through the porous surface, and wherein said porous surface is comprised within a carrier.

3. The method of claim 1, wherein the solid semi-permeable surface of step (b) is coated with an extracellular matrix protein before contacting the surface with the cells.

4. The method of claim 1, wherein culture medium is used in step (c), which contains stem cell promoting factors.

5. The method of claim 1, wherein the polarized columnar epithelial cells comprise a basal side faced to the solid surface, and an apical side at the opposite end.

6. The method of claim 5, wherein the polarized columnar epithelial cells produce mucus on the apical side.

7. The method of claim 1, wherein the epithelial cells obtained in step (e) are capable of differentiation and/or to maintain their stemness potential.

8. The method of claim 1, wherein the epithelial cells obtained in step (e) are differentiated by introducing differentiation niche factors into a culture medium.

9. The method of claim 1, wherein mucus is isolated from the cultured epithelial cell.

10. The method of claim 1, wherein a bacterial cell and/or microbiome is co-cultured with the epithelial cell.

11. The method of claim 1, wherein the tissues with a columnar epithelium lining are selected from stomach, colon, gall bladder and fallopian tube.

12. The method of claim 1, wherein the epithelial cells obtained in step (e) are polarized columnar epithelial cells and are co-cultured with cells from the mucosa that are not polarized columnar epithelial cells.

13. The method of claim 1, wherein the epithelial cells obtained in step (e) are co-cultured with a non-epithelial cell.

14. The method of claim 13, wherein the non-epithelial cell is an immune cell or a myofibroblast.

15. The method of claim 13, wherein the non-epithelial cell is a bacterium, a parasite or a virus, or a portion thereof.

16. The method of claim 13, wherein the epithelial cells obtained in step (e) are polarized columnar epithelial cells and are co-cultured with cells from the mucosa that are not polarized columnar epithelial cells.

* * * * *